US011065318B2

(12) United States Patent
Franzusoff et al.

(10) Patent No.: US 11,065,318 B2
(45) Date of Patent: *Jul. 20, 2021

(54) YEAST-MUC1 IMMUNOTHERAPEUTIC COMPOSITIONS AND USES THEREOF

(71) Applicants: GlobeImmune, Inc., Lousiville, CO (US); The USA, as represented by the Secretary, Dept. of Health and Human Services, Bethesda, MD (US)

(72) Inventors: Alex Franzusoff, Los Altos, CA (US); Zhimin Guo, Superior, CO (US); Jeffrey Schlom, Potomac, MD (US); Kwong-Yok Tsang, Bethesda, MD (US)

(73) Assignees: GlobeImmune, Inc., Louisville, CO (US); The USA, as represented by the Secretary, Dept. of Health and Human Services, Bethesda, MD (US)

( * ) Notice: Subject to any disclaimer, the term of this patent is extended or adjusted under 35 U.S.C. 154(b) by 133 days.

This patent is subject to a terminal disclaimer.

(21) Appl. No.: 16/211,492

(22) Filed: Dec. 6, 2018

(65) Prior Publication Data

US 2019/0231859 A1   Aug. 1, 2019

Related U.S. Application Data

(60) Continuation of application No. 15/358,797, filed on Nov. 22, 2016, now Pat. No. 10,188,714, which is a division of application No. 13/803,757, filed on Mar. 14, 2013, now Pat. No. 9,533,031, which is a continuation of application No. PCT/US2012/051299, filed on Aug. 17, 2012.

(60) Provisional application No. 61/524,407, filed on Aug. 17, 2011.

(51) Int. Cl.
| | |
|---|---|
| *A61K 39/00* | (2006.01) |
| *C07K 14/47* | (2006.01) |
| *A61K 35/13* | (2015.01) |
| *A61K 35/17* | (2015.01) |
| *A61K 35/28* | (2015.01) |
| *A61K 31/65* | (2006.01) |
| *A61K 31/704* | (2006.01) |
| *A61K 31/7068* | (2006.01) |

(52) U.S. Cl.
CPC ........ *A61K 39/00117* (2018.08); *A61K 31/65* (2013.01); *A61K 31/704* (2013.01); *A61K 31/7068* (2013.01); *A61K 35/13* (2013.01); *A61K 35/17* (2013.01); *A61K 35/28* (2013.01); *A61K 39/0002* (2013.01); *C07K 14/4727* (2013.01); *A61K 2039/523* (2013.01); *A61K 2039/525* (2013.01); *A61K 2039/6031* (2013.01)

(58) Field of Classification Search
CPC ...................... A61K 39/00117; A61K 39/0002
See application file for complete search history.

(56) References Cited

U.S. PATENT DOCUMENTS

| | | | |
|---|---|---|---|
| 4,775,622 A | 10/1988 | Hitzeman et al. | |
| 5,234,830 A | 8/1993 | Oshima et al. | |
| 5,310,654 A | 5/1994 | Isberg et al. | |
| 5,413,914 A | 5/1995 | Franzusoff | |
| 5,830,463 A | 11/1998 | Duke et al. | |
| 5,858,378 A | 1/1999 | Bostwick | |
| 5,919,651 A | 7/1999 | Hitzeman et al. | |
| 7,083,787 B2 | 8/2006 | Duke et al. | |
| 7,439,042 B2 | 10/2008 | Duke et al. | |
| 7,465,454 B2 | 12/2008 | Franzusoff et al. | |
| 7,999,071 B2 | 8/2011 | Schlom et al. | |
| 9,533,031 B2 | 1/2017 | Franzusoff et al. | |
| 10,188,714 B2 * | 1/2019 | Franzusoff | A61K 31/7068 |
| 2002/0044948 A1 | 4/2002 | Samir et al. | |
| 2003/0035810 A1 | 2/2003 | Caplan | |
| 2005/0226888 A1 | 10/2005 | Deisseroth et al. | |
| 2006/0147477 A1 | 7/2006 | Cabezon Siliva et al. | |
| 2007/0172503 A1 | 7/2007 | Selitrennikoff et al. | |
| 2007/0224208 A1 | 9/2007 | Guo et al. | |
| 2008/0003239 A1 | 1/2008 | Duke et al. | |
| 2008/0166367 A1 | 7/2008 | Panicali et al. | |
| 2009/0054622 A1 | 2/2009 | Hanisch | |
| 2010/0034840 A1 | 2/2010 | Apelian et al. | |
| 2010/0111912 A1 | 5/2010 | Apelian et al. | |
| 2010/0189749 A1 | 7/2010 | Franzusoff et al. | |
| 2011/0256098 A1 | 10/2011 | Apelian et al. | |
| 2012/0321664 A1 | 12/2012 | Bellgrau et al. | |
| 2013/0315941 A1* | 11/2013 | Franzusoff | A61K 39/0002 424/185.1 |
| 2017/0224794 A1 | 8/2017 | Franzusoff et al. | |

FOREIGN PATENT DOCUMENTS

| | | |
|---|---|---|
| EP | 0414404 | 2/1991 |
| FR | 2486400 | 1/1982 |
| JP | 2007-535304 | 12/2007 |
| JP | 2009-544760 | 12/2009 |

(Continued)

OTHER PUBLICATIONS

Rudikoff et al. (PNAS USA, 1982, 79: 1979-1983) (Year: 1982).*
Coleman et al. (Research in Immunology, 1994; 145(1): 33-36) (Year: 1994).*
Abaza et al. (Journal of Protein Chemistry, 1992 vol. 11, No. 5, 433-444) (Year: 1992).*

(Continued)

*Primary Examiner* — Peter J Reddig
(74) *Attorney, Agent, or Firm* — Sheridan Ross P.C.

(57) ABSTRACT

Disclosed are yeast-based immunotherapeutic compositions comprising mucin-1 (MUC1), as well as methods for the prevention and/or treatment of cancers characterized by the expression or overexpression of mucin-1 (MUC1).

12 Claims, 3 Drawing Sheets

Specification includes a Sequence Listing.

(56) References Cited

FOREIGN PATENT DOCUMENTS

| RU | 2370537 | 10/2009 |
|---|---|---|
| WO | WO 01/18035 | 3/2001 |
| WO | WO 03/106648 | 12/2003 |
| WO | WO 2005/051991 | 6/2005 |
| WO | WO 2007/008780 | 1/2007 |
| WO | WO 2010/065626 | 6/2010 |
| WO | WO 2010/0121180 | 10/2010 |
| WO | WO 2011/115914 | 9/2011 |
| WO | WO 2012/019127 | 2/2012 |
| WO | WO 2012/083302 | 6/2012 |
| WO | WO 2012/109404 | 8/2012 |
| WO | WO 2012/125998 | 9/2012 |
| WO | WO 2012/174220 | 12/2012 |
| WO | WO 2013/025972 | 2/2013 |

OTHER PUBLICATIONS

Burgess et al (J of Cell Bio. 111:2129-2138, 1990) (Year: 1990).*
Official Action for European Patent Application No. 12824638.6 dated Apr. 12, 2019, 4 pages.
Bizzini et al. "Use of live *Saccharomyces cerevisiae* cells as a biological response modifier in experimental infections," FEMS Microbiology Immunology, 1990, vol. 64, pp. 155-168.
Brake et al. "alpha-Factor-directed synthesis and secretion of mature foreign proteins in *Saccharomyces cerevisiae*," Proceedings of the National Academy of Sciences USA, Aug. 1984, vol. 81, pp. 4642-4646.
Bui et al. "Mutation-specific control of BCR-ABL T315I positive leukemia with a recombinant yeast-based therapeutic vaccine in a murine model," Vaccine, Aug. 2010, vol. 28, No. 37, pp. 6028-6035.
Eto et al., "Immunization with recombinant *Escherichia coli* expressing retinal S-antigen-induced experimental autoimmune uveitis (EAU) in Lewis rats", Cellular Immunology, vol. 147, No. 1 Mar. 1993, pp. 203-214.
Franzusoff, A. et al. "Yeasts Encoding Tumour Antigens in Cancer Immunotherapy," Expert Opinion on Biological Therapy, Apr. 2005, vol. 5, No. 4, pp. 565-575.
Franzusoff et al. "Biochemical and Genetic Definition of the Cellular Protease Required for HIV-1 gp160 Processing," The Journal of Biological Chemistry, Feb. 1995, vol. 270, No. 7, pp. 3154-3159.
Fujita et al. "Studies in the development of Japanese encephalitis vaccine: expression of virus envelope glycoprotein V3 (E) gene in yeast," Bulletin of the World Health Organization, Feb. 1987, vol. 65, No. 3, pp. 303-308.
Lu, et al., "Mutation-Selective Tumor Remission with Ras-Targeted, Whole Yeast-Based Immunotherapy," Cancer Research, 2004, vol. 64, pp. 5084-5088.
Klepfer et al. "Characterization of rabies glycoprotein expressed in yeast," Archives of Virology, 1993, vol. 128, pp. 269-286.
MeSH, "trophoblastin [Supplementary Concept]," National Center for Biotechnology Information (NCBI), 1979, [retrieved on Jun. 1, 2018], 1 page. Retrieved from: www.ncbi.nlm.nih.gov/mesh/67020947.
MeSH, "TYRP1 protein, human [Supplementary Concept]," National Center for Biotechnology Information (NCBI), 2004, [retrieved on Jun. 1, 2018], 1 page. Retrieved from: www.ncbi.nlm.nih.gov/mesh/67489799.
Moore et al., "Novel yeast-based vaccine 1-40, against HIV-SF2 gp160 promotes a cytotoxic 43-62 cell response." FASEB Journal (online), vol. 10. No. 6. 1996, p. A1473, ZP002186594, Joint Meeting of the American Society for Biochemistry and Molecular Biology, the American Society for Investigative Pathology and the American Association of Immunologists; New Orleans, LA, USA; Jun. 2-6, 1996.
Pakula et al., "Genetic Analysis of Protein Stability and Function," Annual Review of Genetics, 1989, vol. 23, pp. 289-310. (Abstract only).
Quinlin et al. "Context of MUC1 epitope: Immunogenicity," Oncology Reports, Feb. 2007, vol. 17, No. 2, pp. 453-456.

Schreuder et al. "Yeast expressing hepatitis B virus surface antigen determinants on its surface: implications for a possible oral vaccine," Vaccine, Apr. 1996, vol. 14, No. 5, pp. 383-388.
Sinai et al. "Enhancement of Resistance to Infectious Diseases by Oral Administration of Brewer's Yeast," Infection and Immunity, May 1974, vol. 9, No. 5, pp. 781-787.
Stubbs, et al., "Whole Recombinant Yeast Vaccine Activates Dendritic Cells and Elicits Protective Cell-Mediated Immunity," National Medicine, May 2001, vol. 7, No. 5, pp. 1-5.
Tsang et al. "A Human Cytotoxic T-Lymphocyte Epitope and Its Agonist Epitope from the Nonvariable Number of Tandem Repeat Sequence of MUC-1," Clinical Cancer Research, Mar. 2004, vol. 10, No. 6, pp. 2139-2149.
Valenzuela et al. "Antigen engineering in yeast: Synthesis and assembly of hybrid hepatitis B surface antigen-Herpes simplex 1 gD particles", Bio/Technology, Apr. 1985, vol. 3, 323-326.
Wansley et al. "Vaccination with a Recombinant *Saccharomyces cerevisiae* Expressing a Tumor Antigen Breaks Immune Tolerance and Elicits Therapeutic Antitumor Responses," Clinical Cancer Research, Jul. 2008, vol. 14, No. 13, pp. 4316-4325.
International Search Report and Written Opinion for International (PCT) Patent Application No. PCT/US2012/051299, dated Nov. 16, 2012 17 pages.
International Preliminary Report on Patentability for International (PCT) Patent Application No. PCT/US2012/051299, dated Feb. 27, 2014 8 pages.
Official Action for Australian Patent Application No. 2012296425 dated Sep. 27, 2016, 4 pages.
Notice of Acceptance for Australian Patent Application No. 2012296425 dated Oct. A70, 3 pages.
Official Action for Canadian Patent Application No. 2,844,500 dated Jul. 27, 2018, 6 pages.
English Translation of Official Action for China Patent Application No. 201280051154.2, dated Mar. 18, 2015 11 pages.
English Translation of Official Action for China Patent Application No. 201280051154.2, dated Feb. 23, 2016, 10 pages.
English Translation of Official Action for China Patent Application No. 201280051154.2, dated Oct. 8, 2016, 4 pages.
English Translation of Official Action for China Patent Application No. 201280051154.2, dated Jul. 3, 2017, 4 pages.
English Translation of Official Action for China Patent Application No. 201280051154.2, dated Mar. 27, 2018, 4 pages.
Extended European Search Report for European Patent Application No. 12824638.6 dated May 13, 2015, 5 pages.
Official Action for European Patent Application No. 12824638.6 dated Feb. 12, 2016, 4 pages.
Official Action for European Patent Application No. 12824638.6 dated Dec. 8, 2016, 4 pages.
Official Action for European Patent Application No. 12824638.6 dated Jan. 2, 2018, 3 pages.
Official Action (with English translation) for Israeli Patent Application No. 230863 dated Apr. 26, 2017, 5 pages.
Official Action (with English translation) for Israeli Patent Application No. 257533 dated Jun. 12, 2018, 7 pages.
Official Action (with English translation) for Japanese Patent Application No. 2014-526241 dated Jul. 19, 2016, 9 pages.
Notice of Allowance (with English translation) for Japanese Patent Application No. 2014-526241 dated Mar. 1, 2017, 2 pages.
Examination Report for New Zealand Patent Application No. 622335, dated Dec. 12, 2014 2 pages.
Further Examination Report for New Zealand Patent Application No. 622335, dated Mar. 11, 2016 2 pages.
Further Examination Report for New Zealand Patent Application No. 622335, dated May 19, 2016 2 pages.
Notice of Acceptance for New Zealand Patent Application No. 622335, dated Jul. 1, 2016 1 page.
Examination Report for New Zealand Patent Application No. 717338 dated Mar. 11, 2016, 2 pages.
Official Action (with English translation) for Russian Patent Application No. 2014109741/10 dated Sep. 29, 2016, 12 pages.
Notice of Allowance (with English translation) for Russian Patent Application No. 2014109741/10 dated Apr. 21, 2017, 12 pages.

(56) References Cited

OTHER PUBLICATIONS

Official Action for U.S. Appl. No. 13/803,757, dated Jan. 5, 2015 10 pages.
Official Action for U.S. Appl. No. 13/803,757, dated Jun. 23, 2015, 11 pages.
Official Action for U.S. Appl. No. 13/803,757, dated Feb. 9, 2016, 10 pages.
Notice of Allowance for U.S. Appl. No. 13/803,757, dated Aug. 26, 2016, 9 pages.
Official Action for U.S. Appl. No. 15/358,797, dated Jun. 6, 2018, 6 pages.
Notice of Allowance for U.S. Appl. No. 15/358,797, dated Sep. 7, 2018, 8 pages.
NCBI Reference Sequence: NP_001191214.1, "mucin-1 isoform 9 precursor [*Homo sapiens*]," Feb. 26, 2011.
Official Action for Australian Patent Application No. 2017248462 dated Oct. 19, 2018, 2 pages.
Official Action (with English Analysis Report) for Korean Patent Application No. 10-2014-7006872 dated Nov. 20, 2018, 11 pages.
Notice of Allowance for Australian Patent Application No. 2017248462 dated Sep. 30, 2019, 3 pages.
Official Action for Canadian Patent Application No. 2,844,500 dated Aug. 20, 2019, 5 pages.
Official Action for European Patent Application No. 12824638.6 dated Aug. 28, 2019, 4 pages.
Notice of Allowance (with English translation) for Japanese Patent Application No. 2018-040308 dated Jul. 9, 2019, 2 pages.
Notice of Allowance (with English translation) for Korean Patent Application No. 10-2014-7006872 dated Aug. 22, 2019, 3 pages.
Notice of Allowance (with English translation) for China Patent Application No. 201280051154.2, dated Feb. 28, 2019, 5 pages.
Official Action for Indian Patent Application No. 1981/DELNP/2014 dated Dec. 17, 2018, 6 pages.
Official Action (with English translation) for Japanese Patent Application No. 2018-040308 dated Apr. 2, 2019, 3 pages.
Official Action for Canadian Patent Application No. 2,844,500 dated Oct. 9, 2020, 3 pages.
Official Action for European Patent Application No. 12824638.6 dated Jun. 23, 2020, 5 pages.
Official Action (with English translation) for Japanese Patent Application No. 2019-145946 dated Jul. 21, 2020, 6 pages.
Official Action for Singapore Patent Application No. 10201607663Y dated Jul. 1, 2020, 10 pages.
Official Action (with English machine translation) for Brazilian Patent Application No. BR112014003477-0 dated Jul. 9, 2020, 8 pages.
Official Action (with English machine translation) for Brazilian Patent Application No. BR112014003477-0 dated Dec. 3, 2020, 9 pages.
Fong et al., "Altered peptide ligand vaccination with Flt3 ligand expanded dendritic cells for tumor immunotherapy," Proceedings of the National Academy of Sciences, Jul. 17, 2001, vol. 98(15), pp. 8809-8814.
Van Stipdonk et al., "Design of Agonistic Altered Peptides for the Robust Induction of CTL Directed towards H-2D$^0$ in Complex with the Melanoma-Associated Epitope gp100," American Association for Cancer Research, DOI: 10.1158/0008-5472.CAN-09-1724, Sep. 29, 2009, vol. 69(19), pp. 7784-7792.
Official Action for European Patent Application No. 12824638.6 dated Apr. 23, 2021, 6 pages.

* cited by examiner

SEQUENCE LISTING

<160> NUMBER OF SEQ ID NOS: 25

<210> SEQ ID NO 1
<211> LENGTH: 1209
<212> TYPE: DNA
<213> ORGANISM: Homo sapiens
<220> FEATURE:
<221> NAME/KEY: CDS
<222> LOCATION: (67)..(888)

<400> SEQUENCE: 1

```
acctctcaag cagccagcgc ctgcctgaat ctgttctgcc ccctccccac ccatttcacc         60 accacc atg aca ccg ggc acc cag tct cct ttc ttc ctg ctg ctc             108
       Met Thr Pro Gly Thr Gln Ser Pro Phe Phe Leu Leu Leu
       1               5                   10 ctc aca gtg ctt aca gtt gtt acg ggt tct ggt cat gca agc tct acc         156
Leu Thr Val Leu Thr Val Val Thr Gly Ser Gly His Ala Ser Ser Thr
15                  20                  25                  30 cca ggt gga gaa aag gag act tcg gct acc cag aga agt tca gtg ccc         204
Pro Gly Gly Glu Lys Glu Thr Ser Ala Thr Gln Arg Ser Ser Val Pro
                35                  40                  45 agc tct act gag aag aat gct ttg tct act ggg gtc tct ttc ttt ttc         252
Ser Ser Thr Glu Lys Asn Ala Leu Ser Thr Gly Val Ser Phe Phe Phe
            50                  55                  60 ctg tct ttt cac att tca aac ctc cag ttt aat tcc tct ctg gaa gat         300
Leu Ser Phe His Ile Ser Asn Leu Gln Phe Asn Ser Ser Leu Glu Asp
        65                  70                  75 ccc agc acc gac tac tac caa gag ctg cag aga gac att tct gaa atg         348
Pro Ser Thr Asp Tyr Tyr Gln Glu Leu Gln Arg Asp Ile Ser Glu Met
```

```
ttt ttg cag att tat aaa caa ggg ggt ttt ctg ggc ctc tcc aat att      396
Phe Leu Gln Ile Tyr Lys Gln Gly Gly Phe Leu Gly Leu Ser Asn Ile
 95                 100                 105                 110 aag ttc agg cca gga tct gtg gtg gta caa ttg act ctg gcc ttc cga      444
Lys Phe Arg Pro Gly Ser Val Val Val Gln Leu Thr Leu Ala Phe Arg
                115                 120                 125 gaa ggt acc atc aat gtc cac gac gtg gag aca cag ttc aat cag tat      492
Glu Gly Thr Ile Asn Val His Asp Val Glu Thr Gln Phe Asn Gln Tyr
            130                 135                 140 aaa acg gaa gca gcc tct cga tat aac ctg acg atc tca gac gtc agc      540
Lys Thr Glu Ala Ala Ser Arg Tyr Asn Leu Thr Ile Ser Asp Val Ser
        145                 150                 155 gtg agt gat gtg cca ttt cct ttc tct gcc cag tct ggg gct ggg gtg      588
Val Ser Asp Val Pro Phe Pro Phe Ser Ala Gln Ser Gly Ala Gly Val
160                 165                 170 cca ggc tgg ggc atc gcg ctg ctg gtg ctg gtc tgt gtt ctg gtt gcg      636
Pro Gly Trp Gly Ile Ala Leu Leu Val Leu Val Cys Val Leu Val Ala
175                 180                 185                 190 ctg gcc att gtc tat ctc att gcc ttg gct gtc tgt cag tgc cgc cga      684
Leu Ala Ile Val Tyr Leu Ile Ala Leu Ala Val Cys Gln Cys Arg Arg
                195                 200                 205 aag aac tac ggg cag ctg gac atc ttt cca gcc cgg gat acc tac cat      732
Lys Asn Tyr Gly Gln Leu Asp Ile Phe Pro Ala Arg Asp Thr Tyr His
            210                 215                 220 cct atg agc gag tac ccc acc tac cac acc cat ggg cgc tat gtg ccc      780
Pro Met Ser Glu Tyr Pro Thr Tyr His Thr His Gly Arg Tyr Val Pro
        225                 230                 235 cct agc agt acc gat cgt agc ccc tat gag aag gtt tct gca ggt aat      828
Pro Ser Ser Thr Asp Arg Ser Pro Tyr Glu Lys Val Ser Ala Gly Asn
240                 245                 250 ggt ggc agc agc ctc tct tac aca aac cca gca gtg gca gcc act tct      876
Gly Gly Ser Ser Leu Ser Tyr Thr Asn Pro Ala Val Ala Ala Thr Ser
255                 260                 265                 270 gcc aac ttg tag gggcacgtcg cccgctgagc tgagtggcca gccagtgcca         928
Ala Asn Leu ttccactcca ctcaggttct tcagggccag agccctgca ccctgtttgg gctggtgagc    988
tgggagttca ggtgggctgc tcacagcctc cttcagaggc cccaccaatt tctcggacac   1048
ttctcagtgt gtgaagctc atgtgggccc ctgagggctc atgcctggga agtgttgtgg   1108
tgggggctcc caggaggact ggcccagaga gccctgagat agcgggatc ctgaactgga    1168 ctgaataaaa cgtggtctcc cactgcgcca aaaaaaaaaa a                       1209

<210> SEQ ID NO 2
<211> LENGTH: 273
<212> TYPE: PRT
<213> ORGANISM: Homo sapiens

<400> SEQUENCE: 2

Met Thr Pro Gly Thr Gln Ser Pro Phe Phe Leu Leu Leu Leu Leu Thr
 1               5                  10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Leu Ser Thr Gly Val Ser Phe Phe Phe Leu Ser
    50                  55                  60
```

```
Phe His Ile Ser Asn Leu Gln Phe Asn Ser Ser Leu Glu Asp Pro Ser
 65                  70                  75                  80

Thr Asp Tyr Tyr Gln Glu Leu Gln Arg Asp Ile Ser Glu Met Phe Leu
             85                  90                  95

Gln Ile Tyr Lys Gln Gly Gly Phe Leu Gly Leu Ser Asn Ile Lys Phe
        100                 105                 110

Arg Pro Gly Ser Val Val Gln Leu Thr Leu Ala Phe Arg Glu Gly
        115                 120                 125

Thr Ile Asn Val His Asp Val Glu Thr Gln Phe Asn Gln Tyr Lys Thr
    130                 135                 140

Glu Ala Ala Ser Arg Tyr Asn Leu Thr Ile Ser Asp Val Ser Val Ser
145                 150                 155                 160

Asp Val Pro Phe Pro Phe Ser Ala Gln Ser Gly Ala Gly Val Pro Gly
                165                 170                 175

Trp Gly Ile Ala Leu Leu Val Leu Val Cys Val Leu Val Ala Leu Ala
            180                 185                 190

Ile Val Tyr Leu Ile Ala Leu Ala Val Cys Gln Cys Arg Arg Lys Asn
        195                 200                 205

Tyr Gly Gln Leu Asp Ile Phe Pro Ala Arg Asp Thr Tyr His Pro Met
    210                 215                 220

Ser Glu Tyr Pro Thr Tyr His Thr His Gly Arg Tyr Val Pro Pro Ser
225                 230                 235                 240

Ser Thr Asp Arg Ser Pro Tyr Glu Lys Val Ser Ala Gly Asn Gly Gly
                245                 250                 255

Ser Ser Leu Ser Tyr Thr Asn Pro Ala Val Ala Ala Thr Ser Ala Asn
            260                 265                 270

Leu

<210> SEQ ID NO 3
<211> LENGTH: 1182
<212> TYPE: DNA
<213> ORGANISM: Homo sapiens
<220> FEATURE:
<221> NAME/KEY: CDS
<222> LOCATION: (67)..(861)

<400> SEQUENCE: 3
acctctcaag cagccagcgc ctgcctgaat ctgttctgcc ccctccccac ccatttcacc      60 accacc atg aca ccg ggc acc cag tct cct ttc ttc ctg ctg ctg ctc      108
       Met Thr Pro Gly Thr Gln Ser Pro Phe Phe Leu Leu Leu Leu
           1               5                  10 ctc aca gtg ctt aca gct acc aca gcc cct aaa ccc gca aca gtt gtt      156
Leu Thr Val Leu Thr Ala Thr Thr Ala Pro Lys Pro Ala Thr Val Val
 15                  20                  25                  30 acg ggt tct ggt cat gca agc tct acc cca ggt gga gaa aag gag act      204
Thr Gly Ser Gly His Ala Ser Ser Thr Pro Gly Gly Glu Lys Glu Thr
                 35                  40                  45 tcg gct acc cag aga agt tca gtg ccc agc tct act gag aag aat gct      252
Ser Ala Thr Gln Arg Ser Ser Val Pro Ser Ser Thr Glu Lys Asn Ala
             50                  55                  60 ttt aat tcc tct ctg gaa gat ccc agc acc gac tac tac caa gag ctg      300
Phe Asn Ser Ser Leu Glu Asp Pro Ser Thr Asp Tyr Tyr Gln Glu Leu
         65                  70                  75 cag aga gac att tct gaa atg ttt ttg cag att tat aaa caa ggg ggt      348
Gln Arg Asp Ile Ser Glu Met Phe Leu Gln Ile Tyr Lys Gln Gly Gly
     80                  85                  90 ttt ctg ggc ctc tcc aat att aag ttc agg cca gga tct gtg gtg gta      396
```

```
                                                                                      -continued Phe Leu Gly Leu Ser Asn Ile Lys Phe Arg Pro Gly Ser Val Val
 95                 100                 105                 110 caa ttg act ctg gcc ttc cga gaa ggt acc atc aat gtc cac gac gtg       444
Gln Leu Thr Leu Ala Phe Arg Glu Gly Thr Ile Asn Val His Asp Val
                    115                 120                 125 gag aca cag ttc aat cag tat aaa acg gaa gca gcc tct cga tat aac       492
Glu Thr Gln Phe Asn Gln Tyr Lys Thr Glu Ala Ala Ser Arg Tyr Asn
                130                 135                 140 ctg acg atc tca gac gtc agc gtg agt gat gtg cca ttt cct ttc tct       540
Leu Thr Ile Ser Asp Val Ser Val Ser Asp Val Pro Phe Pro Phe Ser
            145                 150                 155 gcc cag tct ggg gct ggg gtg cca ggc tgg ggc atc gcg ctg ctg gtg       588
Ala Gln Ser Gly Ala Gly Val Pro Gly Trp Gly Ile Ala Leu Leu Val
        160                 165                 170 ctg gtc tgt gtt ctg gtt gcg ctg gcc att gtc tat ctc att gcc ttg       636
Leu Val Cys Val Leu Val Ala Leu Ala Ile Val Tyr Leu Ile Ala Leu
175                 180                 185                 190 gct gtc tgt cag tgc cgc cga aag aac tac ggg cag ctg gac atc ttt       684
Ala Val Cys Gln Cys Arg Arg Lys Asn Tyr Gly Gln Leu Asp Ile Phe
                195                 200                 205 cca gcc cgg gat acc tac cat cct atg agc gag tac ccc acc tac cac       732
Pro Ala Arg Asp Thr Tyr His Pro Met Ser Glu Tyr Pro Thr Tyr His
            210                 215                 220 acc cat ggg cgc tat gtg ccc cct agc agt acc gat cgt agc ccc tat       780
Thr His Gly Arg Tyr Val Pro Pro Ser Ser Thr Asp Arg Ser Pro Tyr
        225                 230                 235 gag aag gtt tct gca ggt aat ggt ggc agc agc ctc tct tac aca aac       828
Glu Lys Val Ser Ala Gly Asn Gly Gly Ser Ser Leu Ser Tyr Thr Asn
240                 245                 250 cca gca gtg gca gcc act tct gcc aac ttg tag gggcacgtcg cccgctgagc    881
Pro Ala Val Ala Ala Thr Ser Ala Asn Leu
255                 260 tgagtggcca gccagtgcca ttccactcca ctcaggttct tcagggcag agccctgca       941 ccctgtttgg gctggtgagc tgggagttca ggtgggctgc tcacagcctc cttcagaggc    1001
cccaccaatt tctcggacac ttctcagtgt gtggaagctc atgtgggccc ctgagggctc    1061
atgcctggga agtgttgtgg tggggctcc caggaggact ggcccagaga gccctgagat    1121
agcggggatc ctgaactgga ctgaataaaa cgtggtctcc cactgcgcca aaaaaaaaa    1181 a                                                                    1182

<210> SEQ ID NO 4
<211> LENGTH: 264
<212> TYPE: PRT
<213> ORGANISM: Homo sapiens

<400> SEQUENCE: 4

Met Thr Pro Gly Thr Gln Ser Pro Phe Phe Leu Leu Leu Leu Thr
 1               5                  10                  15

Val Leu Thr Ala Thr Thr Ala Pro Lys Pro Ala Thr Val Val Thr Gly
                20                  25                  30

Ser Gly His Ala Ser Ser Thr Pro Gly Gly Glu Lys Glu Thr Ser Ala
            35                  40                  45

Thr Gln Arg Ser Ser Val Pro Ser Ser Thr Glu Lys Asn Ala Phe Asn
        50                  55                  60

Ser Ser Leu Glu Asp Pro Ser Thr Asp Tyr Tyr Gln Glu Leu Gln Arg
65                  70                  75                  80

Asp Ile Ser Glu Met Phe Leu Gln Ile Tyr Lys Gln Gly Gly Phe Leu
```

```
                    85                  90                  95
Gly Leu Ser Asn Ile Lys Phe Arg Pro Gly Ser Val Val Gln Leu
            100                 105                 110

Thr Leu Ala Phe Arg Glu Gly Thr Ile Asn Val His Asp Val Glu Thr
        115                 120                 125

Gln Phe Asn Gln Tyr Lys Thr Glu Ala Ala Ser Arg Tyr Asn Leu Thr
    130                 135                 140

Ile Ser Asp Val Ser Val Ser Asp Val Pro Phe Pro Phe Ser Ala Gln
145                 150                 155                 160

Ser Gly Ala Gly Val Pro Gly Trp Gly Ile Ala Leu Leu Val Leu Val
                165                 170                 175

Cys Val Leu Val Ala Leu Ala Ile Val Tyr Leu Ile Ala Leu Ala Val
            180                 185                 190

Cys Gln Cys Arg Arg Lys Asn Tyr Gly Gln Leu Asp Ile Phe Pro Ala
        195                 200                 205

Arg Asp Thr Tyr His Pro Met Ser Glu Tyr Pro Thr Tyr His Thr His
    210                 215                 220

Gly Arg Tyr Val Pro Pro Ser Ser Thr Asp Arg Ser Pro Tyr Glu Lys
225                 230                 235                 240

Val Ser Ala Gly Asn Gly Gly Ser Ser Leu Ser Tyr Thr Asn Pro Ala
                245                 250                 255

Val Ala Ala Thr Ser Ala Asn Leu
            260

<210> SEQ ID NO 5
<211> LENGTH: 1032
<212> TYPE: DNA
<213> ORGANISM: Homo sapiens
<220> FEATURE:
<221> NAME/KEY: CDS
<222> LOCATION: (51)..(845)

<400> SEQUENCE: 5
gcgcctgcct gaatctgttc tgcccctcc ccacccattt caccaccacc atg aca        56
                                                      Met Thr
                                                        1 ccg ggc acc cag tct cct ttc ttc ctg ctg ctg ctc ctc aca gtg ctt    104
Pro Gly Thr Gln Ser Pro Phe Phe Leu Leu Leu Leu Leu Thr Val Leu
        5                   10                  15 aca gct acc aca gcc cct aaa ccc gca aca gtt gtt aca ggt tct ggt    152
Thr Ala Thr Thr Ala Pro Lys Pro Ala Thr Val Val Thr Gly Ser Gly
    20                  25                  30 cat gca agc tct acc cca ggt gga gaa aag gag act tcg gct acc cag    200
His Ala Ser Ser Thr Pro Gly Gly Glu Lys Glu Thr Ser Ala Thr Gln
35                  40                  45                  50 aga agt tca gtg ccc agc tct act gag aag aat gct ttt aat tcc tct    248
Arg Ser Ser Val Pro Ser Ser Thr Glu Lys Asn Ala Phe Asn Ser Ser
                55                  60                  65 ctg gaa gat ccc agc acc gac tac tac caa gag ctg cag aga gac att    296
Leu Glu Asp Pro Ser Thr Asp Tyr Tyr Gln Glu Leu Gln Arg Asp Ile
            70                  75                  80 tct gaa atg ttt ttg cag att tat aaa caa ggg ggt ttt ctg ggc ctc    344
Ser Glu Met Phe Leu Gln Ile Tyr Lys Gln Gly Gly Phe Leu Gly Leu
        85                  90                  95 tcc aat att aag ttc agg cca gga tct gtg gtg gta caa ttg act ctg    392
Ser Asn Ile Lys Phe Arg Pro Gly Ser Val Val Val Gln Leu Thr Leu
    100                 105                 110 gcc ttc cga gaa ggt acc atc aat gtc cac gac atg gag aca cag ttc    440
```

|     |     |     |     |     |     |     |     |     |     |     |     |     |     |     |
| --- | --- | --- | --- | --- | --- | --- | --- | --- | --- | --- | --- | --- | --- | --- |
| Ala | Phe | Arg | Glu | Gly | Thr | Ile | Asn | Val | His | Asp | Met | Glu | Thr | Gln | Phe |
| 115 |     |     |     | 120 |     |     |     | 125 |     |     |     | 130 |

```
aat cag tat aaa acg gaa gca gcc tct cga tat aac ctg acg atc tca    488
Asn Gln Tyr Lys Thr Glu Ala Ala Ser Arg Tyr Asn Leu Thr Ile Ser
            135                 140                 145 gac gtc agc gtg agt ggt gtg cca ttt cct ttc tct gcc cag tct ggg    536
Asp Val Ser Val Ser Gly Val Pro Phe Pro Phe Ser Ala Gln Ser Gly
        150                 155                 160 gct ggg gtg cca ggc tgg ggc atc gcg ctg ctg gtg ctg gtc tgt gtt    584
Ala Gly Val Pro Gly Trp Gly Ile Ala Leu Leu Val Leu Val Cys Val
            165                 170                 175 ctg gtt gcg ctg gcc att gtc tat ctc att gcc ttg gct gtc tgt cag    632
Leu Val Ala Leu Ala Ile Val Tyr Leu Ile Ala Leu Ala Val Cys Gln
        180                 185                 190 tgc cgc cga aag aac tac ggg cag ctg gac atc ttt cca gcc cgg gat    680
Cys Arg Arg Lys Asn Tyr Gly Gln Leu Asp Ile Phe Pro Ala Arg Asp
195                 200                 205                 210 acc tac cat cct atg agc gag tac ccc acc tac cac acc cat ggg cgc    728
Thr Tyr His Pro Met Ser Glu Tyr Pro Thr Tyr His Thr His Gly Arg
            215                 220                 225 tat gtg ccc cct agc agt acc gat cgt agc ccc tat gag aag gtt tct    776
Tyr Val Pro Pro Ser Ser Thr Asp Arg Ser Pro Tyr Glu Lys Val Ser
        230                 235                 240 gca ggt aat ggt ggc agc agc ctc tct tac aca aac cca gca gtg gca    824
Ala Gly Asn Gly Gly Ser Ser Leu Ser Tyr Thr Asn Pro Ala Val Ala
            245                 250                 255 gcc act tct gcc aac ttg tag gggcacgtcg cccgctgagc tgagtggcca       875
Ala Thr Ser Ala Asn Leu
        260 gccagtgcca ttccactcca ctcaggttct tcagggccag agcccctgca ccctgtttgg  935 gctggtgagc tgggagttca ggtgggctgc tcacagcctc cttcagaggc cccaccaatt  995 tctcggacac ttctcagtgt gtggaagctc atgtggg                           1032

<210> SEQ ID NO 6
<211> LENGTH: 264
<212> TYPE: PRT
<213> ORGANISM: Homo sapiens

<400> SEQUENCE: 6

Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Thr Gly
            20                  25                  30

Ser Gly His Ala Ser Ser Thr Pro Gly Gly Glu Lys Glu Thr Ser Ala
        35                  40                  45

Thr Gln Arg Ser Ser Val Pro Ser Ser Thr Glu Lys Asn Ala Phe Asn
    50                  55                  60

Ser Ser Leu Glu Asp Pro Ser Thr Asp Tyr Tyr Gln Glu Leu Gln Arg
65                  70                  75                  80

Asp Ile Ser Glu Met Phe Leu Gln Ile Tyr Lys Gln Gly Gly Phe Leu
                85                  90                  95

Gly Leu Ser Asn Ile Lys Phe Arg Pro Gly Ser Val Val Val Gln Leu
            100                 105                 110

Thr Leu Ala Phe Arg Glu Gly Thr Ile Asn Val His Asp Met Glu Thr
        115                 120                 125

Gln Phe Asn Gln Tyr Lys Thr Glu Ala Ala Ser Arg Tyr Asn Leu Thr
    130                 135                 140
```

```
Ile Ser Asp Val Ser Val Ser Gly Val Pro Phe Pro Phe Ser Ala Gln
145                 150                 155                 160

Ser Gly Ala Gly Val Pro Gly Trp Gly Ile Ala Leu Leu Val Leu Val
                165                 170                 175

Cys Val Leu Val Ala Leu Ala Ile Val Tyr Leu Ile Ala Leu Ala Val
            180                 185                 190

Cys Gln Cys Arg Arg Lys Asn Tyr Gly Gln Leu Asp Ile Phe Pro Ala
        195                 200                 205

Arg Asp Thr Tyr His Pro Met Ser Glu Tyr Pro Thr Tyr His Thr His
    210                 215                 220

Gly Arg Tyr Val Pro Pro Ser Ser Thr Asp Arg Ser Pro Tyr Glu Lys
225                 230                 235                 240

Val Ser Ala Gly Asn Gly Gly Ser Ser Leu Ser Tyr Thr Asn Pro Ala
                245                 250                 255

Val Ala Ala Thr Ser Ala Asn Leu
            260
```

<210> SEQ ID NO 7
<211> LENGTH: 1166
<212> TYPE: DNA
<213> ORGANISM: Homo sapiens
<220> FEATURE:
<221> NAME/KEY: CDS
<222> LOCATION: (73)..(840)

<400> SEQUENCE: 7

```
cgctccacct ctcaagcagc cagcgcctgc ctgaatctgt tctgccccct ccccacccat      60
ttcaccacca cc atg aca ccg ggc acc cag tct cct ttc ttc ctg ctg ctg    111
              Met Thr Pro Gly Thr Gln Ser Pro Phe Phe Leu Leu Leu
                1               5                   10 ctc ctc aca gtg ctt aca gtt gtt acg ggt tct ggt cat gca agc tct       159
Leu Leu Thr Val Leu Thr Val Val Thr Gly Ser Gly His Ala Ser Ser
    15                  20                  25 acc cca ggt gga gaa aag gag act tcg gct acc cag aga agt tca gtg       207
Thr Pro Gly Gly Glu Lys Glu Thr Ser Ala Thr Gln Arg Ser Ser Val
30                  35                  40                  45 ccc agc tct act gag aag aat gct ttt aat tcc tct ctg gaa gat ccc       255
Pro Ser Ser Thr Glu Lys Asn Ala Phe Asn Ser Ser Leu Glu Asp Pro
                50                  55                  60 agc acc gac tac tac caa gag ctg cag aga gac att tct gaa atg ttt       303
Ser Thr Asp Tyr Tyr Gln Glu Leu Gln Arg Asp Ile Ser Glu Met Phe
            65                  70                  75 ttg cag att tat aaa caa ggg ggt ttt ctg ggc ctc tcc aat att aag       351
Leu Gln Ile Tyr Lys Gln Gly Gly Phe Leu Gly Leu Ser Asn Ile Lys
        80                  85                  90 ttc agg cca gga tct gtg gtg gta caa ttg act ctg gcc ttc cga gaa       399
Phe Arg Pro Gly Ser Val Val Val Gln Leu Thr Leu Ala Phe Arg Glu
    95                  100                 105 ggt acc atc aat gtc cac gac gtg gag aca cag ttc aat cag tat aaa       447
Gly Thr Ile Asn Val His Asp Val Glu Thr Gln Phe Asn Gln Tyr Lys
110                 115                 120                 125 acg gaa gca gcc tct cga tat aac ctg acg atc tca gac gtc agc gtg       495
Thr Glu Ala Ala Ser Arg Tyr Asn Leu Thr Ile Ser Asp Val Ser Val
                130                 135                 140 agt gat gtg cca ttt cct ttc tct gcc cag tct ggg gct ggg gtg cca       543
Ser Asp Val Pro Phe Pro Phe Ser Ala Gln Ser Gly Ala Gly Val Pro
            145                 150                 155 ggc tgg ggc atc gcg ctg ctg gtg ctg gtc tgt gtt ctg gtt gcg ctg       591
Gly Trp Gly Ile Ala Leu Leu Val Leu Val Cys Val Leu Val Ala Leu
```

```
Gly Trp Gly Ile Ala Leu Leu Val Leu Val Cys Val Leu Val Ala Leu
                160                 165                 170 gcc att gtc tat ctc att gcc ttg gct gtc tgt cag tgc cgc cga aag    639
Ala Ile Val Tyr Leu Ile Ala Leu Ala Val Cys Gln Cys Arg Arg Lys
        175                 180                 185 aac tac ggg cag ctg gac atc ttt cca gcc cgg gat acc tac cat cct    687
Asn Tyr Gly Gln Leu Asp Ile Phe Pro Ala Arg Asp Thr Tyr His Pro
190                 195                 200                 205 atg agc gag tac ccc acc tac cac acc cat ggg cgc tat gtg ccc cct    735
Met Ser Glu Tyr Pro Thr Tyr His Thr His Gly Arg Tyr Val Pro Pro
                210                 215                 220 agc agt acc gat cgt agc ccc tat gag aag gtt tct gca ggt aat ggt    783
Ser Ser Thr Asp Arg Ser Pro Tyr Glu Lys Val Ser Ala Gly Asn Gly
            225                 230                 235 ggc agc agc ctc tct tac aca aac cca gca gtg gca gcc act tct gcc    831
Gly Ser Ser Leu Ser Tyr Thr Asn Pro Ala Val Ala Ala Thr Ser Ala
        240                 245                 250 aac ttg tag gggcacgtcg cccgctgagc tgagtggcca gccagtgcca              880
Asn Leu
    255 ttccactcca ctcaggttct tcagggccag agccctgca ccctgtttgg gctggtgagc    940 tgggagttca ggtgggctgc tcacagcctc cttcagaggc cccaccaatt tctcggacac   1000 ttctcagtgt gtgaagctc atgtgggccc tgagggctc atgcctggga agtgttgtgg     1060 tgggggctcc caggaggact ggcccagaga gccctgagat agcgggatc ctgaactgga    1120 ctgaataaaa cgtggtctcc cactgcgcca aaaaaaaaaa aaaaaa                  1166

<210> SEQ ID NO 8
<211> LENGTH: 255
<212> TYPE: PRT
<213> ORGANISM: Homo sapiens

<400> SEQUENCE: 8

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Phe Asn Ser Ser Leu Glu Asp Pro Ser Thr Asp
    50                  55                  60

Tyr Tyr Gln Glu Leu Gln Arg Asp Ile Ser Glu Met Phe Leu Gln Ile
65                  70                  75                  80

Tyr Lys Gln Gly Gly Phe Leu Gly Leu Ser Asn Ile Lys Phe Arg Pro
                85                  90                  95

Gly Ser Val Val Val Gln Leu Thr Leu Ala Phe Arg Glu Gly Thr Ile
            100                 105                 110

Asn Val His Asp Val Glu Thr Gln Phe Asn Gln Tyr Lys Thr Glu Ala
        115                 120                 125

Ala Ser Arg Tyr Asn Leu Thr Ile Ser Asp Val Ser Val Ser Asp Val
    130                 135                 140

Pro Phe Pro Phe Ser Ala Gln Ser Gly Ala Gly Val Pro Gly Trp Gly
145                 150                 155                 160

Ile Ala Leu Leu Val Leu Val Cys Val Leu Val Ala Leu Ala Ile Val
                165                 170                 175

Tyr Leu Ile Ala Leu Ala Val Cys Gln Cys Arg Arg Lys Asn Tyr Gly
```

```
                        180                 185                 190
Gln Leu Asp Ile Phe Pro Ala Arg Asp Thr Tyr His Pro Met Ser Glu
            195                 200                 205

Tyr Pro Thr Tyr His Thr His Gly Arg Tyr Val Pro Pro Ser Ser Thr
        210                 215                 220

Asp Arg Ser Pro Tyr Glu Lys Val Ser Ala Gly Asn Gly Gly Ser Ser
225                 230                 235                 240

Leu Ser Tyr Thr Asn Pro Ala Val Ala Ala Thr Ser Ala Asn Leu
                245                 250                 255

<210> SEQ ID NO 9
<211> LENGTH: 2235
<212> TYPE: DNA
<213> ORGANISM: Mus musculus
<220> FEATURE:
<221> NAME/KEY: CDS
<222> LOCATION: (69)..(1964)

<400> SEQUENCE: 9
ccacctcaca cacggagcgc cagccttgag tttgtttct agccccttcc cgcctgttca      60 ccaccacc atg acc ccg ggc att cgg gct cct ttc ttc ctg ctg cta ctt    110
         Met Thr Pro Gly Ile Arg Ala Pro Phe Phe Leu Leu Leu Leu
         1               5                  10 cta gca agt cta aaa ggt ttt ctt gcc ctt cca agt gag gaa aac agt    158
Leu Ala Ser Leu Lys Gly Phe Leu Ala Leu Pro Ser Glu Glu Asn Ser
15              20                  25                  30 gtc acc tca tct cag gac acc agc agt tcc tta gca tcg act acc act    206
Val Thr Ser Ser Gln Asp Thr Ser Ser Ser Leu Ala Ser Thr Thr Thr
                35                  40                  45 cca gtc cac agc agc aac tca gac cca gcc acc aga cct cca ggg gac    254
Pro Val His Ser Ser Asn Ser Asp Pro Ala Thr Arg Pro Pro Gly Asp
            50                  55                  60 tcc acc agc tct cca gtc cag agt agc acc tct tct cca gcc acc aga    302
Ser Thr Ser Ser Pro Val Gln Ser Ser Thr Ser Ser Pro Ala Thr Arg
        65                  70                  75 gct cct gaa gac tct acc agt act gca gtc ctc agt ggc acc tcc tcc    350
Ala Pro Glu Asp Ser Thr Ser Thr Ala Val Leu Ser Gly Thr Ser Ser
    80                  85                  90 cca gcc acc aca gct cca gtg aac tcc gcc agc tct cca gta gcc cat    398
Pro Ala Thr Thr Ala Pro Val Asn Ser Ala Ser Ser Pro Val Ala His
95                  100                 105                 110 ggt gac acc tct tcc cca gcc act agc ctt tca aaa gac tcc aac agc    446
Gly Asp Thr Ser Ser Pro Ala Thr Ser Leu Ser Lys Asp Ser Asn Ser
                115                 120                 125 tct cca gta gtc cac agt ggc acc tct tca gct ccg gcc acc aca gct    494
Ser Pro Val Val His Ser Gly Thr Ser Ser Ala Pro Ala Thr Thr Ala
            130                 135                 140 cca gtg gat tcc acc agc tct cca gta gtc cac ggt ggt acc tcg tcc    542
Pro Val Asp Ser Thr Ser Ser Pro Val Val His Gly Gly Thr Ser Ser
        145                 150                 155 cca gcc acc agc cct cca ggg gac tcc acc agc tct cca gac cat agt    590
Pro Ala Thr Ser Pro Pro Gly Asp Ser Thr Ser Ser Pro Asp His Ser
    160                 165                 170 agc acc tct tct cca gcc acc aga gct ccc gaa gac tct acc agt act    638
Ser Thr Ser Ser Pro Ala Thr Arg Ala Pro Glu Asp Ser Thr Ser Thr
175                 180                 185                 190 gca gtc ctc agt ggc acc tcc tcc cca gcc acc aca gct cca gtg gac    686
Ala Val Leu Ser Gly Thr Ser Ser Pro Ala Thr Thr Ala Pro Val Asp
                195                 200                 205
```

| | | |
|---|---|---|
| tcc acc agc tct cca gta gcc cat gat gac acc tct tcc cca gcc act<br>Ser Thr Ser Ser Pro Val Ala His Asp Asp Thr Ser Ser Pro Ala Thr<br>210 215 220 | | 734 |
| agc ctt tca gaa gac tcc gcc agc tct cca gta gcc cac ggt ggc acc<br>Ser Leu Ser Glu Asp Ser Ala Ser Ser Pro Val Ala His Gly Gly Thr<br>225 230 235 | | 782 |
| tct tct cca gcc acc agc cct cta agg gac tcc acc agt tct cca gtc<br>Ser Ser Pro Ala Thr Ser Pro Leu Arg Asp Ser Thr Ser Ser Pro Val<br>240 245 250 | | 830 |
| cac agt agt gcc tcc atc caa aac atc aag act aca tca gac tta gct<br>His Ser Ser Ala Ser Ile Gln Asn Ile Lys Thr Thr Ser Asp Leu Ala<br>255 260 265 270 | | 878 |
| agc act cca gac cac aat ggc acc tca gtc aca act acc agc tct gca<br>Ser Thr Pro Asp His Asn Gly Thr Ser Val Thr Thr Thr Ser Ser Ala<br>275 280 285 | | 926 |
| ctg ggc tca gcc acc agt cca gac cac agt ggt acc tca act aca act<br>Leu Gly Ser Ala Thr Ser Pro Asp His Ser Gly Thr Ser Thr Thr Thr<br>290 295 300 | | 974 |
| aac agc tct gaa tca gtc ttg gcc acc act cca gtt tac agt agc atg<br>Asn Ser Ser Glu Ser Val Leu Ala Thr Thr Pro Val Tyr Ser Ser Met<br>305 310 315 | | 1022 |
| cca ttc tct act acc aaa gtg acg tca ggc tca gct atc att cca gac<br>Pro Phe Ser Thr Thr Lys Val Thr Ser Gly Ser Ala Ile Ile Pro Asp<br>320 325 330 | | 1070 |
| cac aat ggc tcc tcg gtg cta cct acc agt tct gtg ttg ggc tca gct<br>His Asn Gly Ser Ser Val Leu Pro Thr Ser Ser Val Leu Gly Ser Ala<br>335 340 345 350 | | 1118 |
| acc agt cta gtc tat aat acc tct gca ata gct aca act cca gtc agc<br>Thr Ser Leu Val Tyr Asn Thr Ser Ala Ile Ala Thr Thr Pro Val Ser<br>355 360 365 | | 1166 |
| aat ggc act cag cct tca gtg cca agt caa tac cct gtt tct cct acc<br>Asn Gly Thr Gln Pro Ser Val Pro Ser Gln Tyr Pro Val Ser Pro Thr<br>370 375 380 | | 1214 |
| atg gcc acc acc tcc agc cac agc act att gcc agc agc tct tac tat<br>Met Ala Thr Thr Ser Ser His Ser Thr Ile Ala Ser Ser Ser Tyr Tyr<br>385 390 395 | | 1262 |
| agc aca gta cca ttt tct acc ttc tcc agt aac agt tca ccc cag ttg<br>Ser Thr Val Pro Phe Ser Thr Phe Ser Ser Asn Ser Ser Pro Gln Leu<br>400 405 410 | | 1310 |
| tct gtt ggg gtc tcc ttc ttc ttg tct ttt tac att caa aac cac<br>Ser Val Gly Val Ser Phe Phe Leu Ser Phe Tyr Ile Gln Asn His<br>415 420 425 430 | | 1358 |
| cca ttt aat tct tct ctg gaa gac ccc agc tcc aac tac tac caa gaa<br>Pro Phe Asn Ser Ser Leu Glu Asp Pro Ser Ser Asn Tyr Tyr Gln Glu<br>435 440 445 | | 1406 |
| ctg aag agg aac att tct gga ttg ttt ctg cag att ttt aac gga gat<br>Leu Lys Arg Asn Ile Ser Gly Leu Phe Leu Gln Ile Phe Asn Gly Asp<br>450 455 460 | | 1454 |
| ttt ctg ggg atc tct agc atc aag ttc agg tca ggc tcc gtg gtg gta<br>Phe Leu Gly Ile Ser Ser Ile Lys Phe Arg Ser Gly Ser Val Val Val<br>465 470 475 | | 1502 |
| gaa tcg act gtg gtt ttc cgg gag ggt act ttt agt gcc tct gac gtg<br>Glu Ser Thr Val Val Phe Arg Glu Gly Thr Phe Ser Ala Ser Asp Val<br>480 485 490 | | 1550 |
| aag tca cag ctt ata cag cat aag aag gag gca gat gac tat aat ctg<br>Lys Ser Gln Leu Ile Gln His Lys Lys Glu Ala Asp Asp Tyr Asn Leu<br>495 500 505 510 | | 1598 |
| act att tca gaa gtc aaa gtg aat gag atg cag ttc cct ccc tct gcc<br>Thr Ile Ser Glu Val Lys Val Asn Glu Met Gln Phe Pro Pro Ser Ala<br>515 520 525 | | 1646 |

```
cag tcc cgg ccg ggg gta cca ggc tgg ggc att gcc ctg ctg gtg ctg      1694
Gln Ser Arg Pro Gly Val Pro Gly Trp Gly Ile Ala Leu Leu Val Leu
            530                 535                 540 gtc tgt att ttg gtt gct ttg gct atc gtc tat ttc ctt gcc ctg gca      1742
Val Cys Ile Leu Val Ala Leu Ala Ile Val Tyr Phe Leu Ala Leu Ala
        545                 550                 555 gtg tgc cag tgc cgc cga aag agc tat ggg cag ctg gac atc ttt cca      1790
Val Cys Gln Cys Arg Arg Lys Ser Tyr Gly Gln Leu Asp Ile Phe Pro
    560                 565                 570 acc cag gac acc tac cat cct atg agt gaa tac cct acc tac cac act      1838
Thr Gln Asp Thr Tyr His Pro Met Ser Glu Tyr Pro Thr Tyr His Thr
575                 580                 585                 590 cac gga cgc tac gtg ccc cct ggc agt acc aag cgt agc ccc tat gag      1886
His Gly Arg Tyr Val Pro Pro Gly Ser Thr Lys Arg Ser Pro Tyr Glu
                595                 600                 605 gag gtt tcg gca ggt aat ggc agt agc agt ctc tct tat acc aac cca      1934
Glu Val Ser Ala Gly Asn Gly Ser Ser Ser Leu Ser Tyr Thr Asn Pro
            610                 615                 620 gct gtg gtg acc act tct gcc aac ttg tag gagcaagtca ccccacccac        1984
Ala Val Val Thr Thr Ser Ala Asn Leu
        625                 630 ttggggcagc tttggcggtc tgctccctca gtggtcactg ccagacccct gcactctgat   2044
ctgggctggt gagccaggac ttctggtagg ctgttcatgc cctttgtcaa gcgcctcaac   2104
tacgtaagcc tggtgaagcc cagccctgcc ctggggaca ctggggcagt tagtggtggc    2164
tctcagaagg actggcctgg aaaactggag acagggatgg gaacccaaac atagctgaat   2224
aaaagatggc c                                                        2235

<210> SEQ ID NO 10
<211> LENGTH: 631
<212> TYPE: PRT
<213> ORGANISM: Mus musculus

<400> SEQUENCE: 10

Met Thr Pro Gly Ile Arg Ala Pro Phe Phe Leu Leu Leu Leu Leu Ala
1               5                   10                  15

Ser Leu Lys Gly Phe Leu Ala Leu Pro Ser Glu Glu Asn Ser Val Thr
            20                  25                  30

Ser Ser Gln Asp Thr Ser Ser Ser Leu Ala Ser Thr Thr Thr Pro Val
        35                  40                  45

His Ser Ser Asn Ser Asp Pro Ala Thr Arg Pro Pro Gly Asp Ser Thr
    50                  55                  60

Ser Ser Pro Val Gln Ser Ser Thr Ser Ser Pro Ala Thr Arg Ala Pro
65                  70                  75                  80

Glu Asp Ser Thr Ser Thr Ala Val Leu Ser Gly Thr Ser Ser Pro Ala
                85                  90                  95

Thr Thr Ala Pro Val Asn Ser Ala Ser Ser Pro Val Ala His Gly Asp
            100                 105                 110

Thr Ser Ser Pro Ala Thr Ser Leu Ser Lys Asp Ser Asn Ser Ser Pro
        115                 120                 125

Val Val His Ser Gly Thr Ser Ala Pro Ala Thr Thr Ala Pro Val
    130                 135                 140

Asp Ser Thr Ser Ser Pro Val Val His Gly Gly Thr Ser Ser Pro Ala
145                 150                 155                 160

Thr Ser Pro Pro Gly Asp Ser Ser Ser Pro Asp His Ser Ser Thr
                165                 170                 175
```

```
Ser Ser Pro Ala Thr Arg Ala Pro Glu Asp Ser Thr Ser Thr Ala Val
            180                 185                 190

Leu Ser Gly Thr Ser Ser Pro Ala Thr Thr Ala Pro Val Asp Ser Thr
        195                 200                 205

Ser Ser Pro Val Ala His Asp Asp Thr Ser Ser Pro Ala Thr Ser Leu
    210                 215                 220

Ser Glu Asp Ser Ala Ser Ser Pro Val Ala His Gly Gly Thr Ser Ser
225                 230                 235                 240

Pro Ala Thr Ser Pro Leu Arg Asp Ser Thr Ser Ser Pro Val His Ser
                245                 250                 255

Ser Ala Ser Ile Gln Asn Ile Lys Thr Thr Ser Asp Leu Ala Ser Thr
        260                 265                 270

Pro Asp His Asn Gly Thr Ser Val Thr Thr Thr Ser Ser Ala Leu Gly
            275                 280                 285

Ser Ala Thr Ser Pro Asp His Ser Gly Thr Ser Thr Thr Thr Asn Ser
        290                 295                 300

Ser Glu Ser Val Leu Ala Thr Thr Pro Val Tyr Ser Ser Met Pro Phe
305                 310                 315                 320

Ser Thr Thr Lys Val Thr Ser Gly Ser Ala Ile Ile Pro Asp His Asn
                325                 330                 335

Gly Ser Ser Val Leu Pro Thr Ser Ser Val Leu Gly Ser Ala Thr Ser
            340                 345                 350

Leu Val Tyr Asn Thr Ser Ala Ile Ala Thr Thr Pro Val Ser Asn Gly
        355                 360                 365

Thr Gln Pro Ser Val Pro Ser Gln Tyr Pro Val Ser Pro Thr Met Ala
    370                 375                 380

Thr Thr Ser Ser His Ser Thr Ile Ala Ser Ser Ser Tyr Tyr Ser Thr
385                 390                 395                 400

Val Pro Phe Ser Thr Phe Ser Ser Asn Ser Ser Pro Gln Leu Ser Val
                405                 410                 415

Gly Val Ser Phe Phe Phe Leu Ser Phe Tyr Ile Gln Asn His Pro Phe
            420                 425                 430

Asn Ser Ser Leu Glu Asp Pro Ser Ser Asn Tyr Tyr Gln Glu Leu Lys
        435                 440                 445

Arg Asn Ile Ser Gly Leu Phe Leu Gln Ile Phe Asn Gly Asp Phe Leu
    450                 455                 460

Gly Ile Ser Ser Ile Lys Phe Arg Ser Gly Ser Val Val Val Glu Ser
465                 470                 475                 480

Thr Val Val Phe Arg Glu Gly Thr Phe Ser Ala Ser Asp Val Lys Ser
                485                 490                 495

Gln Leu Ile Gln His Lys Lys Glu Ala Asp Asp Tyr Asn Leu Thr Ile
            500                 505                 510

Ser Glu Val Lys Val Asn Glu Met Gln Phe Pro Pro Ser Ala Gln Ser
        515                 520                 525

Arg Pro Gly Val Pro Gly Trp Gly Ile Ala Leu Leu Val Leu Val Cys
    530                 535                 540

Ile Leu Val Ala Leu Ala Ile Val Tyr Phe Leu Ala Leu Ala Val Cys
545                 550                 555                 560

Gln Cys Arg Arg Lys Ser Tyr Gly Gln Leu Asp Ile Phe Pro Thr Gln
                565                 570                 575

Asp Thr Tyr His Pro Met Ser Glu Tyr Pro Thr Tyr His Thr His Gly
            580                 585                 590
```

```
Arg Tyr Val Pro Pro Gly Ser Thr Lys Arg Ser Pro Tyr Glu Glu Val
            595                 600                 605

Ser Ala Gly Asn Gly Ser Ser Ser Leu Ser Tyr Thr Asn Pro Ala Val
    610                 615                 620

Val Thr Thr Ser Ala Asn Leu
625                 630

<210> SEQ ID NO 11
<211> LENGTH: 1255
<212> TYPE: PRT
<213> ORGANISM: Homo sapiens

<400> SEQUENCE: 11

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270

Pro Pro Ala His Gly Val Thr Ser Ala Pro Asp Thr Arg Pro Ala Pro
        275                 280                 285

Gly Ser Thr Ala Pro Pro Ala His Gly Val Thr Ser Ala Pro Asp Thr
    290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335
```

-continued

Gly Val Thr Ser Ala Pro Asp Thr Arg Pro Ala Pro Gly Ser Thr Ala
                340                 345                 350

Pro Pro Ala His Gly Val Thr Ser Ala Pro Asp Thr Arg Pro Ala Pro
            355                 360                 365

Gly Ser Thr Ala Pro Pro Ala His Gly Val Thr Ser Ala Pro Asp Thr
        370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
        435                 440                 445

Gly Ser Thr Ala Pro Pro Ala His Gly Val Thr Ser Ala Pro Asp Thr
    450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
        515                 520                 525

Gly Ser Thr Ala Pro Pro Ala His Gly Val Thr Ser Ala Pro Asp Thr
    530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
        595                 600                 605

Gly Ser Thr Ala Pro Pro Ala His Gly Val Thr Ser Ala Pro Asp Thr
    610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
        675                 680                 685

Gly Ser Thr Ala Pro Pro Ala His Gly Val Thr Ser Ala Pro Asp Thr
    690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
                725                 730                 735

Gly Val Thr Ser Ala Pro Asp Thr Arg Pro Ala Pro Gly Ser Thr Ala
            740                 745                 750

```
Pro Pro Ala His Gly Val Thr Ser Ala Pro Asp Thr Arg Pro Ala Pro
        755                 760                 765

Gly Ser Thr Ala Pro Pro Ala His Gly Val Thr Ser Ala Pro Asp Thr
770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
                805                 810                 815

Gly Val Thr Ser Ala Pro Asp Thr Arg Pro Ala Pro Gly Ser Thr Ala
            820                 825                 830

Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
                885                 890                 895

Gly Val Thr Ser Ala Pro Asp Thr Arg Pro Ala Pro Gly Ser Thr Ala
            900                 905                 910

Pro Pro Ala His Gly Val Thr Ser Ala Pro Asp Thr Arg Pro Ala Pro
        915                 920                 925

Gly Ser Thr Ala Pro Pro Ala His Gly Val Thr Ser Ala Pro Asp Asn
930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
                995                 1000                1005

Ser Thr Lys Thr Asp Ala Ser Ser Thr His His Ser Ser Val Pro
    1010                1015                1020

Pro Leu Thr Ser Ser Asn His Ser Thr Ser Pro Gln Leu Ser Thr
    1025                1030                1035

Gly Val Ser Phe Phe Phe Leu Ser Phe His Ile Ser Asn Leu Gln
    1040                1045                1050

Phe Asn Ser Ser Leu Glu Asp Pro Ser Thr Asp Tyr Tyr Gln Glu
    1055                1060                1065

Leu Gln Arg Asp Ile Ser Glu Met Phe Leu Gln Ile Tyr Lys Gln
    1070                1075                1080

Gly Gly Phe Leu Gly Leu Ser Asn Ile Lys Phe Arg Pro Gly Ser
    1085                1090                1095

Val Val Val Gln Leu Thr Leu Ala Phe Arg Glu Gly Thr Ile Asn
    1100                1105                1110

Val His Asp Val Glu Thr Gln Phe Asn Gln Tyr Lys Thr Glu Ala
    1115                1120                1125

Ala Ser Arg Tyr Asn Leu Thr Ile Ser Asp Val Ser Val Ser Asp
    1130                1135                1140

Val Pro Phe Pro Phe Ser Ala Gln Ser Gly Ala Gly Val Pro Gly
    1145                1150                1155

Trp Gly Ile Ala Leu Leu Val Leu Val Cys Val Leu Val Ala Leu
```

```
                1160                1165                1170

Ala Ile Val Tyr Leu Ile Ala  Leu Ala Val Cys Gln  Cys Arg Arg
    1175                1180                1185

Lys Asn Tyr Gly Gln Leu Asp  Ile Phe Pro Ala Arg  Asp Thr Tyr
    1190                1195                1200

His Pro Met Ser Glu Tyr Pro  Thr Tyr His Thr His  Gly Arg Tyr
    1205                1210                1215

Val Pro Pro Ser Ser Thr Asp  Arg Ser Pro Tyr Glu  Lys Val Ser
    1220                1225                1230

Ala Gly Asn Gly Gly Ser Ser  Leu Ser Tyr Thr Asn  Pro Ala Val
    1235                1240                1245

Ala Ala  Thr Ser Ala Asn Leu
    1250                1255

<210> SEQ ID NO 12
<211> LENGTH: 20
<212> TYPE: PRT
<213> ORGANISM: Homo sapiens
<220> FEATURE:
<221> NAME/KEY: VARIANT
<222> LOCATION: (9)..(9)
<223> OTHER INFORMATION: X= P, A, Q or T
<220> FEATURE:
<221> NAME/KEY: VARIANT
<222> LOCATION: (18)..(18)
<223> OTHER INFORMATION: X= D or E
<220> FEATURE:
<221> NAME/KEY: VARIANT
<222> LOCATION: (19)..(19)
<223> OTHER INFORMATION: X= T or S

<400> SEQUENCE: 12

Pro Ala Pro Gly Ser Thr Ala Pro Xaa Ala His Gly Val Thr Ser Ala
1               5                   10                  15

Pro Xaa Xaa Arg
        20

<210> SEQ ID NO 13
<211> LENGTH: 711
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(711)

<400> SEQUENCE: 13 atg aca ccg ggc acc cag tct cct ttc ttc ctg ctg ctg ctc ctc aca      48
Met Thr Pro Gly Thr Gln Ser Pro Phe Phe Leu Leu Leu Leu Leu Thr
1               5                   10                  15 gtg ctt aca gct acc aca gcc cct aaa ccc gca aca gtt gtt gga tct      96
Val Leu Thr Ala Thr Thr Ala Pro Lys Pro Ala Thr Val Val Gly Ser
            20                  25                  30 gtg gtg gta caa ttg act ctg gcc ttc cga gaa ggt acc atc aat gtc     144
Val Val Val Gln Leu Thr Leu Ala Phe Arg Glu Gly Thr Ile Asn Val
        35                  40                  45 cac gac gtg gag aca cag ttc aat cag tat aaa acg gaa gca gcc tct     192
His Asp Val Glu Thr Gln Phe Asn Gln Tyr Lys Thr Glu Ala Ala Ser
    50                  55                  60 cga tat aac ctg acg atc tca gac gtc agc gtg agt gat gtg cca ttt     240
Arg Tyr Asn Leu Thr Ile Ser Asp Val Ser Val Ser Asp Val Pro Phe
65                  70                  75                  80
```

| | | | | | | | | | | | | | | | |
|---|---|---|---|---|---|---|---|---|---|---|---|---|---|---|---|
| cct | ttc | tct | gcc | cag | tct | ggg | gct | ggg | gcc | cac | ggt | gtc | acc | agc | gcc |
| Pro | Phe | Ser | Ala | Gln | Ser | Gly | Ala | Gly | Ala | His | Gly | Val | Thr | Ser | Ala |
| | | | | 85 | | | | | 90 | | | | | 95 | |

288 cct gac acc agg ccg gcc ccg ggc tcc acc gcg ccc cca gcc cat ggt
Pro Asp Thr Arg Pro Ala Pro Gly Ser Thr Ala Pro Pro Ala His Gly
            100                 105                 110

336 gtc acc tcg gcc ccg gag agc agg ccc gcc cct ggg agc acc gcc ccc
Val Thr Ser Ala Pro Glu Ser Arg Pro Ala Pro Gly Ser Thr Ala Pro
        115                 120                 125

384 cct gca gtg cca ggc tgg ggc atc gcg ctg ctg gtg ctg gtc tgt gtt
Pro Ala Val Pro Gly Trp Gly Ile Ala Leu Leu Val Leu Val Cys Val
    130                 135                 140

432 ctg gtt gcg ctg gcc att gtc tat ctc att gcc ttg gct gtc tgt cag
Leu Val Ala Leu Ala Ile Val Tyr Leu Ile Ala Leu Ala Val Cys Gln
145                 150                 155                 160

480 tgc cgc cga aag aac tac ggg cag ctg gac atc ttt cca gcc cgg gat
Cys Arg Arg Lys Asn Tyr Gly Gln Leu Asp Ile Phe Pro Ala Arg Asp
                165                 170                 175

528 acc tac cat cct atg agc gag tac ccc acc tac cac acc cat ggg cgc
Thr Tyr His Pro Met Ser Glu Tyr Pro Thr Tyr His Thr His Gly Arg
            180                 185                 190

576 tat gtg ccc cct agc agt acc gat cgt agc ccc tat gag aag gtt tct
Tyr Val Pro Pro Ser Ser Thr Asp Arg Ser Pro Tyr Glu Lys Val Ser
        195                 200                 205

624 gca ggt aat ggt ggc agc agc ctc tct tac aca aac cca gca gtg gca
Ala Gly Asn Gly Gly Ser Ser Leu Ser Tyr Thr Asn Pro Ala Val Ala
    210                 215                 220

672 gcc act tct gcc aac ttg cat cat cac cac cat cac tag
Ala Thr Ser Ala Asn Leu His His His His His His
225                 230                 235

711

<210> SEQ ID NO 14
<211> LENGTH: 236
<212> TYPE: PRT
<213> ORGANISM: Artificial
<220> FEATURE:
<223> OTHER INFORMATION: Synthetic Construct

<400> SEQUENCE: 14

Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Gly Ser
            20                  25                  30

Val Val Val Gln Leu Thr Leu Ala Phe Arg Glu Gly Thr Ile Asn Val
        35                  40                  45

His Asp Val Glu Thr Gln Phe Asn Gln Tyr Lys Thr Glu Ala Ala Ser
    50                  55                  60

Arg Tyr Asn Leu Thr Ile Ser Asp Val Ser Ser Asp Val Pro Phe
65                  70                  75                  80

Pro Phe Ser Ala Gln Ser Gly Ala Gly Ala His Gly Val Thr Ser Ala
                85                  90                  95

Pro Asp Thr Arg Pro Ala Pro Gly Ser Thr Ala Pro Pro Ala His Gly
            100                 105                 110

Val Thr Ser Ala Pro Glu Ser Arg Pro Ala Pro Gly Ser Thr Ala Pro
        115                 120                 125

Pro Ala Val Pro Gly Trp Gly Ile Ala Leu Leu Val Leu Val Cys Val
    130                 135                 140

Leu Val Ala Leu Ala Ile Val Tyr Leu Ile Ala Leu Ala Val Cys Gln
145                 150                 155                 160

```
Cys Arg Arg Lys Asn Tyr Gly Gln Leu Asp Ile Phe Pro Ala Arg Asp
                165                 170                 175

Thr Tyr His Pro Met Ser Glu Tyr Pro Thr Tyr His Thr His Gly Arg
            180                 185                 190

Tyr Val Pro Pro Ser Ser Thr Asp Arg Ser Pro Tyr Glu Lys Val Ser
        195                 200                 205

Ala Gly Asn Gly Gly Ser Ser Leu Ser Tyr Thr Asn Pro Ala Val Ala
    210                 215                 220

Ala Thr Ser Ala Asn Leu His His His His His His
225                 230                 235

<210> SEQ ID NO 15
<211> LENGTH: 200
<212> TYPE: PRT
<213> ORGANISM: Artificial
<220> FEATURE:
<223> OTHER INFORMATION: Synthetic Construct

<400> SEQUENCE: 15

Gly Ser Val Val Gln Leu Thr Leu Ala Phe Arg Glu Gly Thr Ile
1               5                   10                  15

Asn Val His Asp Val Glu Thr Gln Phe Asn Gln Tyr Lys Thr Glu Ala
                20                  25                  30

Ala Ser Arg Tyr Asn Leu Thr Ile Ser Asp Val Ser Val Ser Asp Val
            35                  40                  45

Pro Phe Pro Phe Ser Ala Gln Ser Gly Ala Gly Ala His Gly Val Thr
        50                  55                  60

Ser Ala Pro Asp Thr Arg Pro Ala Pro Gly Ser Thr Ala Pro Pro Ala
65                  70                  75                  80

His Gly Val Thr Ser Ala Pro Glu Ser Arg Pro Ala Pro Gly Ser Thr
                85                  90                  95

Ala Pro Pro Ala Val Pro Gly Trp Gly Ile Ala Leu Leu Val Leu Val
            100                 105                 110

Cys Val Leu Val Ala Leu Ala Ile Val Tyr Leu Ile Ala Leu Ala Val
            115                 120                 125

Cys Gln Cys Arg Arg Lys Asn Tyr Gly Gln Leu Asp Ile Phe Pro Ala
            130                 135                 140

Arg Asp Thr Tyr His Pro Met Ser Glu Tyr Pro Thr Tyr His Thr His
145                 150                 155                 160

Gly Arg Tyr Val Pro Pro Ser Ser Thr Asp Arg Ser Pro Tyr Glu Lys
                165                 170                 175

Val Ser Ala Gly Asn Gly Gly Ser Ser Leu Ser Tyr Thr Asn Pro Ala
            180                 185                 190

Val Ala Ala Thr Ser Ala Asn Leu
            195                 200

<210> SEQ ID NO 16
<211> LENGTH: 687
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(687)

<400> SEQUENCE: 16 atg gcc gat gaa gct ccg tgt cag tgc cgc cga aag aac tac ggg cag      48
```

```
Met Ala Asp Glu Ala Pro Cys Gln Cys Arg Lys Asn Tyr Gly Gln
1               5                   10                  15 ctg gac atc ttt cca gcc cgg gat acc tac cat cct atg agc gag tac      96
Leu Asp Ile Phe Pro Ala Arg Asp Thr Tyr His Pro Met Ser Glu Tyr
            20                  25                  30 ccc acc tac cac acc cat ggg cgc tat gtg ccc cct agc agt acc gat     144
Pro Thr Tyr His Thr His Gly Arg Tyr Val Pro Pro Ser Ser Thr Asp
                35                  40                  45 cgt agc ccc tat gag aag gtt tct gca ggt aat ggt ggc agc agc ctc     192
Arg Ser Pro Tyr Glu Lys Val Ser Ala Gly Asn Gly Gly Ser Ser Leu
        50                  55                  60 tct tac aca aac cca gca gtg gca gcc act tct gcc aac ttg tgc caa     240
Ser Tyr Thr Asn Pro Ala Val Ala Ala Thr Ser Ala Asn Leu Cys Gln
65                  70                  75                  80 tgc aga aga aaa aat tat ggt caa ctt gac att ttt cct gca aga gat     288
Cys Arg Arg Lys Asn Tyr Gly Gln Leu Asp Ile Phe Pro Ala Arg Asp
                85                  90                  95 aca tat cat cca atg agt gaa tat cca act tat cac act cat ggc aga     336
Thr Tyr His Pro Met Ser Glu Tyr Pro Thr Tyr His Thr His Gly Arg
            100                 105                 110 tat gtc cca cca tcg tct aca gat aga tcg cca tac gaa aaa gta tcg     384
Tyr Val Pro Pro Ser Ser Thr Asp Arg Ser Pro Tyr Glu Lys Val Ser
                115                 120                 125 gct gga aat gga ggt agt tca ttg tca tac act aat cct gca gtc gct     432
Ala Gly Asn Gly Gly Ser Ser Leu Ser Tyr Thr Asn Pro Ala Val Ala
        130                 135                 140 gct acg tcc gct aat cta tgt caa tgt cgt agg aaa aac tac ggt caa     480
Ala Thr Ser Ala Asn Leu Cys Gln Cys Arg Arg Lys Asn Tyr Gly Gln
145                 150                 155                 160 ttg gat ata ttc cca gcc agg gac act tat cat cct atg tcc gaa tac     528
Leu Asp Ile Phe Pro Ala Arg Asp Thr Tyr His Pro Met Ser Glu Tyr
                165                 170                 175 cca acg tac cat aca cat ggc agg tat gtt cct cct tct tca act gat     576
Pro Thr Tyr His Thr His Gly Arg Tyr Val Pro Pro Ser Ser Thr Asp
            180                 185                 190 aga tcc ccg tat gaa aag gta tca gct gga aac ggt gga agt tcc tta     624
Arg Ser Pro Tyr Glu Lys Val Ser Ala Gly Asn Gly Gly Ser Ser Leu
        195                 200                 205 tca tat aca aat ccg gct gtt gcg gcg aca tct gca aat tta cat cat     672
Ser Tyr Thr Asn Pro Ala Val Ala Ala Thr Ser Ala Asn Leu His His
210                 215                 220 cac cac cat cac tga                                                  687
His His His His
225

<210> SEQ ID NO 17
<211> LENGTH: 228
<212> TYPE: PRT
<213> ORGANISM: Artificial
<220> FEATURE:
<223> OTHER INFORMATION: Synthetic Construct

<400> SEQUENCE: 17

Met Ala Asp Glu Ala Pro Cys Gln Cys Arg Lys Asn Tyr Gly Gln
1               5                   10                  15

Leu Asp Ile Phe Pro Ala Arg Asp Thr Tyr His Pro Met Ser Glu Tyr
            20                  25                  30

Pro Thr Tyr His Thr His Gly Arg Tyr Val Pro Pro Ser Ser Thr Asp
                35                  40                  45

Arg Ser Pro Tyr Glu Lys Val Ser Ala Gly Asn Gly Gly Ser Ser Leu
```

```
                      50                  55                  60
Ser Tyr Thr Asn Pro Ala Val Ala Ala Thr Ser Ala Asn Leu Cys Gln
 65                  70                  75                  80

Cys Arg Arg Lys Asn Tyr Gly Gln Leu Asp Ile Phe Pro Ala Arg Asp
                 85                  90                  95

Thr Tyr His Pro Met Ser Glu Tyr Pro Thr Tyr His Thr His Gly Arg
            100                 105                 110

Tyr Val Pro Pro Ser Ser Thr Asp Arg Ser Pro Tyr Glu Lys Val Ser
        115                 120                 125

Ala Gly Asn Gly Gly Ser Ser Leu Ser Tyr Thr Asn Pro Ala Val Ala
    130                 135                 140

Ala Thr Ser Ala Asn Leu Cys Gln Cys Arg Arg Lys Asn Tyr Gly Gln
145                 150                 155                 160

Leu Asp Ile Phe Pro Ala Arg Asp Thr Tyr His Pro Met Ser Glu Tyr
                165                 170                 175

Pro Thr Tyr His Thr His Gly Arg Tyr Val Pro Pro Ser Ser Thr Asp
            180                 185                 190

Arg Ser Pro Tyr Glu Lys Val Ser Ala Gly Asn Gly Gly Ser Ser Leu
        195                 200                 205

Ser Tyr Thr Asn Pro Ala Val Ala Ala Thr Ser Ala Asn Leu His His
    210                 215                 220

His His His His
225

<210> SEQ ID NO 18
<211> LENGTH: 216
<212> TYPE: PRT
<213> ORGANISM: Artificial
<220> FEATURE:
<223> OTHER INFORMATION: Synthetic Construct

<400> SEQUENCE: 18

Cys Gln Cys Arg Arg Lys Asn Tyr Gly Gln Leu Asp Ile Phe Pro Ala
  1               5                  10                  15

Arg Asp Thr Tyr His Pro Met Ser Glu Tyr Pro Thr Tyr His Thr His
             20                  25                  30

Gly Arg Tyr Val Pro Pro Ser Ser Thr Asp Arg Ser Pro Tyr Glu Lys
         35                  40                  45

Val Ser Ala Gly Asn Gly Gly Ser Ser Leu Ser Tyr Thr Asn Pro Ala
 50                  55                  60

Val Ala Thr Ser Ala Asn Leu Cys Gln Cys Arg Arg Lys Asn Tyr
 65                  70                  75                  80

Gly Gln Leu Asp Ile Phe Pro Ala Arg Asp Thr Tyr His Pro Met Ser
             85                  90                  95

Glu Tyr Pro Thr Tyr His Thr His Gly Arg Tyr Val Pro Pro Ser Ser
        100                 105                 110

Thr Asp Arg Ser Pro Tyr Glu Lys Val Ser Ala Gly Asn Gly Gly Ser
    115                 120                 125

Ser Leu Ser Tyr Thr Asn Pro Ala Val Ala Ala Thr Ser Ala Asn Leu
    130                 135                 140

Cys Gln Cys Arg Arg Lys Asn Tyr Gly Gln Leu Asp Ile Phe Pro Ala
145                 150                 155                 160

Arg Asp Thr Tyr His Pro Met Ser Glu Tyr Pro Thr Tyr His Thr His
                165                 170                 175

Gly Arg Tyr Val Pro Pro Ser Ser Thr Asp Arg Ser Pro Tyr Glu Lys
```

```
                180             185             190
Val Ser Ala Gly Asn Gly Gly Ser Ser Leu Ser Tyr Thr Asn Pro Ala
            195             200             205

Val Ala Ala Thr Ser Ala Asn Leu
    210             215

<210> SEQ ID NO 19
<211> LENGTH: 89
<212> TYPE: PRT
<213> ORGANISM: Saccharomyces cerevisiae

<400> SEQUENCE: 19

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala
                85

<210> SEQ ID NO 20
<211> LENGTH: 89
<212> TYPE: PRT
<213> ORGANISM: Saccharomyces cerevisiae

<400> SEQUENCE: 20

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala
                85

<210> SEQ ID NO 21
<211> LENGTH: 6
<212> TYPE: PRT
<213> ORGANISM: Artificial
<220> FEATURE:
<223> OTHER INFORMATION: Synthetic Peptide

<400> SEQUENCE: 21

Met Ala Asp Glu Ala Pro
1               5

<210> SEQ ID NO 22
<211> LENGTH: 779
<212> TYPE: DNA
<213> ORGANISM: Artificial
<220> FEATURE:
```

<223> OTHER INFORMATION: Synthetic Construct
<220> FEATURE:
<221> NAME/KEY: CDS
<222> LOCATION: (13)..(771)

<400> SEQUENCE: 22

```
gaattcgcca cc atg aca cca ggg aca caa agc cca ttt ttc cta ttg cta        51
              Met Thr Pro Gly Thr Gln Ser Pro Phe Phe Leu Leu Leu
              1               5                   10 ctc ttg act gtc tta acc gca acc act gct cca aaa cca gca act gtg          99
Leu Leu Thr Val Leu Thr Ala Thr Thr Ala Pro Lys Pro Ala Thr Val
    15                  20                  25 gtc ggt tca gtt gtg gtt cag tta aca ctt gct ttt aga gaa gga aca         147
Val Gly Ser Val Val Val Gln Leu Thr Leu Ala Phe Arg Glu Gly Thr
30                  35                  40                  45 att aac gta cac gat gta gaa act caa ttc aat caa tac aag aca gaa         195
Ile Asn Val His Asp Val Glu Thr Gln Phe Asn Gln Tyr Lys Thr Glu
                50                  55                  60 gcg gcc agt aga tac aat ttg aca att tct gac gtt tct gtg tct gac         243
Ala Ala Ser Arg Tyr Asn Leu Thr Ile Ser Asp Val Ser Val Ser Asp
            65                  70                  75 gtg cca ttt cca ttc tcc gct caa tca ggt gcc ggt gca cat ggc gta         291
Val Pro Phe Pro Phe Ser Ala Gln Ser Gly Ala Gly Ala His Gly Val
        80                  85                  90 acg tcc tac ctg gat aca aga cct gca cca gta tac ctc gca cct cct         339
Thr Ser Tyr Leu Asp Thr Arg Pro Ala Pro Val Tyr Leu Ala Pro Pro
    95                  100                 105 gct cat gga gtt aca tct gcc cct gag tcc agg cca gct cct ggt tct         387
Ala His Gly Val Thr Ser Ala Pro Glu Ser Arg Pro Ala Pro Gly Ser
110                 115                 120                 125 acc gca cca cct gct gtt cca ggt tgg ggc atc gcc ttg ctg gtc tta         435
Thr Ala Pro Pro Ala Val Pro Gly Trp Gly Ile Ala Leu Leu Val Leu
                130                 135                 140 gtt tgt gtc ctg gtg tac ttg gct ata gtc tac tta atc gca cta gct         483
Val Cys Val Leu Val Tyr Leu Ala Ile Val Tyr Leu Ile Ala Leu Ala
            145                 150                 155 gta tgc cag gtt aga aga aag aac tac ggc caa ttg gat atc ttt cca         531
Val Cys Gln Val Arg Arg Lys Asn Tyr Gly Gln Leu Asp Ile Phe Pro
        160                 165                 170 gcg aga gat act tat cat cca atg tca gag tat cca act tat cat aca         579
Ala Arg Asp Thr Tyr His Pro Met Ser Glu Tyr Pro Thr Tyr His Thr
    175                 180                 185 cat gga cgt tat gtt cca cct tcc tct ctt ttt aga agt cct tac gaa         627
His Gly Arg Tyr Val Pro Pro Ser Ser Leu Phe Arg Ser Pro Tyr Glu
190                 195                 200                 205 aaa gtt tca gca ggt aat gga ggc tca tac ctt tca tac act aat cca         675
Lys Val Ser Ala Gly Asn Gly Gly Ser Tyr Leu Ser Tyr Thr Asn Pro
                210                 215                 220 gcc gtt gct gcg act tct gca aac ttg gaa cct gcc agt ggg agc gct         723
Ala Val Ala Ala Thr Ser Ala Asn Leu Glu Pro Ala Ser Gly Ser Ala
            225                 230                 235 gct tta tgg ggt caa gat gta acc tct cat cac cat cac cac cat tag         771
Ala Leu Trp Gly Gln Asp Val Thr Ser His His His His His His
        240                 245                 250 gcggccgc                                                                779
```

<210> SEQ ID NO 23
<211> LENGTH: 252
<212> TYPE: PRT
<213> ORGANISM: Artificial
<220> FEATURE:

-continued

<223> OTHER INFORMATION: Synthetic Construct

<400> SEQUENCE: 23

Met Thr Pro Gly Thr Gln Ser Pro Phe Phe Leu Leu Leu Leu Leu Thr
1               5                   10                  15

Val Leu Thr Ala Thr Thr Ala Pro Lys Pro Ala Thr Val Val Gly Ser
            20                  25                  30

Val Val Val Gln Leu Thr Leu Ala Phe Arg Glu Gly Thr Ile Asn Val
        35                  40                  45

His Asp Val Glu Thr Gln Phe Asn Gln Tyr Lys Thr Glu Ala Ala Ser
    50                  55                  60

Arg Tyr Asn Leu Thr Ile Ser Asp Val Ser Val Ser Asp Val Pro Phe
65                  70                  75                  80

Pro Phe Ser Ala Gln Ser Gly Ala Gly Ala His Gly Val Thr Ser Tyr
                85                  90                  95

Leu Asp Thr Arg Pro Ala Pro Val Tyr Leu Ala Pro Pro Ala His Gly
            100                 105                 110

Val Thr Ser Ala Pro Glu Ser Arg Pro Ala Pro Gly Ser Thr Ala Pro
        115                 120                 125

Pro Ala Val Pro Gly Trp Gly Ile Ala Leu Leu Val Leu Val Cys Val
130                 135                 140

Leu Val Tyr Leu Ala Ile Val Tyr Leu Ile Ala Leu Ala Val Cys Gln
145                 150                 155                 160

Val Arg Arg Lys Asn Tyr Gly Gln Leu Asp Ile Phe Pro Ala Arg Asp
                165                 170                 175

Thr Tyr His Pro Met Ser Glu Tyr Pro Thr Tyr His Thr His Gly Arg
            180                 185                 190

Tyr Val Pro Pro Ser Ser Leu Phe Arg Ser Pro Tyr Glu Lys Val Ser
        195                 200                 205

Ala Gly Asn Gly Gly Ser Tyr Leu Ser Tyr Thr Asn Pro Ala Val Ala
    210                 215                 220

Ala Thr Ser Ala Asn Leu Glu Pro Ala Ser Gly Ser Ala Ala Leu Trp
225                 230                 235                 240

Gly Gln Asp Val Thr Ser His His His His His His
                245                 250

<210> SEQ ID NO 24
<211> LENGTH: 1727
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(1719)

<400> SEQUENCE: 24

```
atg aga ttt cct tca att ttt act gca gtt tta ttc gca gca tcc tcc        48
Met Arg Phe Pro Ser Ile Phe Thr Ala Val Leu Phe Ala Ala Ser Ser
1               5                   10                  15 gca tca gct gct cca gtc aac act aca aca gaa gat gaa acg gca caa        96
Ala Ser Ala Ala Pro Val Asn Thr Thr Thr Glu Asp Glu Thr Ala Gln
            20                  25                  30 att ccg gct gaa gct gtc atc ggt tac tta gat tta gaa ggg gat ttc       144
Ile Pro Ala Glu Ala Val Ile Gly Tyr Leu Asp Leu Glu Gly Asp Phe
        35                  40                  45 gat gtt gct gtt ttg cca ttt tcc aac agc aca aat aac ggg tta ttg       192
Asp Val Ala Val Leu Pro Phe Ser Asn Ser Thr Asn Asn Gly Leu Leu
```

```
                50                  55                  60
ttt ata aat act act att gcc agc att gct gct aaa gaa gaa ggg gta      240
Phe Ile Asn Thr Thr Ile Ala Ser Ile Ala Ala Lys Glu Glu Gly Val
 65                  70                  75                  80 tct cta gat aaa aga gag gct gaa gct act agt atg act cca ggt aca      288
Ser Leu Asp Lys Arg Glu Ala Glu Ala Thr Ser Met Thr Pro Gly Thr
                     85                  90                  95 caa tca cca ttc ttt ttg ttg cta ttg tta acc gtt ctg acc gtc gtt      336
Gln Ser Pro Phe Phe Leu Leu Leu Leu Leu Thr Val Leu Thr Val Val
                100                 105                 110 act gga tca ggt cac gcc tct agt acg cca gga ggt gaa aaa gag act      384
Thr Gly Ser Gly His Ala Ser Ser Thr Pro Gly Gly Glu Lys Glu Thr
                115                 120                 125 tct gcc aca caa aga tcc tct gtc cca tca tct act gag aaa aat gca      432
Ser Ala Thr Gln Arg Ser Ser Val Pro Ser Ser Thr Glu Lys Asn Ala
130                 135                 140 gtt tct atg aca tcc tca gta ttg tcc tca cat tcc cct ggt tct ggt      480
Val Ser Met Thr Ser Ser Val Leu Ser Ser His Ser Pro Gly Ser Gly
145                 150                 155                 160 tcc tct aca act cag gga caa gat gtg acg ttg gct cct gca acc gaa      528
Ser Ser Thr Thr Gln Gly Gln Asp Val Thr Leu Ala Pro Ala Thr Glu
                165                 170                 175 cca gcc tcc ggg agt gcg gct cta tgg ggg caa gat gtc aca tca gtc      576
Pro Ala Ser Gly Ser Ala Ala Leu Trp Gly Gln Asp Val Thr Ser Val
                180                 185                 190 cca gta aca aga cct gca tta gga tca aca act cca cct gct cac gat      624
Pro Val Thr Arg Pro Ala Leu Gly Ser Thr Thr Pro Pro Ala His Asp
                195                 200                 205 gta aca agc gca cca gat aac aag cct gca cct ggc tct acc gct cca      672
Val Thr Ser Ala Pro Asp Asn Lys Pro Ala Pro Gly Ser Thr Ala Pro
210                 215                 220 cct gcc cac ggc gta aca agt tat ttg gat aca aga cca gca cct gtt      720
Pro Ala His Gly Val Thr Ser Tyr Leu Asp Thr Arg Pro Ala Pro Val
225                 230                 235                 240 tac ttg gca cct cct gct cac ggt gtt aca tct gct cct gac aat aga      768
Tyr Leu Ala Pro Pro Ala His Gly Val Thr Ser Ala Pro Asp Asn Arg
                245                 250                 255 cca gct tta gga tct act gct cct cca gtg cat aac gta act tca gcc      816
Pro Ala Leu Gly Ser Thr Ala Pro Pro Val His Asn Val Thr Ser Ala
                260                 265                 270 tca ggc tcc gca tcc ggt tct gct tca aca ctt gtc cac aat gga act      864
Ser Gly Ser Ala Ser Gly Ser Ala Ser Thr Leu Val His Asn Gly Thr
                275                 280                 285 tct gct aga gca aca aca aca cca gcc tct aaa agt act cct ttc tct      912
Ser Ala Arg Ala Thr Thr Thr Pro Ala Ser Lys Ser Thr Pro Phe Ser
290                 295                 300 atc cca tct cat cat tct gat act cct aca act tta gct tca cac tca      960
Ile Pro Ser His His Ser Asp Thr Pro Thr Thr Leu Ala Ser His Ser
305                 310                 315                 320 act aaa aca gat gcc agt agt act cat cat tcc tct gta cca cct ctt     1008
Thr Lys Thr Asp Ala Ser Ser Thr His His Ser Ser Val Pro Pro Leu
                325                 330                 335 aca tct tct aat cat tca aca tca cca caa ctc tcc act ggt gtg agc     1056
Thr Ser Ser Asn His Ser Thr Ser Pro Gln Leu Ser Thr Gly Val Ser
                340                 345                 350 ttc ttc ttc ctc tct ttt cac att tca aac ctg caa ttc aac tct tcc     1104
Phe Phe Phe Leu Ser Phe His Ile Ser Asn Leu Gln Phe Asn Ser Ser
                355                 360                 365 cta gag gac cca tct acg gac tat tat caa gag ttg caa aga gat atc     1152
```

```
Leu Glu Asp Pro Ser Thr Asp Tyr Tyr Gln Glu Leu Gln Arg Asp Ile
    370             375                 380 agc gaa atg ttt cta cag atc tac aag caa ggt gga ttt ttg gga cta    1200
Ser Glu Met Phe Leu Gln Ile Tyr Lys Gln Gly Gly Phe Leu Gly Leu
385             390                 395                 400 tca aac ata aag ttt aga cca ggc agc gtt gtc gtc caa ctt acc tta    1248
Ser Asn Ile Lys Phe Arg Pro Gly Ser Val Val Val Gln Leu Thr Leu
            405                 410                 415 gct ttt aga gaa ggg act att aat gtt cat gat gtg gaa acc cag ttt    1296
Ala Phe Arg Glu Gly Thr Ile Asn Val His Asp Val Glu Thr Gln Phe
        420                 425                 430 aat caa tac aag aca gaa gca gct tca cga tac aat ttg aca att tcc    1344
Asn Gln Tyr Lys Thr Glu Ala Ala Ser Arg Tyr Asn Leu Thr Ile Ser
    435                 440                 445 gat gtt tct gtt tcc gac gta cct ttt cca ttc tct gcc caa agt ggt    1392
Asp Val Ser Val Ser Asp Val Pro Phe Pro Phe Ser Ala Gln Ser Gly
450             455                 460 gcg ggt gtt cca ggt tgg ggg att gct ctg tta gtg tta gtc tgt gtt    1440
Ala Gly Val Pro Gly Trp Gly Ile Ala Leu Leu Val Leu Val Cys Val
465             470                 475                 480 ctc gtt tac tta gct atc gta tac tta ata gcc cta gca gtt tgc cag    1488
Leu Val Tyr Leu Ala Ile Val Tyr Leu Ile Ala Leu Ala Val Cys Gln
            485                 490                 495 gtg aga agg aaa aac tat ggc caa ttg gat atc ttt cct gct aga gac    1536
Val Arg Arg Lys Asn Tyr Gly Gln Leu Asp Ile Phe Pro Ala Arg Asp
        500                 505                 510 act tac cat cca atg tct gaa tat cca acc tac cat aca cat ggt agg    1584
Thr Tyr His Pro Met Ser Glu Tyr Pro Thr Tyr His Thr His Gly Arg
    515                 520                 525 tac gtc cca cca tca agt ctt ttt cgt tca cca tac gaa aaa gtt agc    1632
Tyr Val Pro Pro Ser Ser Leu Phe Arg Ser Pro Tyr Glu Lys Val Ser
530             535                 540 gca ggt aat ggc ggc agt tac ctg tca tac act aac cca gcg gtt gct    1680
Ala Gly Asn Gly Gly Ser Tyr Leu Ser Tyr Thr Asn Pro Ala Val Ala
545             550                 555                 560 gcg gct agt gcc aat ctt cat cac cat cat cac cat taa gcggccgc      1727
Ala Ala Ser Ala Asn Leu His His His His His His
            565                 570

<210> SEQ ID NO 25
<211> LENGTH: 572
<212> TYPE: PRT
<213> ORGANISM: Artificial
<220> FEATURE:
<223> OTHER INFORMATION: Synthetic Construct

<400> SEQUENCE: 25

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Thr Ser Met Thr Pro Gly Thr
            85                  90                  95
```

-continued

Gln Ser Pro Phe Phe Leu Leu Leu Leu Thr Val Leu Thr Val Val
                100                 105                 110

Thr Gly Ser Gly His Ala Ser Ser Thr Pro Gly Gly Glu Lys Glu Thr
        115                 120                 125

Ser Ala Thr Gln Arg Ser Ser Val Pro Ser Ser Thr Glu Lys Asn Ala
    130                 135                 140

Val Ser Met Thr Ser Ser Val Leu Ser Ser His Ser Pro Gly Ser Gly
145                 150                 155                 160

Ser Ser Thr Thr Gln Gly Gln Asp Val Thr Leu Ala Pro Ala Thr Glu
                165                 170                 175

Pro Ala Ser Gly Ser Ala Ala Leu Trp Gly Gln Asp Val Thr Ser Val
            180                 185                 190

Pro Val Thr Arg Pro Ala Leu Gly Ser Thr Thr Pro Pro Ala His Asp
        195                 200                 205

Val Thr Ser Ala Pro Asp Asn Lys Pro Ala Pro Gly Ser Thr Ala Pro
210                 215                 220

Pro Ala His Gly Val Thr Ser Tyr Leu Asp Thr Arg Pro Ala Pro Val
225                 230                 235                 240

Tyr Leu Ala Pro Pro Ala His Gly Val Thr Ser Ala Pro Asp Asn Arg
                245                 250                 255

Pro Ala Leu Gly Ser Thr Ala Pro Pro Val His Asn Val Thr Ser Ala
            260                 265                 270

Ser Gly Ser Ala Ser Gly Ser Ala Ser Thr Leu Val His Asn Gly Thr
        275                 280                 285

Ser Ala Arg Ala Thr Thr Thr Pro Ala Ser Lys Ser Thr Pro Phe Ser
    290                 295                 300

Ile Pro Ser His His Ser Asp Thr Pro Thr Thr Leu Ala Ser His Ser
305                 310                 315                 320

Thr Lys Thr Asp Ala Ser Ser Thr His His Ser Ser Val Pro Pro Leu
                325                 330                 335

Thr Ser Ser Asn His Ser Thr Ser Pro Gln Leu Ser Thr Gly Val Ser
            340                 345                 350

Phe Phe Phe Leu Ser Phe His Ile Ser Asn Leu Gln Phe Asn Ser Ser
        355                 360                 365

Leu Glu Asp Pro Ser Thr Asp Tyr Tyr Gln Glu Leu Gln Arg Asp Ile
370                 375                 380

Ser Glu Met Phe Leu Gln Ile Tyr Lys Gln Gly Gly Phe Leu Gly Leu
385                 390                 395                 400

Ser Asn Ile Lys Phe Arg Pro Gly Ser Val Val Val Gln Leu Thr Leu
                405                 410                 415

Ala Phe Arg Glu Gly Thr Ile Asn Val His Asp Val Glu Thr Gln Phe
            420                 425                 430

Asn Gln Tyr Lys Thr Glu Ala Ala Ser Arg Tyr Asn Leu Thr Ile Ser
        435                 440                 445

Asp Val Ser Val Ser Asp Val Pro Phe Pro Phe Ser Ala Gln Ser Gly
    450                 455                 460

Ala Gly Val Pro Gly Trp Gly Ile Ala Leu Leu Val Leu Val Cys Val
465                 470                 475                 480

Leu Val Tyr Leu Ala Ile Val Tyr Leu Ile Ala Leu Ala Val Cys Gln
                485                 490                 495

Val Arg Arg Lys Asn Tyr Gly Gln Leu Asp Ile Phe Pro Ala Arg Asp
            500                 505                 510

```
Thr Tyr His Pro Met Ser Glu Tyr Pro Thr Tyr His Thr His Gly Arg
        515                 520                 525

Tyr Val Pro Pro Ser Ser Leu Phe Arg Ser Pro Tyr Glu Lys Val Ser
    530                 535                 540

Ala Gly Asn Gly Gly Ser Tyr Leu Ser Tyr Thr Asn Pro Ala Val Ala
545                 550                 555                 560

Ala Ala Ser Ala Asn Leu His His His His His His
                565             570
```

YEAST-MUC1 IMMUNOTHERAPEUTIC COMPOSITIONS AND USES THEREOF

CROSS-REFERENCE TO RELATED APPLICATIONS

This application is a continuation application of U.S. application Ser. No. 15/358,797, filed Nov. 22, 2016, now issued as U.S. Pat. No. 10,188,714, which is a divisional application of U.S. application Ser. No. 13/803,757, filed Mar. 14, 2013, now issued as U.S. Pat. No. 9,533,031, which claims the benefit of priority under 35 U.S.C. § 120 and is a continuation of PCT Application No. PCT/US12/51299, filed Aug. 17, 2012, which claims the benefit of priority under 35 U.S.C. § 119(e) to U.S. Provisional Patent Application No. 61/524,407, filed Aug. 17, 2011. The entire disclosure of each of U.S. application Ser. No. 15/358,797, U.S. application Ser. No. 13/803,757, PCT Application No. PCT/US12/51299 and U.S. Provisional Patent Application No. 61/524,407 is incorporated herein by reference.

GOVERNMENT RIGHTS

This invention was created in the performance of a Cooperative Research and Development Agreement with the National Institutes of Health, an Agency of the Department of Health and Human Services. The Government of the United States has certain rights in this invention.

STATEMENT REGARDING JOINT RESEARCH AGREEMENT

This invention was made by or on behalf of parties to a Cooperative Research and Development Agreement, executed May 8, 2008. The parties to the Cooperative Research and Development Agreement are: GlobeImmune, Inc. and the U.S. Department of Health and Human Services, as represented by National Cancer Institute, an Institute, Center or Division of the National Institutes of Health.

REFERENCE TO A SEQUENCE LISTING

This application contains a Sequence Listing submitted electronically as a text file by EFS-Web. The text file, named "3923-40-PCT_ST25", has a size in bytes of 89 KB, and was recorded on 16 Aug. 2012. The information contained in the text file is incorporated herein by reference in its entirety pursuant to 37 CFR § 1.52(e)(5).

FIELD OF THE INVENTION

The present invention generally relates to yeast-based immunotherapeutic compositions and methods for the prevention and/or treatment of cancers characterized by the expression or overexpression of mucin-1 (MUC1).

BACKGROUND OF THE INVENTION

Cancer is a leading cause of death worldwide, and the development of effective therapies for cancer continues to be one of the most active areas of research and clinical development. Although a variety of innovative approaches to treat and prevent cancers have been proposed, many cancers continue to have a high rate of mortality and may be difficult to treat or relatively unresponsive to conventional therapies.

A large number of human carcinomas and hematologic malignancies are characterized, at least in part, by aberrant overexpression of a protein known as mucin-1 (MUC1) whose normal function is to help protect epithelial cells from toxins, microorganisms and other types of external environment stresses (Kufe et al., *Hybridoma* 1984; 3:223-32). MUC1 is a heterodimeric protein formed from the noncovalent interaction of two subunits which are encoded by a single transcript and then processed into subunits post-translationally, known as MUC1-N and MUC1-C. MUC1 is normally found at the apical borders of secretory epithelial cells, and when the cells lose polarity in response to stress, a reversible process for normal cells, MUC1 can interact with molecules that usually localize at the basolateral borders. In addition, in response to stress environments, the MUC1-N subunit, a large protein containing a variable number of tandem repeats (VNTR) that are extensively glycosylated with O-linked glycans, can be shed. The other subunit of MUC1, known as MUC1-C, has an extracellular domain, a transmembrane domain and a cytoplasmic tail, and can bind to a ligand that is responsible for physically associating MUC1 with the epidermal growth factor receptor (EGFR) (Li et al., *J Biol Chem* 2001; 276:35239-42; Schroeder et al., *J Biol Chem* 2001; 276:13057-64) as well as other receptor tyrosine kinases, such as ErbB2-4,20 FGFR321 and PDGFR (Li et al., *Mol Cancer Res* 2003; 1:765-75; Ren et al., *Mol Cancer Res* 2006; 4:873-83; Singh et al., *Cancer Res* 2007; 67:5201-10). In addition, MUC1-C has been associated with a variety of signaling pathways that include ErbB receptors, c-Src, β-catenin, transcription factors (p53, ERα) and other effectors, such as Grb2/SOS (Pandey et al., *Cancer Res* 1995; 55:4000-3; Kinlough et al., *J Biol Chem* 2004; 279:53071-7).

In transformed epithelial cells, membrane polarity is irreversible and MUC1 expression is upregulated over the entire surface of carcinoma cells (Kufe et al., 1984, supra). MUC1 overexpression is associated with decreased MUC1-N O-glycosylation, and the high levels of MUC1-N at the cell surface sterically block cell-cell and cell-extracellular matrix interactions, which are associated with the malignant phenotype (Ligtenberg et al., *Cancer Res* 1992; 52:223-32; van de Wiel-van Kemenade et al., *J Immunol* 1993; 151:767-76; Wesseling et al., *Mol Biol Cell* 1996; 7:565-77). The MUC1-C subunit is now considered to be an oncoprotein, based on its involvement in diverse signaling pathways associated with tumorigenesis, and its overexpression has been shown to be involved in blocking induction of apoptosis in the response to DNA damage (Ren et al., *Cancer Cell* 2004; 5:163-75; Raina et al., *J Biol Chem* 2004; 279:20607-12), oxidative stress (Yin and Kufe, *J Biol Chem* 2003; 278:35458-64; Yin et al., *J Biol Chem* 2004; 279: 45721-7), and hypoxia (Yin et al., *J Biol Chem* 2007; 282:257-66), as well as conferring anchorage-independent growth and tumorigenicity (Li et al., *Oncogene* 2003; 22:6107-10; Huang et al., *Cancer Biol Ther* 2003; 2:702-6; Huang et al., *Cancer Res* 2005; 65:10413-22; Schroeder et al., *Oncogene* 2004; 23:5739-47).

As discussed above, data from various laboratories indicate that the MUC1-N (α subunit) plays a role in cancer by conferring cellular properties that allow immune evasion and potentially metastatic spread. The MUC1-C (β subunit) engages signaling pathways responsible for tumor initiation and progression. These dual functions of MUC1 may explain the differing roles this antigen appears to play in different cancer indications. For example, MUC1 appears to be an early marker in cancers such as breast cancer and colon cancer (e.g., see Kretschmer et al., *Mol Cancer.* 2011 Feb. 11; 10(1): 15; Mukhopadhyay et al., *Biochim Biophys Acta.* 2011 April; 1815(2):224-40; Saeki et al., *Gastroen-* terology. 2011 March; 140(3):892-902), while MUC1 is associated with epithelial-mesenchymal transition (EMT) pathways and metastatic spread in cancers such as pancreas cancer and esophageal cancer (e.g., see Xu et al., *Life Sci.* 2011 Jun. 6; 88(23-24):1063-9; Besmer et al., *Cancer Res.* 2011 Jul. 1; 71(13):4432-42; Roy et al., *Oncogene* 2011 Mar. 24; 30(12):1449-59; Ye et al., *Lab Invest.* 2011 May; 91(5): 778-87), and prevents terminal differentiation by reactive oxygen species in acute myeloid leukemia (AML) (e.g., see Yin et al., *Blood.* 2011 May 5; 117(18):4863-70; Fatrai et al., *Exp Hematol.* 2008 October; 36(10):1254-65), thereby allowing unlimited self renewal of these cancer cells.

Given the apparent role of MUC1 in the malignant phenotype of cancer cells, MUC1, and particularly MUC1-N, has been the focus of anti-cancer therapeutic approaches. Indeed, the majority of therapeutic approaches have targeted MUC1-N, the extracellular portion of the MUC1 heterodimer. However, such approaches targeting MUC1-N have not been successful in the clinic so far, possibly due to interference from MUC1-N that is shed from the cells. More recent studies have proposed targeting the MUC1-C subunit with antibodies against the extracellular domain, or with peptides, peptides conjugated with a carbohydrate polymer, small molecules, with preparations of tumor cells expressing MUC1, and with dendritic cell/tumor cell fusions. However, there are presently no approved cancer therapies that specifically target MUC1. Accordingly, there remains a need in the art for new products that effectively treat and/or prevent cancers associated with MUC1 expression or overexpression.

SUMMARY OF THE INVENTION

One embodiment of the invention relates to a yeast-MUC1 immunotherapeutic composition, comprising: (a) a yeast vehicle; and (b) a fusion protein expressed by the yeast vehicle and comprising at least one MUC1 antigen. In one aspect, the MUC1 antigen consists of, in order from N- to C-terminus, a MUC1 SEA/extracellular domain (ED), wherein the MUC1 SEA/ED domain comprises a MUC1 ED flanked at the N-terminus by one or more amino acids from the non-ED portion of the MUC1 SEA domain; at least two variable number of tandem repeat (VNTR) domains; a MUC1 transmembrane (TM) domain; and a MUC1 cytoplasmic domain (CD).

In one aspect, the antigen includes two VNTR domains. In one aspect, the VNTR domain has an amino acid sequence that is at least 95%, 96%, 97%, 98%, 99%, or 100% identical to positions 126-145 of SEQ ID NO:11; any consecutive 20 amino acids between positions 61 and 1020 of SEQ ID NO:11; any consecutive 20 amino acids between positions 126 and 965 of SEQ ID NO:11; SEQ ID NO:12; any consecutive 20 amino acids between positions 90 and 130 of SEQ ID NO:14; any consecutive 20 amino acids between positions 60 and 100 of SEQ ID NO:15; and a corresponding sequence from a different human MUC1 protein. In one aspect, the VNTR domain has an amino acid sequence that is at least 95%, 96%, 97%, 98%, 99%, or 100% identical to any consecutive 20 amino acids between positions 90 and 130 of SEQ ID NO:14 or any consecutive 20 amino acids between positions 60 and 100 of SEQ ID NO:15. In one aspect, the fusion protein has two VNTR domains, and the amino acid sequence of the two VNTR domains is positions 90 and 130 of SEQ ID NO:14 or positions 60 and 100 of SEQ ID NO:15.

In one aspect, the MUC1 ED has an amino acid sequence that is at least 95%, 96%, 97%, 98%, 99%, or 100% identical to an amino acid sequence selected from: positions 116-173 of SEQ ID NO:2; positions 107-164 of SEQ ID NO:4; positions 107-164 of SEQ ID NO:6; positions 98-155 of SEQ ID NO:8; positions 1098-1155 of SEQ ID NO:11; positions 32-89 of SEQ ID NO:14; positions 2-59 of SEQ ID NO:15; and a corresponding sequence from a different human MUC1 protein. In one aspect, the MUC1 ED has an amino acid sequence that is at least 95%, 96%, 97%, 98%, 99%, or 100% identical to positions 32-89 of SEQ ID NO:14 or positions 2-59 of SEQ ID NO:15. In one aspect, the MUC1 ED has an amino acid sequence of positions 32-89 of SEQ ID NO:14 or positions 2-59 of SEQ ID NO:15. In one aspect, the MUC1 SEA/ED has an amino acid sequence that is at least 95%, 96%, 97%, 98%, 99%, or 100% identical to an amino acid sequence selected from: positions 115-173 of SEQ ID NO:2; positions 106-164 of SEQ ID NO:4; positions 106-164 of SEQ ID NO:6; positions 97-155 of SEQ ID NO:8; positions 1097-1155 of SEQ ID NO:11; positions 31-89 of SEQ ID NO:14; positions 1-59 of SEQ ID NO:15; and a corresponding sequence from a different human MUC1 protein. In one aspect, the MUC1 SEA/ED has an amino acid sequence of positions 31-89 of SEQ ID NO:14 or positions 1-59 of SEQ ID NO:15.

In one aspect, the MUC1 TM domain has an amino acid sequence that is at least 95%, 96%, 97%, 98%, 99%, or 100% identical to an amino acid sequence selected from: positions 174-201 of SEQ ID NO:2, positions 165-192 of SEQ ID NO:4, positions 165-192 of SEQ ID NO:6, positions 156-183 of SEQ ID NO:8, positions 1156-1183 of SEQ ID NO:11, positions 131-158 of SEQ ID NO:14, positions 101-128 of SEQ ID NO:15, and a corresponding sequence from a different human MUC1 protein. In one aspect, the MUC1 TM domain has an amino acid sequence that is at least 95%, 96%, 97%, 98%, 99%, or 100% identical to positions 131-158 of SEQ ID NO:14 or positions 101-128 of SEQ ID NO:15. In one aspect, the MUC1 TM domain has an amino acid sequence of positions 131-158 of SEQ ID NO:14 or positions 101-128 of SEQ ID NO:15.

In one aspect, the MUC1 CD domain has an amino acid sequence that is at least 95%, 96%, 97%, 98%, 99%, or 100% identical to an amino acid sequence selected from: positions 202-273 of SEQ ID NO:2, positions 193-264 of SEQ ID NO:4, positions 193-264 of SEQ ID NO:6, positions 184-255 of SEQ ID NO:8, positions 1184-1255 of SEQ ID NO:11, positions 159-230 of SEQ ID NO:14, positions 129-200 of SEQ ID NO:15, positions 7-78 of SEQ ID NO:17, positions 79-150 of SEQ ID NO:17, positions 151-222 of SEQ ID NO:17; positions 1-72 of SEQ ID NO:18, positions 73-144 of SEQ ID NO:18, positions 145-216 of SEQ ID NO:18, and a corresponding sequence from a different human MUC1 protein. In one aspect, the MUC1 CD domain has an amino acid sequence that is at least 95%, 96%, 97%, 98%, 99%, or 100% identical to an amino acid sequence of positions 159-230 of SEQ ID NO:14 or positions 129-200 of SEQ ID NO:15. In one aspect, the MUC1 CD domain has an amino acid sequence of positions 159-230 of SEQ ID NO:14 or positions 129-200 of SEQ ID NO:15.

In one aspect of this embodiment of the invention, the MUC1 antigen has an amino acid sequence that is at least 95%, 96%, 97%, or 98% identical to SEQ ID NO:15. In one aspect, the MUC1 antigen comprises SEQ ID NO:15 or an amino acid sequence that is at least 99% identical to SEQ ID NO:15. In one aspect, the MUC1 antigen has an amino acid sequence of SEQ ID NO:15.

In one aspect of this embodiment of the invention, the fusion protein further comprises a MUC1 signal sequence appended to the N-terminus of the MUC1 SEA/ED. In one aspect, the MUC1 signal sequence has an amino acid sequence that is at least 95%, 96%, 97%, 98%, 99%, or 100% identical to an amino acid sequence selected from: positions 1-27 of SEQ ID NO:2, positions 1-32 of SEQ ID NO:4, positions 1-32 of SEQ ID NO:6, positions 1-27 of SEQ ID NO:8, positions 1-23 of SEQ ID NO:11, positions 1-30 of SEQ ID NO:14, and a corresponding sequence from a different human MUC1 protein. In one aspect, the MUC1 signal sequence has an amino acid sequence that is at least 95%, 96%, 97%, 98%, 99%, or 100% identical to an amino acid sequence of positions 1-30 of SEQ ID NO:14. In one aspect, the MUC1 signal sequence has an amino acid sequence of positions 1-30 of SEQ ID NO:14. In one aspect, the fusion protein has an amino acid sequence that is at least 95%, 96%, 97%, or 98% identical to SEQ ID NO:14. In one aspect, the fusion protein comprises SEQ ID NO:14 or an amino acid sequence that is at least 99% identical to SEQ ID NO:14. In one aspect, the fusion protein has an amino acid sequence of SEQ ID NO:14.

In one aspect of this embodiment of the invention, the MUC1 antigen comprises 1, 2, 3, 4, 5, 6, 7, 8, 9, 10, 11, or more amino acid substitutions, as compared to a wild-type MUC1 sequence, to form between one and 11 agonist epitopes within the MUC1 antigen, also referred to herein as a MUC1 agonist antigen. In one aspect of this embodiment of the invention, the amino acid substitutions are selected from: A96Y, P97L, G104V, S105Y, T106L, A147Y, C161V, T199L, D200F, S215Y, and T239L, with respect to the MUC1 antigen portion of SEQ ID NO:14 or SEQ ID NO:15. In one aspect, the MUC1 agonist antigen has an amino acid sequence that is at least 95%, 96%, 97%, or 98% identical to SEQ ID NO:23. In one aspect, the MUC1 antigen comprises SEQ ID NO:23 or an amino acid sequence that is at least 99% identical to SEQ ID NO:23. In one aspect, the MUC1 antigen has an amino acid sequence of SEQ ID NO:23. In one aspect, the MUC1 antigen comprises between one and eleven amino acid substitutions to create a MUC1 agonist antigen.

Another embodiment of the invention relates to a yeast-MUC1 immunotherapeutic composition comprising: (a) a yeast vehicle; and (b) a fusion protein expressed by the yeast vehicle and comprising at least one MUC1 antigen. The MUC1 antigen consists of two or more cytoplasmic domains (CD) of MUC1. In one aspect, the MUC1 antigen consists of three cytoplasmic domains (CD) of MUC1. In one aspect, the three CDs are from the same MUC1 protein. In one aspect, each CD domain comprises an amino acid sequence that is at least 95%, 96%, 97%, 98%, 99%, or 100% identical to an amino acid sequence selected from: positions 202-273 of SEQ ID NO:2, positions 193-264 of SEQ ID NO:4, positions 193-264 of SEQ ID NO:6, positions 184-255 of SEQ ID NO:8, positions 1184-1255 of SEQ ID NO:11, positions 159-230 of SEQ ID NO:14, positions 129-200 of SEQ ID NO:15, positions 7-78 of SEQ ID NO:17, positions 79-150 of SEQ ID NO:17, positions 151-222 of SEQ ID NO:17; positions 1-72 of SEQ ID NO:18, positions 73-144 of SEQ ID NO:18, positions 145-216 of SEQ ID NO:18, and a corresponding sequence from a different human MUC1 protein. In one aspect, each CD domain comprises an amino acid sequence that is at least 95%, 96%, 97%, 98%, 99%, or 100% identical to an amino acid sequence selected from: positions 129-200 of SEQ ID NO:15, positions 7-78 of SEQ ID NO:17, positions 79-150 of SEQ ID NO:17, positions 151-222 of SEQ ID NO:17; positions 1-72 of SEQ ID NO:18, positions 73-144 of SEQ ID NO:18, and positions 145-216 of SEQ ID NO:18.

In one aspect of this embodiment, the MUC1 antigen has an amino acid sequence that is at least 95%, 96%, 97%, or 98% identical to SEQ ID NO:18. In one aspect, the MUC1 antigen has an amino acid sequence of SEQ ID NO:18 or an amino acid sequence that is at least 99% identical to SEQ ID NO:18. In one aspect, the MUC1 antigen has an amino acid sequence of SEQ ID NO:18. In one aspect, the fusion protein has an amino acid sequence that is at least 95%, 96%, 97%, or 98% identical to SEQ ID NO:17. In one aspect, the fusion protein has an amino acid sequence of SEQ ID NO:17 or an amino acid sequence that is at least 99% identical to SEQ ID NO:17. In one aspect, the fusion protein has an amino acid sequence of SEQ ID NO:17.

Another embodiment of the invention relates to a yeast-MUC1 immunotherapeutic composition comprising: (a) a yeast vehicle; and (b) a fusion protein expressed by the yeast vehicle and comprising at least one MUC1 agonist antigen. In one aspect of this embodiment of the invention, the MUC1 agonist antigen comprises 1, 2, 3, 4, 5, 6, 7, 8, 9, 10, 11, or more amino acid substitutions, as compared to a wild-type MUC1 sequence, to form between one and 11 agonist epitopes within the MUC1 antigen, also referred to herein as a MUC1 agonist antigen. In one aspect, the MUC1 agonist antigen has an amino acid sequence that is at least 95%, 96%, 97%, or 98% identical to SEQ ID NO:23 or SEQ ID NO:25. In one aspect, the MUC1 antigen comprises SEQ ID NO:23 or SEQ ID NO:25 or an amino acid sequence that is at least 99% identical to SEQ ID NO:23 or SEQ ID NO:25. In one aspect, the MUC1 antigen has an amino acid sequence of SEQ ID NO:23 or SEQ ID NO:25.

Yet another embodiment of the invention relates to a method to reduce tumor burden, inhibit tumor growth, and/or increase survival of an individual who has a cancer that expresses MUC1. The method includes the step of administering to the individual a yeast-MUC1 immunotherapeutic composition described above or elsewhere herein. In one aspect, MUC1 expression is detected in the individual's cancer at the time the composition is first administered. In one aspect, the individual has a stage I cancer. In one aspect, the individual has a stage II cancer. In one aspect, the individual has a stage III cancer. In one aspect, the individual has a stage IV cancer.

Another embodiment of the invention relates to the use of any of the yeast-MUC1 immunotherapeutic compositions described herein to treat a disease. In one aspect, the disease is cancer.

Yet another embodiment of the invention relates to the use of any of the yeast-MUC1 immunotherapeutic compositions described herein to reduce, arrest, reverse or prevent the metastatic progression of cancer in an individual who has cancer.

Yet another embodiment of the invention relates to the use of any of the yeast-MUC1 immunotherapeutic compositions described herein to prevent or delay the onset of a MUC1-expressing cancer.

Another embodiment of the invention relates to the use of a combination of immunotherapeutic compositions to treat cancer, the immunotherapeutic compositions comprising: (a) a first composition that is any of the yeast-MUC1 immunotherapeutic compositions described herein; and (b) at least one additional immunotherapeutic composition comprising a yeast vehicle and an antigen that is not a MUC1 antigen. In one aspect, the antigen that is not a MUC1 antigen is selected from mutated Ras, carcinoembryonic antigen (CEA), and/or Brachyury.

In one aspect of any of the embodiments related to a method or use related to a yeast-MUC1 immunotherapy composition described herein, the individual is being treated or has been treated with another therapy for cancer, which can include, but is not limited to, chemotherapy, targeted cancer therapy, radiation therapy, adoptive T cell transfer, surgical resection of a tumor from the individual, and/or the administration of one or more additional immunotherapeutic compositions. In one aspect, the additional immunotherapeutic compositions comprise a second cancer antigen that is a MUC1 antigen or a cancer antigen that is not a MUC1 antigen. In one aspect, the additional immunotherapeutic compositions comprise a yeast vehicle and a second cancer antigen that does not include MUC1 antigen. In one aspect, the additional immunotherapeutic compositions comprise a second cancer antigen that includes, but is not limited to, mutated Ras, carcinoembryonic antigen (CEA), Brachyury, EGFR, BCR-Abl, MART-1, MAGE-1, MAGE-3, GAGE, GP-100, MUC-2, PSMA, tyrosinase, TRP-1 (gp75), NY-ESO-1, TRP-2, TAG72, KSA, CA-125, PSA, HER-2/neu/c-erb/B2, hTERT, p'73, B-RAF, adenomatous polyposis coli (APC), Myc, von Hippel-Lindau protein (VHL), Rb-1, Rb-2, androgen receptor (AR), Smad4, MDR1, Flt-3, BRCA-1, BRCA-2, pax3-fkhr, ews-fli-1, HERV-H, HERV-K, TWIST, Mesothelin, and/or NGEP. In one aspect, the second cancer antigen is selected from the group consisting of: mutated Ras, carcinoembryonic antigen (CEA) and Brachyury. In one aspect, the additional immunotherapeutic composition is a viral vector vaccine. In one aspect, the additional immunotherapeutic composition is a dendritic cell/tumor cell fusion.

Yet another embodiment of the invention relates to a method to prevent or delay the onset of a MUC1-expressing cancer. The method includes a step of administering to an individual any of the yeast-MUC1 immunotherapeutic compositions described herein. In one aspect, cancer has not been detected in the individual. In one aspect, the individual is at high risk for developing cancer. In one aspect, the individual has a pre-cancerous lesion. In one aspect, the individual has cancer, but MUC1-expressing cancer cells have not been detected in the cancer.

In any of the methods or uses related to a yeast-MUC1 immunotherapy composition described herein, in one aspect, the cancer is of epithelial cell origin. In one aspect, the cancer can include, but is not limited to: breast cancer, small intestine cancer, stomach cancer, pancreatic cancer, kidney cancer, bladder cancer, uterine cancer, ovarian cancer, testicular cancer, lung cancer, colon cancer, prostate cancer, melanoma, multiple myelogenous leukemia (MML), chronic lymphocytic leukemia (CLL), acute myeloid leukemia (AML), Burkitt's lymphoma, Hodgkin's lymphoma, cancers of secretory tissues, and metastatic cancers thereof. In one aspect, the cancer is selected from breast cancer and colon cancer. In one aspect, the cancer is selected from breast cancer, colon cancer, pancreas cancer, ovarian cancer, esophageal cancer, and AML. In one aspect, the cancer is AML, and the yeast-MUC1 immunotherapeutic composition is administered to both donor and recipient of bone marrow transplantation (BMT) therapy. In one aspect, the cancer is AML, and the yeast-MUC1 immunotherapeutic composition is administered to the individual in conjunction with cytarabine and anthracycline therapy.

In any of the embodiments of the invention described above or elsewhere herein, in one aspect, the yeast vehicle is a whole yeast. In one aspect, the yeast vehicle is heat-inactivated. In one aspect, the yeast vehicle is from a mutant yeast strain that produces underglycosylated proteins, as compared to a wild-type yeast strain. In one aspect, the MUC1 antigen is expressed on the cell wall of the yeast vehicle. In one aspect, the MUC1 antigen is expressed in the periplasm or cytoplasm of the yeast vehicle. In one aspect, the yeast vehicle is from *Saccharomyces*. In one aspect, the yeast vehicle is from *Saccharomyces cerevisiae*.

In any of the embodiments of the invention described above or elsewhere herein, in one aspect, the immunotherapeutic composition has been produced by culturing a whole yeast expressing the MUC1 antigen in a medium that was maintained at a pH level of between 5.5 and 8. In one aspect, the medium was buffered with a buffering agent. In one aspect, the yeast was cultured in a medium that was maintained at a pH level of between 6 and 8.

In any of the embodiments of the invention described above or elsewhere herein, in one aspect, the composition further comprises at least one biological response modifier.

In any of the embodiments of the invention described above or elsewhere herein, in one aspect, the composition further comprises a pharmaceutically acceptable excipient.

In any of the embodiments of the invention described above or elsewhere herein, in one aspect, the composition has been formulated for injection.

DETAILED DESCRIPTION OF THE INVENTION

Figure 1A:
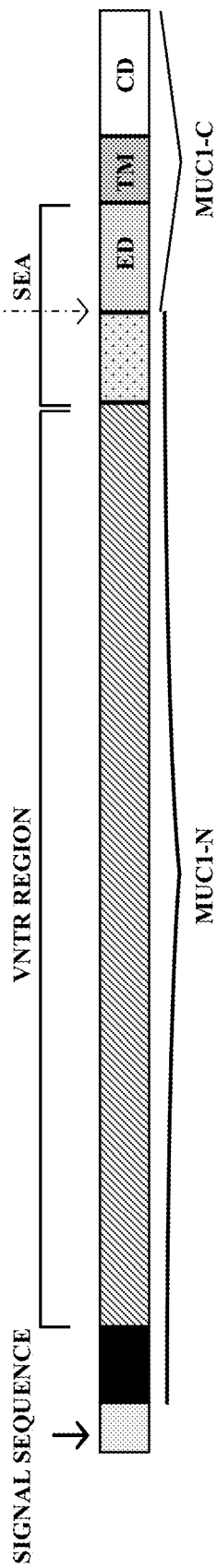
FIG. 1A is a schematic drawing showing the structure of full-length MUC1 protein.
Figure 1B:
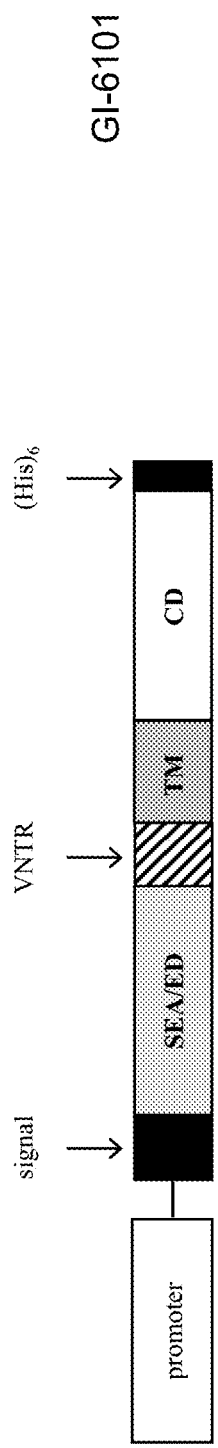
FIG. 1B is a schematic drawing showing the structure of the fusion protein expressed in the yeast-based immunotherapeutic composition known as GI-6101.
Figure 1C:
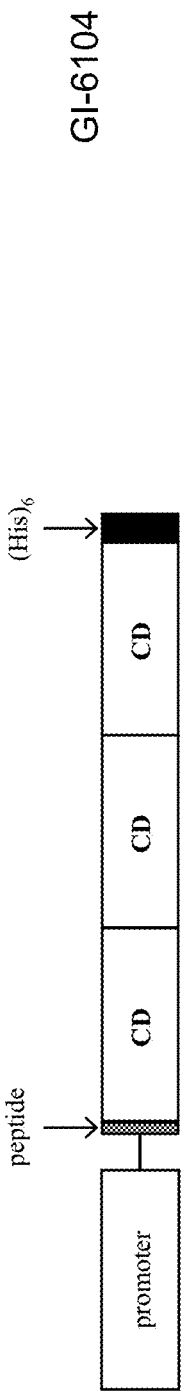
FIG. 1C is a schematic drawing showing the structure of the fusion protein expressed in the yeast-based immunotherapeutic composition known as GI-6104.

This invention generally relates to yeast-based immunotherapeutic compositions and methods for the prevention and/or treatment of cancers that express or overexpress mucin-1 (which may generally be referred to herein as "MUC1", and which is also known or has been known as "DF3 antigen" or "HMFG"). The invention includes the use of a yeast-based immunotherapeutic composition (also referred to as yeast-based immunotherapy composition or product) comprising a yeast vehicle and novel MUC1 antigens (also referred to herein as "yeast-MUC1 immunotherapy composition", "yeast-MUC1 immunotherapy product" or "yeast-MUC1 immunotherapeutic compositions"). The inventors describe herein the construction and production of novel yeast-MUC1 immunotherapy products, and demonstrate that yeast-MUC1 immunotherapy matures human dendritic cells (DCs), increases cytokine production from DCs that is associated with immune responses expected to be beneficial in the treatment of tumors, and elicits the activation of MUC1-specific T cell lines. Taken together, the data presented herein show that yeast-MUC1 immunotherapy is useful for the elicitation of MUC1-specific cellular immune responses ($CD4^+$ and $CD8^+$) and that yeast-MUC1 immunotherapy is expected to be useful for the prevention and treatment of MUC1-expressing tumors.

Yeast-MUC1 immunotherapy is readily adaptable to the use of additional tumor antigens within the same yeast composition, or to use in combination with other yeast-based immunotherapeutics that target other tumor antigens (sequentially or concurrently) or other immunotherapeutics and treatments/therapies for cancer. Accordingly, the Yeast-MUC1 immunotherapy can be adapted to the cancer type, the cancer stage, the cancer grade, the antigens expressed by the tumor, and the overall medical status of the individual (i.e., the therapy is easily personalized), and for the individual who already has cancer, its use can be modified as cancer progresses in an individual, in order to provide maximum efficacy at a variety of tumor stages. Yeast-MUC1 immunotherapy offers the opportunity for the broad-based prophylactic and/or therapeutic treatment of a wide range of cancers.

Indeed, yeast-MUC1 immunotherapy can be used in a flexible manner to treat various MUC1-positive cancers by tailoring the yeast-MUC1 immunotherapy to the particular role this antigen plays in each type of cancer indication. For example, since MUC1 has been described as an early marker in cancers such as breast cancer or colon cancer, yeast-based immunotherapy may be used prophylactically in patients with MUC1 positive premalignant breast hyperplasia or colonic polyps. As another example, since MUC1 has been associated with epithelial-mesenchymal transition (EMT) pathways and metastatic spread in cancers such as pancreas cancer, ovarian cancer, and esophageal cancer, yeast-MUC1 immunotherapy can be used as a therapeutic add-on to standard of care therapy in these cancers to promote the arrest of metastatic spread in MUC1-positive stage 3 pancreas, ovarian, and esophageal cancers. As yet another example, since MUC1 has been shown to prevent terminal differentiation by reactive oxygen species in acute myeloid leukemia (AML), thereby allowing unlimited self renewal of these cancer cells, yeast-MUC1 immunotherapy can be used as an add-on to standard therapy in MUC1-positive AML to promote apoptosis and prevent the unlimited self renewal of the malignant cells. A clinical trial using yeast-MUC1 immunotherapy in AML patients is described in the examples.

Yeast-MUC1 compositions described herein induce innate immune responses, as well as adaptive immune responses against the target antigen (MUC1), including CD4-dependent TH17 and TH1 T cell responses and antigen-specific $CD8^+$ T cell responses, which include cytotoxic T lymphocyte (CTL) responses, all without the use of exogenous adjuvants, cytokines, or other immunostimulatory molecules, many of which have to toxicity issues. In addition, Yeast-MUC1 immunotherapeutic compositions inhibit regulatory T cell (Treg) numbers and/or functionality, thereby enhancing effector T cell responses that might normally be suppressed by the presence of the tumor, for example. Moreover, as compared to immunotherapeutic compositions that immunize by generating antibody responses, the antigen-specific, broad-based, and potent cellular immune responses elicited by Yeast-MUC1 immunotherapy are believed to be particularly effective in targeting tumor cells. Indeed, numerous studies have shown that immunotherapeutic approaches are enhanced when tumor cells are targeted via $CD8^+$ CTLs which recognize tumor peptides in the context of MHC Class I molecules. Yeast-MUC1 immunotherapy is highly adept at activating antigen presenting cells, and has a unique ability to cross-prime the immune response, generating $CD8^+$ CTL responses that are typically effective against tumors, even in the face of what may otherwise be a suppressive environment. Since this type of immunotherapy utilizes the natural ability of the antigen presenting cell to present relevant immunogens, it is not necessary to know the precise identity of CTL epitopes or MHC Class II epitopes of MUC1 to produce an effective immunotherapeutic according to the present invention. In fact, multiple $CD4^+$ and $CD8^+$ T cell epitopes can be targeted in a single Yeast-MUC1 immunotherapeutic composition, and so the Yeast-MUC1 immunotherapeutics of the invention are not limited to the use of short peptides. Indeed, the use of longer polypeptides and fusion proteins containing multiple domains of the target antigen in these compositions is efficacious. Accordingly, by using Yeast-MUC1 immunotherapy, the use of algorithms and complex formulas to identify putative T cell epitopes is eliminated.

Yeast-MUC1 can be effectively utilized in an immunization protocol (prophylactic or therapeutic) without the use of exogenous adjuvants, immunostimulatory agents or molecules, costimulatory molecules, or cytokines, although such agents may be included, if desired. Moreover, Yeast-MUC1 immunotherapy can be administered repeatedly without losing efficacy, as may be problematic with other types of immunotherapy.

Compositions of the Invention

One embodiment of the present invention relates to a yeast-based immunotherapy composition which can be used to prevent and/or treat cancers characterized by MUC1 expression or overexpression (including cancers that may not contain cells expressing detectable MUC1 initially, but which may or will contain cells expressing MUC1 at later stages of the development of the cancer). The composition is a Yeast-MUC1 immunotherapeutic composition comprising: (a) a yeast vehicle; and (b) a cancer antigen comprising one or more MUC1 antigen(s) and/or immunogenic domain (s) thereof. The MUC1 antigen or immunogenic domain thereof is most typically expressed as a recombinant protein by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or more MUC1 antigens are loaded into a yeast vehicle or otherwise complexed with, attached to, mixed with or administered with a yeast vehicle as described herein to form a composition of the present invention.

A "Yeast-MUC1 immunotherapeutic composition" is a specific type of "yeast-based immunotherapeutic composition" that contains at least one MUC1 antigen or immunogenic domain thereof. The phrase, "yeast-based immunotherapeutic composition" may be used interchangeably with "yeast-based immunotherapy product", "yeast-based immunotherapy composition", "yeast-based composition", "yeast-based immunotherapeutic", "yeast-based vaccine", or derivatives of these phrases. An "immunotherapeutic composition" is a composition that elicits an immune response sufficient to achieve at least one therapeutic benefit in a subject. As used herein, yeast-based immunotherapeutic composition refers to a composition that includes a yeast vehicle component and that elicits an immune response sufficient to achieve at least one therapeutic benefit in a subject. More particularly, a yeast-based immunotherapeutic composition is a composition that includes a yeast vehicle component and typically, an antigen component, and can elicit or induce an immune response, such as a cellular immune response, including without limitation a T cell-mediated cellular immune response. In one aspect, a yeast-based immunotherapeutic composition useful in the invention is capable of inducing a CD8+ and/or a CD4+ T cell-mediated immune response and in one aspect, a CD8+ and a CD4+ T cell-mediated immune response, particularly against a target antigen (e.g., a cancer antigen). A CD4+ immune response can include TH1 immune responses, TH2 immune responses, TH17 immune responses, or any combination of the above. Yeast-based immunotherapeutics are particularly capable of generating TH1 and TH17 responses. A CD8+ immune response can include a cytotoxic T lymphocyte (CTL) response, and yeast-based immunotherapeutics are capable of generating such responses. In one aspect, a yeast-based immunotherapeutic composition modulates the number and/or functionality of regulatory T cells (Tregs) in a subject. Yeast-based immunotherapy can also be modified to promote one type of response over another, e.g., by the addition of cytokines, antibodies, and/or modulating the manufacturing process for the yeast. Optionally, a yeast-based immunotherapeutic composition is capable of eliciting a humoral immune response.

Yeast-MUC1 immunotherapeutic compositions of the invention may be either "prophylactic" or "therapeutic". When provided prophylactically, the compositions of the present invention are provided in advance of the development of, or the detection of the development of, a cancer that expresses MUC1, with the goal of preventing, inhibiting or delaying the development of MUC1-expressing tumors; and/or preventing, inhibiting or delaying metastases of such tumors and/or generally preventing or inhibiting progression of cancer in an individual. As discussed herein, MUC1 is expressed in several cancers. Therefore, prophylactic compositions can be administered to individuals that appear to be cancer-free (healthy, or normal, individuals), to individuals with pre-cancerous (pre-malignant lesions), and also to individuals who have cancer, but in which MUC1 has not yet been detected (i.e. prior to the expression of MUC1 by tumor cells in the cancer). Individuals who are at high risk for developing a cancer, particularly a cancer with which MUC1 expression and/or metastases are typically associated, may be treated prophylactically with a composition of the invention. When provided therapeutically, the immunotherapy compositions are provided to an individual with a MUC1-expressing cancer, with the goal of ameliorating the cancer, such as by reducing tumor burden in the individual; inhibiting tumor growth in the individual; increasing survival of the individual; and/or preventing, inhibiting, reversing or delaying progression of the cancer in the individual.

Typically, a Yeast-MUC1 immunotherapy composition includes a yeast vehicle and at least one cancer antigen comprising a MUC1 antigen or immunogenic domain thereof, where the cancer antigen is expressed by, attached to, loaded into, or mixed with the yeast vehicle. In some embodiments, the cancer antigen, MUC1 antigen, or immunogenic domain thereof is provided as a fusion protein. Several MUC1 proteins and fusion proteins suitable for use in the compositions and methods of the invention are described below. In some embodiments, the cancer antigen and the MUC1 antigen are the same element. In some embodiments, the cancer antigen includes other antigens, including other cancer antigens, in addition to the MUC1 antigen. In one aspect of the invention, a fusion protein useful as a cancer antigen can include two or more antigens, e.g., a MUC1 antigen and another cancer antigen that is not a MUC1 antigen, or two different MUC1 antigens. In one aspect, the fusion protein can include two or more immunogenic domains of one or more antigens, such as two or more immunogenic domains of a MUC1 antigen, or two or more epitopes of one or more antigens, such as two or more epitopes of a MUC1 antigen.

According to the present invention, a yeast vehicle used in a Yeast-MUC1 immunotherapy composition is any yeast cell (e.g., a whole or intact cell) or a derivative thereof (see below) that can be used in conjunction with one or more antigens, immunogenic domains thereof or epitopes thereof in a composition of the invention (e.g., a therapeutic or prophylactic composition). The yeast vehicle can therefore include, but is not limited to, a live intact (whole) yeast microorganism (i.e., a yeast cell having all its components including a cell wall), a killed (dead) or inactivated intact yeast microorganism, or derivatives of intact yeast including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., 1991, *Meth. Enzymol.* 194, 662-674., incorporated herein by reference in its entirety.

Yeast cytoplasts are typically produced by enucleation of yeast cells. Such a method is described, for example, in Coon, 1978, *Natl. Cancer Inst. Monogr.* 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, *J. iol. Chem.* 258, 3608-3614 and Bussey et al., 1979, *Biochim. Biophys. Acta* 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane.

An example of a yeast cell wall preparation is a preparation of isolated yeast cell walls carrying an antigen on its surface or at least partially embedded within the cell wall such that the yeast cell wall preparation, when administered to an animal, stimulates a desired immune response against a disease target.

Any yeast strain can be used to produce a yeast vehicle of the present invention. Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains). In accordance with one aspect of the present invention, non-pathogenic yeast strains are used.

Genera of yeast strains that may be used in the invention include but are not limited to *Saccharomyces, Candida* (which can be pathogenic), *Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in one aspect, *Saccharomyces* is used. Species of yeast strains that may be used in the invention include but are not limited to *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe*. *S. cerevisiae* is useful as it is relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain. The *S. cerevisiae* strain is one such strain that is capable of supporting expression vectors that allow one or more target antigen(s) and/or antigen fusion protein(s) and/or other proteins to be expressed at high levels. Another yeast strain is useful in the invention is *Saccharomyces cerevisiae* W303α. In addition, any mutant yeast strains can be used in the present invention, including those that exhibit reduced post-translational modifications of expressed target antigens or other proteins, such as mutations in the enzymes that extend N-linked glycosylation. In one aspect of the invention, a yeast-MUC1 immunotherapy composition is produced using a mutant yeast strain that produces the MUC1 antigen as an underglycosylated protein as compared to the same antigen produced by the wild-type strain (with normal glycosylation). Such a MUC1 antigen may be more similar to MU1 antigens expressed by tumor cells, which can then be processed into unique T cell epitopes by antigen presenting cells, thus enhancing the specific anti-tumor response.

The Yeast-MUC1 immunotherapy composition of the invention includes at least one cancer antigen comprising a MUC1 antigen. According to the present invention, the general use herein of the term "antigen" refers: to any portion of a protein (e.g., peptide, partial protein, full-length protein), wherein the protein is naturally occurring or synthetically derived or designed, to a cellular composition (whole cell, cell lysate or disrupted cells), to an organism (whole organism, lysate or disrupted cells) or to a carbohydrate, or other molecule, or a portion thereof. An antigen may elicit an antigen-specific immune response (e.g., a humoral and/or a cell-mediated immune response) against the same or similar antigens that are encountered in vitro, in vivo, or ex vivo by an element of the immune system (e.g., T cells, antibodies).

An antigen can be as small as a single epitope, a single immunogenic domain or larger, and can include multiple epitopes or immunogenic domains. As such, the size of an antigen can be as small as about 8-11 amino acids (i.e., a peptide) and as large as: a domain of a protein, a full-length protein, a multimer, a fusion protein, a chimeric protein, a whole cell, a whole microorganism, or any portions thereof (e.g., protein fragments (polypeptides) lysates of whole cells or extracts of microorganisms). Antigens useful in the Yeast-MUC1 immunotherapeutic of the present invention are peptides, polypeptides, protein domain(s), protein subunits, full-length proteins, multimers, fusion proteins and chimeric proteins. In addition, antigens can include carbohydrates, which can be loaded into a yeast vehicle or into a composition of the invention. It will be appreciated that in some embodiments (e.g., when the antigen is expressed by the yeast vehicle from a recombinant nucleic acid molecule), the antigen is a protein (including fragments, domains, subunits, and full-length proteins), fusion protein, chimeric protein, or fragment thereof, rather than an entire cell or microorganism. For expression in yeast, in one embodiment, an antigen is of a minimum size capable of being expressed recombinantly in yeast if the antigen is the entire protein to be expressed by the yeast (in other words, the protein that is expressed by the yeast, which may include or consist of the antigen, is preferably at least 25 amino acids in length), and is typically at least or greater than 25 amino acids in length, or at least or greater than 26 amino acids, at least or greater than 27 amino acids, at least or greater than 28 amino acids, at least or greater than 29 amino acids, at least or greater than 30 amino acids, at least or greater than 31 amino acids, at least or greater than 32 amino acids, at least or greater than 33 amino acids, at least or greater than 34 amino acids, at least or greater than 35 amino acids, at least or greater than 36 amino acids, at least or greater than 37 amino acids, at least or greater than 38 amino acids, at least or greater than 39 amino acids, at least or greater than 40 amino acids, at least or greater than 41 amino acids, at least or greater than 42 amino acids, at least or greater than 43 amino acids, at least or greater than 44 amino acids, at least or greater than 45 amino acids, at least or greater than 46 amino acids, at least or greater than 47 amino acids, at least or greater than 48 amino acids, at least or greater than 49 amino acids, or at least or greater than 50 amino acids in length, or at least 25-50 amino acids in length, at least 30-50 amino acids in length, or at least 35-50 amino acids in length, or at least 40-50 amino acids in length, or at least 45-50 amino acids in length, although smaller proteins may be expressed, and considerably larger proteins (e.g., hundreds of amino acids in length or even a few thousand amino acids in length) may be expressed. In one aspect, a full-length protein or domain of a protein that is lacking between 1 and 20 amino acids from the N- and/or the C-terminus may be expressed. Fusion proteins and chimeric proteins are also antigens that may be expressed in the invention. A "target antigen" is an antigen that is specifically targeted by an immunotherapeutic composition of the invention (i.e., an antigen, usually the native antigen, against which elicitation of an immune response is desired). A "cancer antigen" is an antigen that comprises at least one antigen that is associated with a cancer such as an antigen expressed by a tumor cell, so that targeting the antigen also targets the tumor cell and/or cancer. A cancer antigen can include one or more antigens from one or more proteins, including one or more tumor-associated proteins. A "MUC1 antigen" is an antigen derived, designed, or produced from a MUC1 protein (including MUC1-N, MUC1-C or both MUC1-N and MUC1-C).

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual. In one embodiment, the immunogen elicits a cell-mediated immune response, including a CD4+ T cell response (e.g., TH1, TH2 and/or TH17) and/or a CD8$^+$ T cell response (e.g., a CTL response).

An "immunogenic domain" or "immunological domain" of a given antigen can be any portion, fragment or epitope of an antigen (e.g., a peptide fragment or subunit or an antibody epitope or other conformational epitope) that contains at least one epitope that can act as an immunogen when administered to an animal. Therefore, an immunogenic domain is larger than a single amino acid and is at least of a size sufficient to contain at least one epitope that can act as an immunogen. For example, a single protein can contain multiple different immunogenic domains. Immunogenic domains need not be linear sequences within a protein, such as in the case of a humoral immune response, where conformational domains are contemplated.

An epitope is defined herein as a single immunogenic site within a given antigen that is sufficient to elicit an immune response when provided to the immune system in the context of appropriate costimulatory signals and/or activated cells of the immune system. In other words, an epitope is the part of an antigen that is recognized by components of the immune system, and may also be referred to as an antigenic determinant. Those of skill in the art will recognize that T cell epitopes are different in size and composition from B cell or antibody epitopes, and that epitopes presented through the Class I MHC pathway differ in size and structural attributes from epitopes presented through the Class II MHC pathway. For example, T cell epitopes presented by Class I MHC molecules are typically between 8 and 11 amino acids in length, whereas epitopes presented by Class II MHC molecules are less restricted in length and may be up to 25 amino acids or longer. In addition, T cell epitopes have predicted structural characteristics depending on the specific MHC molecules bound by the epitope. Epitopes can be linear sequence epitopes or conformational epitopes (conserved binding regions). Most antibodies recognize conformational epitopes.

MUC1 (which may also be referred to as "mucin-1" and also "DF3 antigen" or "HMFG1") is a large glycoprotein expressed by most epithelial secretory tissues at basal levels and is expressed at high levels by malignancies of epithelial cell origin. MUC1 is most typically found as a polymorphic, type I transmembrane protein with a large extracellular domain (also referred to as MUC1-N subunit) that includes variable numbers of tandem repeats (VNTR; typically between 20 and 125 repeats) that are highly glycosylated through 0-linkages. The MUC1 protein is encoded as a single transcript, and then processed into subunits post-translationally, known as MUC1-N and MUC1-C, or α and β subunits, respectively, which then form a heterodimeric protein by a strong noncovalent interaction of the two subunits. MUC1 is cleaved into its N- and C-subunits within the "sea urchin sperm protein, enterokinase and agrin" (SEA) domain, a highly conserved protein domain that was named based on its initial identification in a sperm protein, in enterokinase, and in agrin, and that is found in a number of heavily glycosylated mucin-like proteins that are typically membrane-tethered. The MUC1 protein is cleaved between glycine and serine residues present in the sequence GSVVV (e.g., positions 1097-1101 of SEQ ID NO:11) within the SEA domain (Lillehoj et al., 2003, Biochem. Biophys. Res. Commun. 307:743-749; Parry et al., 2001, Biochem. Biophys. Res. Commun. 283:715-720; Wreschner et al., 2002, Protein Sci. 11:698-706).

The MUC1-C subunit includes the extracellular domain (ED), which is glycosylated and binds the galectin-3 ligand, which in turn serves as a bridge to physically associate MUC1 with the epidermal growth factor receptor (EGFR) and possibly other receptor tyrosine kinases. MUC1-C also comprises a transmembrane (TM) domain, and a cytoplasmic domain (CD) which contains several tyrosine residues which, when phosphorylated, could act as binding motifs for proteins with SH2 domains (for a detailed discussion of the MUC1 protein and known and putative functions, see Kufe, 2008, Cancer Biol. & Ther. 7:81-84). Alternative splice variants of MUC1 (known as MUC1/Y and MUC1/X, for example) are "short" versions of MUC1 that lack most of MUC1-N, including the large VNTR region, but that include the ED, TM and CD regions, as well as the SEA domain and portions of the N-terminal region signal sequence region. Cleavage within the SEA domain may not occur in these short versions.

The isolation and sequencing of DNA and cDNA encoding human MUC1 has been reported (see, e.g., Siddiqui et al., 1998, PNAS 85:2320-2323; Abe and Kufe, 1993, PNAS 90:282-286; Hareuveni et al., 1990, Eur. J. Biochem. 189(3) 475-486; Gendler et al., 1990, 1 Biol. Chem. 265 (25) 15286-15293; Lan et al., 1990, 1 Biol. Chem 265(25) 15294-15299; Tsarfaty et al., 1990, Gene 93(2) 313-318; Lancaster, 1990, Biochem. Biophys. Res. Commun. 173(3) 1019-1029). An example of a full-length human MUC1 precursor protein containing both the MUC1-N and MUC1-C regions is described in SwissProt Accession No. P15941.3 (GI:296439295), and is represented here by SEQ ID NO:11. 10 different MUC1 isoforms can be created from the gene encoding SEQ ID NO:11 by alternative transcript splicing. For example, an isoform known as MUC1/Y lacks positions 54-1053 of SEQ ID NO:11. Various other isoforms are described in the database description of this protein.

For purposes of illustration of the identification of domains within the MUC1 protein, which can be applied to any human MUC1 protein as well as other mammalian MUC1 proteins, the following domains can be readily identified in SEQ ID NO:11. The MUC1 signal sequence, also referred to herein as the leader sequence, is located at about positions 1-23 of SEQ ID NO:11 (the MUC1 signal sequence is identified as longer in some MUC1 variants, and may include additional amino acids, such as positions 1-32). The MUC1-N subunit or α subunit comprises approximately positions 24-1097 of SEQ ID NO:11, and the MUC1-C subunit or β subunit comprises approximately positions 1098-1255 of SEQ ID NO:11.

Within the MUC1-N subunit, the VNTR (variable numbers of tandem repeats) domain can be found, comprising multiple repeats in this particular protein, including approximately the region from position 126-965, which contains forty-two 20-amino acid repeats of the sequence PAPG-STAPPAHGVTSAPDTR (e.g., positions 126-145 of SEQ ID NO:11), which is the commonly recognized VNTR sequence (see also SEQ ID NO:12 below, which designates common polymorphisms within this sequence). Since these are repeated sequences, one may begin counting from any one of the 20 amino acids in one VNTR and then restart numbering with the repeat of that first amino acid. More particularly, since a single VNTR domain is an approximately 20 amino acid sequence that is preceded by and/or followed by another identical, nearly identical, or homologous 20 amino acid sequence, which may be within a large number of such repeated sequences, for purposes of describing a single VNTR within a region of VNTRs, one may consider "position 1" of a given VNTR to be any one of the 20 amino acids in the VNTR, and then the prior and subsequent flanking amino acids will be numbered accordingly, with the amino acid that is upstream of (prior to) position 1 being either the last amino acid (position 20) of the prior VNTR or the last amino acid of the sequence linked to the VNTR (if such prior sequence is not also a VNTR), and the amino acid that is downstream of position 1 being position 2 of that VNTR, followed by position 3, and so on, until the sequence repeats with the next VNTR.

Positions 61-1120 of SEQ ID NO:11 includes the VNTR region discussed above, plus additional regions denoted as "repetitive regions". For example, positions 81-100, positions 101-120, positions 121-140, positions 141-160, positions 161-180, positions 181-200, positions 201-220, positions 221-240, positions 241-260, positions 261-180, positions 281-300, and so on, in 20 amino acid increments through positions 1001-1120 of SEQ ID NO:11, represent repetitive regions in this protein.

In the full-length MUC1 protein represented by SEQ ID NO:11 (prior to cleavage into subunits), the SEA domain spans positions 1034-1152 of SEQ ID NO:11. Cleavage of the SEA domain between amino acids 1097 and 1098 of SEQ ID NO:11 produces the MUC1-C domain. Within the MUC1-C domain, the extracellular domain (ED) is found at about positions 1098-1155 of SEQ ID NO:11; the transmembrane (TM) domain is found at about positions 1156-1183 of SEQ ID NO:11; and the cytoplasmic domain (CD, also called the cytoplasmic tail) is found at about positions 1184-1255 of SEQ ID NO:11.

The number of VNTR in a given MUC1-N subunit is highly polymorphic, and can vary, e.g., from 20 to 125 repeats. The tandemly repeated icosapeptide typically has a polymorphism at one or more of three positions (positions 9, 18 and 19 of SEQ ID NO:12): PAPGSTAP[P/A/Q/T]AHGVTSAP[DT/ES]R (SEQ ID NO:12, bracketed regions indicate common polymorphisms), where the polymorphism at positions 18 and 19 of SEQ ID NO:12 occur with the preference of DT>ES, and where the single replacements at position 9 occur with the following preference: P>A, P>Q and P>T. The most frequent replacement, DT>ES, occurs in up to 50% of the repeats.

A variety of transcript variants of MUC1 are known, but the MUC1 subunits, domains, or regions described in the exemplary SEQ ID NO:11 above can readily be identified in the variants, such that a MUC1 antigen useful in the invention can be designed or produced based on a given MUC1 sequence, or a corresponding sequence from another MUC1 protein. For example, one nucleotide sequence encoding a human MUC1 protein is represented herein by SEQ ID NO:1, which corresponds to GENBANK® Accession No. NM_002456.4 (GI: 65301116). SEQ ID NO:1 encodes a 273 amino acid human MUC1 protein (transcript variant 1, also known as MUC1/ZD), the amino acid sequence of which is represented here as SEQ ID NO:2 (also found in GENBANK® Accession No. NP 002447.4; GI:65301117). Within SEQ ID NO:2, the following domains are present: signal sequence (positions 1-27 of SEQ ID NO:2); SEA domain (positions 55-170 of SEQ ID NO:2); ED (positions 116-173 of SEQ ID NO:2); TM domain (positions 174-201 of SEQ ID NO:2); and CD (positions 202-273 of SEQ ID NO:2). The proteolytic cleavage site within the SEA domain that cleaves the ED domain from the N-terminal portion of the SEA domain is between positions 115 and 116 of SEQ ID NO:2. This transcript variant does not contain the VNTR region as shown in SEQ ID NO:11.

Another nucleotide sequence encoding another human MUC1 protein is represented herein by SEQ ID NO:3, which corresponds to GENBANK® Accession No. NM_001018016.1 (GI:67189006). SEQ ID NO:3 encodes a 264 amino acid human MUC1 protein (transcript variant 2, also known as "MUC1/Y"), the amino acid sequence of which is represented here as SEQ ID NO:4 (also found in GENBANK® Accession No. NP 001018016.1; GI:67189007). Within SEQ ID NO:4, the following domains are present: signal sequence (positions 1-32 of SEQ ID NO:4); SEA domain (positions 45-161 of SEQ ID NO:4); ED (107-164 of SEQ ID NO:4); TM domain (positions 165-192 of SEQ ID NO:4); and CD (positions 193-264 of SEQ ID NO:4). The proteolytic cleavage site within the SEA domain that cleaves the ED domain from the N-terminal portion of the SEA domain is between positions 106 and 107 of SEQ ID NO:4. This transcript variant does not contain the VNTR region as shown in SEQ ID NO:11.

Another nucleotide sequence encoding another human MUC1 protein is represented herein by SEQ ID NO:5, which corresponds to GENBANK® Accession No. AY327587.1 (GI:33150003). SEQ ID NO:5 encodes a 264 amino acid human MUC1 protein (transcript variant 2, also known as "MUC1/Y"), the amino acid sequence of which is represented here as SEQ ID NO:6 (also found in GENBANK® Accession No. AAP97018.1 (GI: 33150004). Within SEQ ID NO:6, the following domains are present: signal sequence (positions 1-32 of SEQ ID NO:6); SEA domain (positions 45-161 of SEQ ID NO:6); ED (positions 107 to 164 of SEQ ID NO:6); TM domain (positions 165-192 of SEQ ID NO:6); and CD (positions 193 to 264 of SEQ ID NO:6). The proteolytic cleavage site within the SEA domain that cleaves the ED domain from the N-terminal portion of the SEA domain is between positions 106 and 107 of SEQ ID NO:6. This transcript variant does not contain the VNTR region as shown in SEQ ID NO:11. SEQ ID NO:6 is 99% identical to SEQ ID NO:4, illustrating the high degree of homology among MUC1 sequences from different sources.

Another nucleotide sequence encoding another human MUC1 protein is represented herein by SEQ ID NO:7, which corresponds to GENBANK® Accession No. NM_001018017 (GI:324120954). SEQ ID NO:7 encodes a 255 amino acid human MUC1 protein (transcript variant 3), the amino acid sequence of which is represented here as SEQ ID NO:8 (also found in GENBANK® Accession No. NP 001018017.1; GI:67189069). Within SEQ ID NO:8, the following domains are present: signal sequence (positions 1-27 of SEQ ID NO:8); SEA domain (positions 36-152 of SEQ ID NO:8); ED (positions 98-155 of SEQ ID NO:8); TM domain (positions 156-183 of SEQ ID NO:8); and CD (positions 184-255 of SEQ ID NO:8). The proteolytic cleavage site within the SEA domain that cleaves the ED domain from the N-terminal portion of the SEA domain is between positions 97 and 98 of SEQ ID NO:6. This transcript variant does not contain the VNTR region as shown in SEQ ID NO:11.

Human MUC1 has high homology with MUC1 from other animal species and therefore, one can expect to be able to identify the domains within a given MUC1 protein based on comparison of sequences. In addition, one could utilize certain sequences of MUC1 from other animal species, and particularly mammalian species, in the preparation of a Yeast-MUC1 immunotherapeutic composition of the invention, particularly where these sequences are identical or substantially homologous, and where these sequences elicit an effective immune response against the target antigen (e.g., native MUC1 expressed by a tumor cell). For example, a murine MUC1 protein is represented herein by the amino acid sequence of SEQ ID NO:9. SEQ ID NO:9 corresponds to GENBANK® Accession No. NM_013605 (GI:7305292). SEQ ID NO:9 encodes a 631 amino acid murine MUC1 protein, the amino acid sequence of which is represented here as SEQ ID NO:10 (also found in GENBANK® Accession No. NP_038633; GI:7305293). Within SEQ ID NO:10, the following domains are present: signal sequence (approximately positions 1-20 of SEQ ID NO:10); VNTR (identifiable within positions 21-425 of SEQ ID NO: 10); SEA domain (positions 426-528 of SEQ ID NO: 10); ED (positions 475-536 of SEQ ID NO:10); TM domain (positions 531-559 of SEQ ID NO: 10); and CD (positions 560-631 of SEQ ID NO: 10). The proteolytic cleavage site within the SEA domain that cleaves the ED domain from the N-terminal portion of the SEA domain is between positions 474 and 475 of SEQ ID NO:10. To illustrate the level of conservation of MUC1 sequences within domains, the murine MUC1 SEA domain of SEQ ID NO:10 is 62% identical and 68% homologous or positive (as defined by BLAST) to the human MUC1 SEA domain of SEQ ID NO:11. The murine MUC1 ED of SEQ ID NO:10 is 56% identical and 73% homologous to the human MUC1 ED of SEQ ID NO:11. The murine MUC1 TM domain of SEQ ID NO:10 is 89% identical and 93% homologous to the human MUC1 TM domain of SEQ ID NO:11. The murine MUC1 CD of SEQ ID NO:10 is 88% identical and 88% homologous to the human MUC1 CD of SEQ ID NO:11.

Human MUC1, including the human MUC1 proteins and MUC1 antigens described herein, contains various $CD4^+$ and $CD8^+$ T cell epitopes. Such T cell epitopes have been described, for example, in U.S. Pat. Nos. 6,546,643; 7,118, 738; 7,342,094; 7,696,306; and U.S. Patent Application Publication No. 2008/0063653.

In one embodiment of the invention, a MUC1 antigen comprises or consists of a fusion protein comprising multiple domains of a MUC1 protein. In one embodiment, the MUC1 antigen is derived or designed from portions of the MUC1-C subunit. In one embodiment, the MUC1 antigen is derived or designed from portions of the MUC1-N subunit. In one embodiment, the MUC1 antigen is derived or designed from portions of both the MUC1-C and the MUC1-N subunits.

In one embodiment of the invention, a fusion protein useful in a yeast-based immunotherapeutic composition of the invention includes at least two, at least three, at least four, or at least five of the following MUC1 antigens, arranged in any order within the fusion protein, and any of which may be repeated two or more times within the fusion protein (e.g., a combination of two or more CD segments): (1) a MUC1 signal sequence; (2) at least one portion of a MUC1 SEA domain and/or at least one portion of the MUC1 extracellular domain (ED) or an immunogenic domain thereof, which may include, in one aspect, most of or the entire ED in addition to flanking one or more flanking amino acids from the SEA domain; (3) at least two VNTR domains; (4) at least one MUC1 transmembrane domain or immunogenic domain thereof; and (5) at least one MUC1 cytoplasmic domain (CD) or immunogenic domain thereof. Such a fusion protein is not and does not comprise a full-length MUC1 protein (i.e., it does not include a complete MUC1-N subunit and a complete MUC1-C subunit), and such a fusion protein does not comprise a full-length MUC1-N subunit. In one aspect, such a fusion protein does not comprise a full-length MUC1-C subunit. In one aspect, the segments of the fusion protein (e.g., MUC1 proteins or domains, including immunogenic domains) are arranged in a different order than the arrangement of the segments as they would occur in a native or wild-type MUC1 protein.

A MUC1 signal sequence (or leader sequence) useful in a fusion protein described above or elsewhere herein can be a signal sequence from any MUC1 protein, and in one aspect, is from a human MUC1 protein. In one aspect of the invention, the MUC1 signal sequence used in a fusion protein of the invention has an amino acid sequence comprising or consisting of an amino acid sequence selected from: positions 1-27 of SEQ ID NO:2, positions 1-32 of SEQ ID NO:4, positions 1-32 of SEQ ID NO:6, positions 1-27 of SEQ ID NO:8, positions 1-23 of SEQ ID NO:11, positions 1-30 of SEQ ID NO:14, a corresponding sequence from a different MUC1 protein such as another human MUC1 protein, or an amino acid sequence that is at least 95% identical, at least 96% identical, at least 97% identical, at least 98% identical, or at least 99% identical, to any one of these amino acid sequences. The MUC1 signal sequence is, in one aspect of the invention, placed at the N-terminus of a fusion protein useful in the invention. In one aspect of the invention, a non-MUC1 sequence is used in place of (instead of) a MUC1 signal sequence, such as any of the N-terminal synthetic and yeast-derived peptides described below for use with a fusion protein of the invention.

A MUC1 sea urchin sperm protein, enterokinase and agrin (SEA) domain useful in a fusion protein described above or elsewhere herein can be an SEA domain, or a portion thereof that includes at least one immunogenic domain, from any MUC1 protein, and in one aspect, is from a human MUC1 protein. In one aspect of the invention, a portion of the MUC1 SEA domain useful in a fusion protein of the invention comprises at least amino acid sequence from the extracellular domain (ED) of MUC1, but can exclude sequence upstream of the ED domain. In one aspect of the invention, the MUC1 SEA domain used in a fusion protein of the invention has an amino acid sequence comprising or consisting of an amino acid sequence selected from: positions 55-170 or positions 116-170 of SEQ ID NO:2 or at least one immunogenic domain thereof, positions 45-161 or positions 107-161 of SEQ ID NO:4 or at least one immunogenic domain thereof, positions 45-161 or positions 107-161 of SEQ ID NO:6 or at least one immunogenic domain thereof, positions 36-152 or positions 98-152 of SEQ ID NO:8 or at least one immunogenic domain thereof, positions 1034-1152 or positions 1098-1152 of SEQ ID NO:11 or at least one immunogenic domain thereof, positions 31-86 of SEQ ID NO:14 or at least one immunogenic domain thereof, positions 1-56 of SEQ ID NO:15 or at least one immunogenic domain thereof, a corresponding sequence from a different MUC1 protein such as another human MUC1 protein, or an amino acid sequence that is at least 95% identical, at least 96% identical, at least 97% identical, at least 98% identical, or at least 99% identical, to any one of these amino acid sequences.

A MUC1 extracellular domain (ED) useful in a fusion protein described above or elsewhere herein can be an ED or a portion thereof that includes at least one immunogenic domain from any MUC1 protein, and in one aspect, is from a human MUC1 protein. In one aspect of the invention, the MUC1 ED used in a fusion protein of the invention has an amino acid sequence comprising or consisting of an amino acid sequence selected from: positions 116-173 of SEQ ID NO:2 or at least one immunogenic domain thereof, positions 107-164 of SEQ ID NO:4 or at least one immunogenic domain thereof, positions 107-164 of SEQ ID NO:6 or at least one immunogenic domain thereof, positions 98-155 of SEQ ID NO:8 or at least one immunogenic domain thereof, positions 1098-1155 of SEQ ID NO:11 or at least one immunogenic domain thereof, positions 32-89 of SEQ ID NO:14 or at least one immunogenic domain thereof, positions 2-59 of SEQ ID NO:15 or at least one immunogenic domain thereof, a corresponding sequence from a different MUC1 protein such as another human MUC1 protein, or an amino acid sequence that is at least 95% identical, at least 96% identical, at least 97% identical, at least 98% identical, or at least 99% identical, to any one of these amino acid sequences.

A MUC1 single variable number of tandem repeat (VNTR) domain useful in a fusion protein described above or elsewhere herein can be a VNTR domain from any MUC1 protein, and in one aspect, is from a human MUC1 protein. In one aspect of the invention, the MUC1 VNTR domain used in a fusion protein of the invention has an amino acid sequence comprising or consisting of an amino acid sequence selected from: positions 126-145 of SEQ ID NO:11, any consecutive 20 amino acids between positions 61 and 1020 of SEQ ID NO:11 or any consecutive 20 amino acids between positions 126 and 965 of SEQ ID NO:11; SEQ ID NO:12 (including any of the polymorphisms within SEQ ID NO:12 as described above), any consecutive 20 amino acids between positions 90 and 130 of SEQ ID NO:14, any consecutive 20 amino acids between positions 60 and 100 of SEQ ID NO:15, a corresponding VNTR sequence from a different MUC1 protein such as another human MUC1 protein, or an amino acid sequence that is at least 95% identical, at least 96% identical, at least 97% identical, at least 98% identical, or at least 99% identical, to any one of these amino acid sequences.

A MUC1 transmembrane (TM) domain useful in a fusion protein described above or elsewhere herein can be a TM domain or a portion thereof that includes at least one immunogenic domain from any MUC1 protein, and in one aspect, is from a human MUC1 protein. In one aspect of the invention, the MUC1 TM domain used in a fusion protein of the invention has an amino acid sequence comprising or consisting of an amino acid sequence selected from: positions 174-201 of SEQ ID NO:2 or at least one immunogenic domain thereof, positions 165-192 of SEQ ID NO:4 or at least one immunogenic domain thereof, positions 165-192 of SEQ ID NO:6 or at least one immunogenic domain thereof, positions 156-183 of SEQ ID NO:8 or at least one immunogenic domain thereof, positions 1156-1183 of SEQ ID NO:11 or at least one immunogenic domain thereof, positions 131-158 of SEQ ID NO:14 or at least one immunogenic domain thereof, positions 101-128 of SEQ ID NO:15 or at least one immunogenic domain thereof, a corresponding sequence from a different MUC1 protein such as another human MUC1 protein, or an amino acid sequence that is at least 95% identical, at least 96% identical, at least 97% identical, at least 98% identical, or at least 99% identical, to any one of these amino acid sequences.

A MUC1 cytoplasmic domain (CD) useful in a fusion protein described above or elsewhere herein can be a CD or a portion thereof that includes at least one immunogenic domain from any MUC1 protein, and in one aspect, is from a human MUC1 protein. In one aspect of the invention, the MUC1 CD used in a fusion protein of the invention has an amino acid sequence comprising or consisting of an amino acid sequence selected from: positions 202-273 of SEQ ID NO:2 or at least one immunogenic domain thereof, positions 193-264 of SEQ ID NO:4 or at least one immunogenic domain thereof, positions 193-264 of SEQ ID NO:6 or at least one immunogenic domain thereof, positions 184-255 of SEQ ID NO:8 or at least one immunogenic domain thereof, positions 1184-1255 of SEQ ID NO:11 or at least one immunogenic domain thereof, positions 159-230 of SEQ ID NO:14 or at least one immunogenic domain thereof, positions 129-200 of SEQ ID NO:15 or at least one immunogenic domain thereof, positions 7-78 or positions 79-150 or positions 151-222 of SEQ ID NO:17 or at least one immunogenic domain thereof; positions 1-72 or positions 73-144 or positions 145-216 of SEQ ID NO:18 or an immunogenic domain thereof, a corresponding sequence from a different MUC1 protein such as another human MUC1 protein, or an amino acid sequence that is at least 95% identical, at least 96% identical, at least 97% identical, at least 98% identical, or at least 99% identical, to any one of these amino acid sequences.

In one embodiment of the invention, a fusion protein useful in a yeast-based immunotherapeutic composition of the invention includes the following MUC1 antigens, in the following order from N- to C-terminus: (1) a portion of a MUC1 SEA domain and MUC1 extracellular domain (ED) that includes most or all of the MUC1 ED; (2) at least two VNTR domains; (3) a MUC1 transmembrane domain; and (4) a MUC1 cytoplasmic domain (CD). In one embodiment, the fusion protein includes the following MUC1 antigens, in the following order from N- to C-terminus: (1) a MUC1 signal sequence; (2) a portion of a MUC1 SEA domain and MUC1 extracellular domain (ED) that includes most or all of the MUC1 ED; (3) at least two VNTR domains; (4) a MUC1 transmembrane domain; and (5) a MUC1 cytoplasmic domain (CD). Additional or alternate elements to be included in a fusion protein of the invention may include N-terminal and/or C-terminal peptides that improve or assist with the expression or stability of, and/or allow for identification and/or purification of, the fusion protein, and/or short intervening linker sequences (e.g., 1, 2, 3, 4, or 5 amino acid peptides) between segments of the fusion protein which can be useful for the introduction of restriction enzyme sites to facilitate cloning, as cleavage sites for host phagosomal proteases, to accelerate protein or antigen processing, and for future manipulation of the constructs. Such elements are described in detail below.

One example of such a fusion protein that is useful in a yeast-based immunotherapeutic composition of the invention comprises or includes the following MUC1 antigens, in the following order from N- to C-terminus:

(1) a MUC1 extracellular domain (ED) that may be appended at the N-terminus by one, two, three, four, five or more flanking amino acids from the non-ED portion of the SEA domain that reside upstream of the ED in the wild-type protein, wherein the ED segment comprises or consists of an amino acid sequence selected from: positions 116-173 of SEQ ID NO:2; or positions 107-164 of SEQ ID NO:4; positions 107-164 of SEQ ID NO:6; positions 98-155 of SEQ ID NO:8; positions 1098-1155 of SEQ ID NO:11; positions 32-89 of SEQ ID NO:14; positions 2-59 of SEQ ID NO:15; a corresponding sequence from a different MUC1 protein such as another human MUC1 protein; or an amino acid sequence that is at least 95% identical, at least 96% identical, at least 97% identical, at least 98% identical, or at least 99% identical, to any one of these amino acid sequences;

(2) at least two VNTR domains, wherein each of the VNTR domains comprise or consist of an amino acid sequence selected from: positions 126-145 of SEQ ID NO:11, any consecutive 20 amino acids between positions 61 and 1020 of SEQ ID NO:11 or any consecutive 20 amino acids between positions 126 and 965 of SEQ ID NO:11; SEQ ID NO:12 (including any of the polymorphisms within SEQ ID NO:12 as described above), any consecutive 20 amino acids between positions 90 and 130 of SEQ ID NO:14, any consecutive 20 amino acids between positions 60 and 100 of SEQ ID NO:15, a corresponding VNTR sequence from a different MUC1 protein such as another human MUC1 protein, or an amino acid sequence that is at least 95% identical, at least 96% identical, at least 97% identical, at least 98% identical, or at least 99% identical, to any one of these amino acid sequences;

(3) a MUC1 transmembrane (TM) domain, wherein the TM domain comprises or consists of an amino acid sequence selected from: positions 174-201 of SEQ ID NO:2, positions 165-192 of SEQ ID NO:4, positions 165-192 of SEQ ID NO:6, positions 156-183 of SEQ ID NO:8, positions 1156-1183 of SEQ ID NO:11, positions 131-158 of SEQ ID NO:14, positions 101-128 of SEQ ID NO:15, a corresponding sequence from a different MUC1 protein such as another human MUC1 protein, or an amino acid sequence that is at least 95% identical, at least 96% identical, at least 97% identical, at least 98% identical, or at least 99% identical, to any one of these amino acid sequences; and (4) a MUC1 cytoplasmic domain (CD), wherein the CD comprises or consists of an amino acid sequence selected from: positions 202-273 of SEQ ID NO:2, positions 193-264 of SEQ ID NO:4, positions 193-264 of SEQ ID NO:6, positions 184-255 of SEQ ID NO:8, positions 1184-1255 of SEQ ID NO:11, positions 159-230 of SEQ ID NO:14, positions 129-200 of SEQ ID NO:15, positions 7-78 or positions 79-150 or positions 151-222 of SEQ ID NO:17; positions 1-72 or positions 73-144 or positions 145-216 of SEQ ID NO:18, a corresponding sequence from a different MUC1 protein such as another human MUC1 protein, or an amino acid sequence that is at least 95% identical, at least 96% identical, at least 97% identical, at least 98% identical, or at least 99% identical, to any one of these amino acid sequences.

In one aspect of this embodiment, a fusion protein that is useful in a yeast-based immunotherapeutic composition of the invention comprises or consists of the amino acid sequence of SEQ ID NO:14 or SEQ ID NO:15. SEQ ID NO:14 includes the following MUC1 antigens, in the following order from N- to C-terminus: (1) a MUC1 signal sequence (positions 1-30 of SEQ ID NO:14); (2) a MUC1 SEA/ED segment (positions 31-89 of SEQ ID NO:14); (3) a VNTR segment comprising two VNTR domains (positions 90-130 of SEQ ID NO:14); (4) a MUC1 TM domain (positions 131-158 of SEQ ID NO:14); (5) a MUC1 CD (positions 159-230 of SEQ ID NO:14); and (6) a hexapeptide histidine tag (positions 231-236 of SEQ ID NO:14). SEQ ID NO:14 is encoded by the nucleotide sequence represented by SEQ ID NO:13. SEQ ID NO:15 includes the following MUC1 antigens, in the following order from N- to C-terminus: (1) a MUC1 SEA/ED segment (positions 1-59 of SEQ ID NO:15); (2) a VNTR segment comprising two VNTR domains (positions 60-100 of SEQ ID NO:15); (3) a MUC1 TM domain (positions 101-128 of SEQ ID NO:15); and (4) a MUC1 CD (positions 129-200 of SEQ ID NO:15). Optionally, the fusion protein of SEQ ID NO:14 or SEQ ID NO:15 includes an N-terminal peptide that is a synthetic N-terminal peptide designed to impart resistance to proteasomal degradation and stabilize expression represented by SEQ ID NO:21, or an N-terminal peptide from a yeast alpha leader sequence such as SEQ ID NO:19 or SEQ ID NO:20, or another N-terminal peptide suitable for use with a yeast-based immunotherapeutic as described herein. Also optionally, one or more linker peptides of from one, two, three or more amino acids, such as the two amino acid linker of Thr-Ser, can be inserted between segments of the fusion protein. The hexahistidine tag at the C-terminus of the fusion protein is also optional.

In one embodiment of the invention, a fusion protein useful in a yeast-based immunotherapeutic composition of the invention includes the following MUC1 antigens, in the following order from N- to C-terminus: (1) at least two VNTR domains; and (2) a portion of a MUC1 SEA domain and MUC1 extracellular domain (ED) that includes most or all of the MUC1 ED. Such a fusion protein may include additional portions of the MUC1-N region flanking the VNTR domains. Such a fusion protein does not include an entire MUC1-N subunit.

In another embodiment of the invention, a fusion protein useful in a yeast-based immunotherapeutic composition of the invention includes the following MUC1 antigens, in the following order from N- to C-terminus: (1) a first MUC1 cytoplasmic domain (CD); (2) a second MUC1 cytoplasmic domain (CD); and (3) a third MUC1 cytoplasmic domain (CD). In one embodiment, additional MUC1 cytoplasmic domains can be included in such a fusion protein. In one embodiment, at least one of the MUC1 CDs is from a different source than one of the other MUC1 CDs (e.g., one MUC1 CD is from a first human MUC1 protein and one MUC1 CD is from a second MUC1 protein, wherein there can be sequence differences between the first and second MUC1 CDs). In one embodiment, this fusion protein is appended at the N-terminus with a MUC1 signal sequence. In another embodiment, this fusion protein may include N-terminal and/or C-terminal peptides that improve or assist with the expression or stability of, and/or allow for identification and/or purification of, the fusion protein, and/or short intervening linker sequences (e.g., 1, 2, 3, 4, or 5 amino acid peptides) between segments of the fusion protein which can be useful for the introduction of restriction enzyme sites to facilitate cloning, as cleavage sites for host phagosomal proteases, to accelerate protein or antigen processing, and for future manipulation of the constructs.

One example of such a fusion protein that is useful in a yeast-based immunotherapeutic composition of the invention comprises or includes the following MUC1 antigens, in the following order from N- to C-terminus:

(1) a first MUC1 cytoplasmic domain (CD), wherein the CD comprises or consists of an amino acid sequence selected from: positions 202-273 of SEQ ID NO:2, positions 193-264 of SEQ ID NO:4, positions 193-264 of SEQ ID NO:6, positions 184-255 of SEQ ID NO:8, positions 1184-1255 of SEQ ID NO:11, positions 159-230 of SEQ ID NO:14, positions 129-200 of SEQ ID NO:15, positions 7-78 or positions 79-150 or positions 151-222 of SEQ ID NO:17; positions 1-72 or positions 73-144 or positions 145-216 of SEQ ID NO:18, a corresponding sequence from a different MUC1 protein such as another human MUC1 protein, or an amino acid sequence that is at least 95% identical, at least 96% identical, at least 97% identical, at least 98% identical, or at least 99% identical, to any one of these amino acid sequences;

(2) a second MUC1 cytoplasmic domain (CD), wherein the CD comprises or consists of an amino acid sequence selected from: positions 202-273 of SEQ ID NO:2, positions 193-264 of SEQ ID NO:4, positions 193-264 of SEQ ID NO:6, positions 184-255 of SEQ ID NO:8, positions 1184-1255 of SEQ ID NO:11, positions 159-230 of SEQ ID NO:14, positions 129-200 of SEQ ID NO:15, positions 7-78 or positions 79-150 or positions 151-222 of SEQ ID NO:17; positions 1-72 or positions 73-144 or positions 145-216 of SEQ ID NO:18, a corresponding sequence from a different MUC1 protein such as another human MUC1 protein, or an amino acid sequence that is at least 95% identical, at least 96% identical, at least 97% identical, at least 98% identical, or at least 99% identical, to any one of these amino acid sequences;

(3) a third MUC1 cytoplasmic domain (CD), wherein the CD comprises or consists of an amino acid sequence selected from: positions 202-273 of SEQ ID NO:2, positions 193-264 of SEQ ID NO:4, positions 193-264 of SEQ ID NO:6, positions 184-255 of SEQ ID NO:8, positions 1184-1255 of SEQ ID NO:11, positions 159-230 of SEQ ID NO:14, positions 129-200 of SEQ ID NO:15, positions 7-78 or positions 79-150 or positions 151-222 of SEQ ID NO:17; positions 1-72 or positions 73-144 or positions 145-216 of SEQ ID NO:18, a corresponding sequence from a different MUC1 protein such as another human MUC1 protein, or an amino acid sequence that is at least 95% identical, at least 96% identical, at least 97% identical, at least 98% identical, or at least 99% identical, to any one of these amino acid sequences.

In one aspect of this embodiment, a fusion protein that is useful in a yeast-based immunotherapeutic composition of the invention comprises or consists of the amino acid sequence of SEQ ID NO:17 or SEQ ID NO:18. SEQ ID NO:17 includes the following MUC1 antigens, in the following order from N- to C-terminus: (1) an synthetic peptide represented by SEQ ID NO:21 (positions 1-6 of SEQ ID NO:17); (2) a first MUC1 CD (positions 7-78 of SEQ ID NO:17); (3) a second MUC1 CD (positions 79-150 of SEQ ID NO:17); (4) a third MUC1 CD (positions 151-222 of SEQ ID NO:17); and (5) a hexahistidine tag (positions 223-228 of SEQ ID NO:17). SEQ ID NO:17 is encoded by the nucleotide sequence represented by SEQ ID NO:16. SEQ ID NO:18 includes the following MUC1 antigens, in the following order from N- to C-terminus: (1) a first MUC1 CD (positions 1-72 of SEQ ID NO:18); (2) a second MUC1 CD (positions 73-144 of SEQ ID NO:18); (3) a third MUC1 CD (positions 145-216 of SEQ ID NO:18). Optionally, the fusion protein of SEQ ID NO:17 or SEQ ID NO:18 includes an N-terminal peptide that is a synthetic N-terminal peptide designed to impart resistance to proteasomal degradation and stabilize expression represented by SEQ ID NO:21, or an N-terminal peptide from a yeast alpha leader sequence such as SEQ ID NO:19 or SEQ ID NO:20, or another N-terminal peptide suitable for use with a yeast-based immunotherapeutic as described herein. Also optionally, one or more linker peptides of from one to three or more amino acids linker sequences of one, two, three or more amino acids, such as the two amino acid linker of Thr-Ser can be inserted between segments of the fusion protein. The hexahistidine tag at the C-terminus of the fusion protein is also optional.

A MUC1 antigen useful in the present invention also includes proteins having an amino acid sequence that is at least 85%, 86%, 87%, 88%, 89%, 90%, 91%, 92%, 93%, 94%, 95%, 96%, 97%, 98%, or 99% identical to the amino acid sequence of any of the MUC1 proteins, domains, fusion proteins, or antigens described herein over the full length of the protein, or with respect to a defined fragment or domain thereof (e.g., an immunological domain or functional domain (domain with at least one biological activity)) that forms part of the protein. For example, a domain of the MUC1 protein described herein includes the signal sequence, a VNTR domain, an SEA domain, the extracellular domain (ED), an TM domain, and/or a cytoplasmic domain (CD). An immunological domain has been described in detail above. MUC1 fusion proteins described herein include those represented by SEQ ID NO:14, SEQ ID NO:15, SEQ ID NO:17 and SEQ ID NO:18. Accordingly, a MUC1 antigen useful in the yeast-based immunotherapeutic of the invention includes a MUC1 antigen comprising or consisting of any one of SEQ ID NO:14, SEQ ID NO:15, SEQ ID NO:17 and SEQ ID NO:18, an amino acid sequence that is at least about 95%, 96%, 97%, 98% or 99% identical to any one of SEQ ID NO:14, SEQ ID NO:15, SEQ ID NO:17 and SEQ ID NO:18, and/or a corresponding sequence from a different MUC1 protein (e.g., a fusion protein where one or more of the fusion segments are from the corresponding sequences from a different MUC1 protein or from a MUC1 protein agonist sequence, such that minor sequence differences may be present as compared to the sequences presented here).

It is straightforward to use the corresponding portions of any of the MUC1 proteins or domains derived or obtained from sequence or sources other than those exemplified herein, and particularly from sequences or sources within the same animal species, to create fusion proteins having a similar or the same overall structure as the fusion proteins described herein. By way of example, one can readily identify a corresponding sequence in given human MUC1 protein from any source that corresponds to positions 1034-1152 of SEQ ID NO:11, using simple sequence alignment tools or processes. Therefore, sequences with minor and/or conservative differences from the sequences exemplified herein are expressly encompassed by the present invention.

In some aspects of the invention, amino acid insertions, deletions, and/or substitutions can be made for one, two, three, four, five, six, seven, eight, nine, ten, eleven, or more amino acids of a wild-type or reference MUC1 protein, provided that the resulting MUC1 protein, when used as an antigen in a Yeast-MUC1 immunotherapeutic composition of the invention, elicits an immune response against a native MUC1 protein as the wild-type or reference MUC1 protein, which may include an enhanced immune response, a diminished immune response, or a substantially similar immune response. For example, the invention includes the use of MUC1 agonist antigens, which may include one or more T cell epitopes that have been mutated to enhance the T cell response against the MUC1 agonist, such as by improving the avidity or affinity of the epitope for an MHC molecule or for the T cell receptor that recognizes the epitope in the context of MHC presentation. MUC1 agonists may therefore improve the potency or efficiency of a T cell response against native MUC1 expressed by a tumor cell. A variety of MUC1 T cell epitopes, including agonist epitopes are described in U.S. Pat. Nos. 6,546,643; 7,118,738; 7,342,094; 7,696,306; and U.S. Patent Application Publication No. 2008/0063653, and any one or more of these epitopes can be used in a MUC1 antigen of the present invention, including by adding, deleting or substituting one or more amino acids within a sequence described herein to conform the sequence to the published epitope sequence at that position(s).

Examples of MUC1 agonist antigens are provided herein (see Examples 3 and 4). In one embodiment, a MUC1 agonist antigen suitable for use in the present invention comprises 1, 2, 3, 4, 5, 6, 7, 8, 9, 10, or all 11 of the following substitutions, where the positions of the substitutions are provided with respect to a wild-type MUC1 represented by Accession No. NP_001191214 (although the same or equivalent positions can be readily identified in any other wild-type MUC1 sequence): T93, A161, P162, G169, S170, T171, A392, C406, T444, D445, or S460. In one embodiment, a MUC1 agonist antigen that is useful in a yeast-based immunotherapeutic composition of the invention comprises or consists of the amino acid sequence of SEQ ID NO:23 or SEQ ID NO:25. SEQ ID NO:23 includes the following MUC1 antigens, in the following order from N- to C-terminus: (1) MUC1 signal sequence (positions 1-30 of SEQ ID NO:23); (2) a MUC1 SEA/ED segment (positions 31-89 of SEQ ID NO:23); (3) a VNTR segment comprising two VNTR domains (positions 90-130 of SEQ ID NO:23); (4) a MUC1 TM domain (positions 131-158 of SEQ ID NO:23); (5) a MUC1 CD (positions 159-230 of SEQ ID NO:23); (6) a MUC1 agonist epitope (positions 231-246 of SEQ ID NO:23) and (7) a hexapeptide histidine tag (positions 247-252 of SEQ ID NO:23). SEQ ID NO:23 is encoded by the nucleotide sequence represented by SEQ ID NO:22 (codon optimized for yeast expression). The MUC1 signal sequence (positions 1-30 of SEQ ID NO:23) could be substituted with a different N-terminal sequence designed to impart resistance to proteasomal degradation and/or stabilize expression, such as the peptide represented by SEQ ID NO:21, or an N-terminal peptide from a yeast alpha leader sequence such as SEQ ID NO:19 or SEQ ID NO:20. hexahistidine C-terminal tag is optional, and facilitates identification and/or purification of the protein. As compared to the MUC1 antigen in SEQ ID NO:14 or SEQ ID NO:15, the SEQ ID NO:23 contains the following amino acid substitutions to create a variety of agonist epitopes (substitution positions given with reference to SEQ ID NO:23, with further reference to the location of the substitution in a wild-type MUC1 represented by Accession No. NP_001191214): A96Y (position 161 in wild-type MUC1), P97L (position 162 in wild-type MUC1), G104V (position 169 in wild-type MUC1), S105Y (position 170 in wild-type MUC1), T106L (position 171 in wild-type MUC1), A147Y (position 392 in wild-type MUC1), C161V (position 406 in wild-type MUC1), T199L (position 444 in wild-type MUC1), D200F (position 445 in wild-type MUC1), S215Y (position 460 in wild-type MUC1), and T239L (position 93 in wild-type MUC1).

SEQ ID NO:25 includes the following MUC1 antigens, in the following order from N- to C-terminus: (1) an alpha factor leader sequence disclosed elsewhere herein by SEQ ID NO:19 (positions 1-89 of SEQ ID NO:25); (2) a linker sequence of Thr-Ser (positions 90-91 of SEQ ID NO:25); (3) a full-length MUC1 agonist protein corresponding to a wild-type protein except for the introduction of 11 agonist epitopes (positions 92-566 of SEQ ID NO:25) and (7) a hexapeptide histidine tag (positions 567-572 of SEQ ID NO:25). SEQ ID NO:25 is encoded by the nucleotide sequence represented by SEQ ID NO:24 (codon optimized for yeast expression). The alpha leader sequence (positions 1-89 of SEQ ID NO:25) could be substituted with a different N-terminal sequence designed to impart resistance to proteasomal degradation and/or stabilize expression, such as the peptide represented by SEQ ID NO:21, or an N-terminal peptide from a different yeast alpha leader sequence such as SEQ ID NO:20, or by a MUC1 signal sequence. The hexahistidine C-terminal tag is optional, and facilitates identification and/or purification of the protein. As compared to the wild-type MUC1 protein used as a template, the sequence in GI-6106 contains the following amino acid substitutions to create a variety of agonist epitopes (substitution positions given with reference to SEQ ID NO:25, with further reference to the location of the substitution in a wild-type MUC1 represented by Accession No. NP_001191214): T184L (position 93 in wild-type MUC1), A232Y (position 161 in wild-type MUC1), P233L (position 162 in wild-type MUC1), G240V (position 169 in wild-type MUC1), S241Y (position 170 in wild-type MUC1), T242L (position 171 in wild-type MUC1), A483Y (position 392 in wild-type MUC1), C497V (position 406 in wild-type MUC1), T535L (position 444 in wild-type MUC1), D536F (position 445 in wild-type MUC1), and S551Y (position 460 in wild-type MUC1).

Accordingly, a MUC1 agonist antigen useful in the yeast-based immunotherapeutic of the invention includes a MUC1 antigen comprising or consisting of SEQ ID NO:23 or SEQ ID NO:25, or the MUC1-specific sequences within these larger fusion proteins, or an amino acid sequence that is at least about 95%, 96%, 97%, 98% or 99% identical to any one of SEQ ID NO:23, SEQ ID NO:25, or the MUC1-specific sequences within these larger fusion proteins, and/or a corresponding sequence from a different MUC1 protein (e.g., a fusion protein where one or more of the fusion segments are from the corresponding sequences from a different MUC1 protein, such that minor sequence differences may be present as compared to the sequences presented here).

As discussed above, N-terminal expression sequences and the C-terminal tags, such as those described above with respect to the fusion proteins of SEQ ID NO:14, SEQ ID NO:17, SEQ ID NO:23, or SEQ ID NO:25 are optional, but may be selected from several different sequences described elsewhere herein to improve or assist with expression, stability, and/or allow for identification and/or purification of the protein. Also, many different promoters suitable for use in yeast are known in the art. Furthermore, short intervening linker sequences (e.g., 1, 2, 3, 4, or 5 amino acid peptides) may be introduced between portions of a fusion protein comprising a MUC1 antigen for a variety of reasons, including the introduction of restriction enzyme sites to facilitate cloning, as cleavage sites for host phagosomal proteases, to accelerate protein or antigen processing, and for future manipulation of the constructs.

Optionally, proteins, including fusion proteins, which are used as a component of the Yeast-MUC1 immunotherapeutic composition of the invention are produced using antigen constructs that are particularly useful for improving or stabilizing the expression of heterologous antigens in yeast. In one embodiment, the desired antigenic protein(s) or peptide(s) are fused at their amino-terminal end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, wherein either fusion partner provides improved stability of expression of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, described in more detail herein). In addition, the present invention optionally includes the use of peptides that are fused to the C-terminus of the antigen-encoding construct, particularly for use in the selection and identification of the protein. Such peptides include, but are not limited to, any synthetic or natural peptide, such as a peptide tag (e.g., 6×His or hexapeptide) or any other short epitope tag. Peptides attached to the C-terminus of an antigen according to the invention can be used with or without the addition of the N-terminal peptides discussed above, and vice versa.

In one embodiment, a synthetic peptide useful in a fusion protein to be expressed in a yeast is linked to the N-terminus of the antigen, the peptide consisting of at least two amino acid positions that are heterologous to the antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid positions at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-6 of the fusion protein is a lysine or an arginine (i.e., the amino acids at positions 2-6, whether part of the synthetic peptide or the protein, if the synthetic peptide is shorter than 5 amino acids, do not include a lysine or an arginine). The synthetic peptide can be as short as two amino acids, but in one aspect, is 2-6 amino acids (including 3, 4, 5 amino acids), and can be longer than 6 amino acids, in whole integers, up to about 200 amino acids, 300 amino acids, 400 amino acids, 500 amino acids, or more.

In one embodiment, a fusion protein comprises an amino acid sequence of M-X2-X3-X4-X5-X6, wherein M is methionine; wherein X2 is any amino acid except glycine, proline, lysine or arginine; wherein X3 is any amino acid except methionine, lysine or arginine; wherein X4 is any amino acid except methionine, lysine or arginine; wherein X5 is any amino acid except methionine, lysine or arginine; and wherein X6 is any amino acid except methionine, lysine or arginine. In one embodiment, the X6 residue is a proline. An exemplary synthetic sequence that enhances the stability of expression of an antigen in a yeast cell and/or prevents post-translational modification of the protein in the yeast includes the sequence M-A-D-E-A-P (represented herein by SEQ ID NO:21). In addition to the enhanced stability of the expression product, this fusion partner does not appear to negatively impact the immune response against the immunizing antigen in the construct. In addition, the synthetic fusion peptides can be designed to provide an epitope that can be recognized by a selection agent, such as an antibody.

In one embodiment, the MUC1 antigen is linked at the N-terminus to a yeast protein, such as an alpha factor prepro sequence (also referred to as the alpha factor signal leader sequence, the amino acid sequence of which is exemplified herein by SEQ ID NO:19 or SEQ ID NO:20 Other sequences for yeast alpha factor prepro sequence are known in the art and are encompassed for use in the present invention.

In one aspect of the invention, the yeast vehicle is manipulated such that the antigen is expressed or provided by delivery or translocation of an expressed protein product, partially or wholly, on the surface of the yeast vehicle (extracellular expression). One method for accomplishing this aspect of the invention is to use a spacer arm for positioning one or more protein(s) on the surface of the yeast vehicle. For example, one can use a spacer arm to create a fusion protein of the antigen(s) or other protein of interest with a protein that targets the antigen(s) or other protein of interest to the yeast cell wall. For example, one such protein that can be used to target other proteins is a yeast protein (e.g., cell wall protein 2 (cwp2), Aga2, Pir4 or Flo1 protein) that enables the antigen(s) or other protein to be targeted to the yeast cell wall such that the antigen or other protein is located on the surface of the yeast. Proteins other than yeast proteins may be used for the spacer arm; however, for any spacer arm protein, it is most desirable to have the immunogenic response be directed against the target antigen rather than the spacer arm protein. As such, if other proteins are used for the spacer arm, then the spacer arm protein that is used should not generate such a large immune response to the spacer arm protein itself such that the immune response to the target antigen(s) is overwhelmed. One of skill in the art should aim for a small immune response to the spacer arm protein relative to the immune response for the target antigen(s). Spacer arms can be constructed to have cleavage sites (e.g., protease cleavage sites) that allow the antigen to be readily removed or processed away from the yeast, if desired. Any known method of determining the magnitude of immune responses can be used (e.g., antibody production, lytic assays, etc.) and are readily known to one of skill in the art.

Another method for positioning the target antigen(s) or other proteins to be exposed on the yeast surface is to use signal sequences such as glycosylphosphatidyl inositol (GPI) to anchor the target to the yeast cell wall. Alternatively, positioning can be accomplished by appending signal sequences that target the antigen(s) or other proteins of interest into the secretory pathway via translocation into the endoplasmic reticulum (ER) such that the antigen binds to a protein which is bound to the cell wall (e.g., cwp).

In one aspect, the spacer arm protein is a yeast protein. The yeast protein can consist of between about two and about 800 amino acids of a yeast protein. In one embodiment, the yeast protein is about 10 to 700 amino acids. In another embodiment, the yeast protein is about 40 to 600 amino acids. Other embodiments of the invention include the yeast protein being at least 250 amino acids, at least 300 amino acids, at least 350 amino acids, at least 400 amino acids, at least 450 amino acids, at least 500 amino acids, at least 550 amino acids, at least 600 amino acids, or at least 650 amino acids. In one embodiment, the yeast protein is at least 450 amino acids in length. Another consideration for optimizing antigen surface expression, if that is desired, is whether the antigen and spacer arm combination should be expressed as a monomer or as dimer or as a trimer, or even more units connected together. This use of monomers, dimers, trimers, etc. allows for appropriate spacing or folding of the antigen such that some part, if not all, of the antigen is displayed on the surface of the yeast vehicle in a manner that makes it more immunogenic.

Use of yeast proteins can stabilize the expression of fusion proteins in the yeast vehicle, prevents posttranslational modification of the expressed fusion protein, and/or targets the fusion protein to a particular compartment in the yeast (e.g., to be expressed on the yeast cell surface). For delivery into the yeast secretory pathway, exemplary yeast proteins to use include, but are not limited to: Aga (including, but not limited to, Aga1 and/or Aga2); SUC2 (yeast invertase); alpha factor signal leader sequence; CPY; Cwp2p for its localization and retention in the cell wall; BUD genes for localization at the yeast cell bud during the initial phase of daughter cell formation; Flo1p; Pir2p; and Pir4p.

Other sequences can be used to target, retain and/or stabilize the protein to other parts of the yeast vehicle, for example, in the cytosol or the mitochondria or the endoplasmic reticulum or the nucleus. Examples of suitable yeast protein that can be used for any of the embodiments above include, but are not limited to, TK, AF, SECT; phosphoenolpyruvate carboxykinase PCK1, phosphoglycerokinase PGK and triose phosphate isomerase TPI gene products for their repressible expression in glucose and cytosolic localization; the heat shock proteins SSA1, SSA3, SSA4, SSC1, whose expression is induced and whose proteins are more thermostable upon exposure of cells to heat treatment; the mitochondrial protein CYC1 for import into mitochondria; ACT1.

Methods of producing yeast vehicles and expressing, combining and/or associating yeast vehicles with antigens and/or other proteins and/or agents of interest to produce yeast-based immunotherapy compositions are contemplated by the invention.

According to the present invention, the term "yeast vehicle-antigen complex" or "yeast-antigen complex" is used generically to describe any association of a yeast vehicle with an antigen, and can be used interchangeably with "yeast-based immunotherapy composition" when such composition is used to elicit an immune response as described above. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transfected with a heterologous nucleic acid molecule encoding a protein (e.g., the antigen) such that the protein is expressed by the yeast cell. Such a yeast is also referred to herein as a recombinant yeast or a recombinant yeast vehicle. The yeast cell can then be formulated with a pharmaceutically acceptable excipient and administered directly to a patient, stored for later administration, or loaded into a dendritic cell as an intact cell. The yeast cell can also be killed, or it can be derivatized such as by formation of yeast spheroplasts, cytoplasts, ghosts, or subcellular particles, any of which may be followed by storing, administering, or loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses the antigen. Yeast cells or yeast spheroplasts that recombinantly express the antigen(s) may be used to produce a yeast vehicle comprising a yeast cytoplast, a yeast ghost, or a yeast membrane particle or yeast cell wall particle, or fraction thereof.

In general, the yeast vehicle and antigen(s) and/or other agents can be associated by any technique described herein. In one aspect, the yeast vehicle was loaded intracellularly with the antigen(s) and/or agent(s). In another aspect, the antigen(s) and/or agent(s) was covalently or non-covalently attached to the yeast vehicle. In yet another aspect, the yeast vehicle and the antigen(s) and/or agent(s) were associated by mixing. In another aspect, and in one embodiment, the antigen(s) and/or agent(s) are expressed recombinantly by the yeast vehicle or by the yeast cell or yeast spheroplast from which the yeast vehicle was derived.

A number of antigens and/or other proteins to be produced by a yeast vehicle of the present invention is any number of antigens and/or other proteins that can be reasonably produced by a yeast vehicle, and typically ranges from at least one to at least about 6 or more, including from about 2 to about 6 antigens and or other proteins.

Expression of an antigen or other protein in a yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GALT), UDP-galactose epimerase (GAL10), cytochrome c1 (CYC1), Sec7 protein (SECT) and acid phosphatase (PHOS), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GALT and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methylotrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule can be introduced into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

Effective conditions for the production of recombinant yeast vehicles and expression of the antigen and/or other protein by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, Methods in Enzymology, vol. 194, Academic Press, San Diego). For example, under one protocol, liquid cultures containing a suitable medium can be inoculated using cultures obtained from starter plates and/or starter cultures of Yeast-MUC1 immunotherapy compositions, and are grown for approximately 20 h at 30° C., with agitation at 250 rpm. Primary cultures can then be expanded into larger cultures as desired. Protein expression from vectors with which the yeast were transformed (e.g., MUC1 expression) may be constitutive if the promoter utilized is a constitutive promoter, or may be induced by addition of the appropriate induction conditions for the promoter if the promoter utilized is an inducible promoter (e.g., copper sulfate in the case of the CUP1 promoter). In the case of an inducible promoter, induction of protein expression may be initiated after the culture has grown to a suitable cell density, which may be at about 0.2 Y.U./ml or higher densities.

One non-limiting example of a medium suitable for the culture of a Yeast-MUC1 immunotherapy composition of the invention is U2 medium. U2 medium comprises the following components: 15 g/L of glucose, 6.7 g/L of Yeast nitrogen base containing ammonium sulfate, and 0.04 mg/mL each of histidine, tryptophan, and adenine, and 0.06 mg/ml of leucine. Another non-limiting example of a medium suitable for the culture of Yeast-MUC1 immunotherapy composition of the invention is UL2 medium. UL2 medium comprises the following components: 15 g/L of glucose, 6.7 g/L of Yeast nitrogen base containing ammonium sulfate, and 0.04 mg/mL each of histidine, tryptophan, and adenine.

In some embodiments of the invention, the yeast are grown under neutral pH conditions. As used herein, the general use of the term "neutral pH" refers to a pH range between about pH 5.5 and about pH 8, and in one aspect, between about pH 6 and about 8. One of skill the art will appreciate that minor fluctuations (e.g., tenths or hundredths) can occur when measuring with a pH meter. As such, the use of neutral pH to grow yeast cells means that the yeast cells are grown in neutral pH for the majority of the time that they are in culture. In one embodiment, yeast are grown in a medium maintained at a pH level of at least 5.5 (i.e., the pH of the culture medium is not allowed to drop below pH 5.5). In another aspect, yeast are grown at a pH level maintained at about 6, 6.5, 7, 7.5 or 8. In one aspect, neutral pH is maintained by using a suitable buffer to create a buffered culture or growth medium. The use of a neutral pH in culturing yeast promotes several biological effects that are desirable characteristics for using the yeast as vehicles for immunomodulation. For example, culturing the yeast in neutral pH allows for good growth of the yeast without negative effect on the cell generation time (e.g., slowing of doubling time). The yeast can continue to grow to high densities without losing their cell wall pliability. The use of a neutral pH allows for the production of yeast with pliable cell walls and/or yeast that are more sensitive to cell wall digesting enzymes (e.g., glucanase) at all harvest densities. This trait is desirable because yeast with flexible cell walls can induce different or improved immune responses as compared to yeast grown under more acidic conditions, e.g., by promoting the secretion of cytokines by antigen presenting cells that have phagocytosed the yeast (e.g., TH1-type cytokines including, but not limited to, IFN-γ, interleukin-12 (IL-12), and IL-2, as well as proinflammatory cytokines such as IL-6). In addition, greater accessibility to the antigens located in the cell wall is afforded by such culture methods. In another aspect, the use of neutral pH for some antigens allows for release of the di-sulfide bonded antigen by treatment with dithiothreitol (DTT) that is not possible when such an antigen-expressing yeast is cultured in media at lower pH (e.g., pH 5). In one non-limiting example of the use of neutral pH conditions to culture yeast for use in the present invention, UL2 medium described above is buffered using, for example, 4.2 g/L of Bis-Tris.

The inventors demonstrate herein that yeast-MUC1 immunotherapeutic compositions of the invention grown using neutral pH conditions are more potent activators of dendritic cells and activate MUC-1-specific T cells to produce higher levels of IFN-γ than the same yeast-MUC1 immunotherapeutic compositions grown under standard conditions (where neutral pH is not maintained) (see Examples).

In one embodiment, control of the amount of yeast glycosylation is used to control the expression of antigens by the yeast, particularly on the surface. The amount of yeast glycosylation can affect the immunogenicity and antigenicity of the antigen, particularly one expressed on the surface, since sugar moieties tend to be bulky. As such, the existence of sugar moieties on the surface of yeast and its impact on the three-dimensional space around the target antigen(s) should be considered in the modulation of yeast according to the invention. Any method can be used to reduce or increase the amount of glycosylation of the yeast, if desired. For example, one could use a yeast mutant strain that has been selected to have low glycosylation (e.g. mnn1, och1 and mnn9 mutants), or one could eliminate by mutation the glycosylation acceptor sequences on the target antigen. Alternatively, one could use yeast with abbreviated glycosylation patterns, e.g., *Pichia*. One can also treat the yeast using methods that reduce or alter the glycosylation.

In one embodiment of the present invention, as an alternative to expression of an antigen or other protein recombinantly in the yeast vehicle, a yeast vehicle is loaded intracellularly with the protein or peptide, or with carbohydrates or other molecules that serve as an antigen and/or are useful as immunomodulatory agents or biological response modifiers according to the invention. Subsequently, the yeast vehicle, which now contains the antigen and/or other proteins intracellularly, can be administered to an individual or loaded into a carrier such as a dendritic cell. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom. Any number of antigens and/or other agents can be loaded into a yeast vehicle in this embodiment, from at least 1, 2, 3, 4 or any whole integer up to hundreds or thousands of antigens and/or other agents, such as would be provided by the loading of a microorganism or portions thereof, for example.

In another embodiment of the present invention, an antigen and/or other agent is physically attached to the yeast vehicle. Physical attachment of the antigen and/or other agent to the yeast vehicle can be accomplished by any method suitable in the art, including covalent and non-covalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

When the antigen or other protein is expressed on or physically attached to the surface of the yeast, spacer arms may, in one aspect, be carefully selected to optimize antigen or other protein expression or content on the surface. The size of the spacer arm(s) can affect how much of the antigen or other protein is exposed for binding on the surface of the yeast. Thus, depending on which antigen(s) or other protein(s) are being used, one of skill in the art will select a spacer arm that effectuates appropriate spacing for the antigen or other protein on the yeast surface. In one embodiment, the spacer arm is a yeast protein of at least 450 amino acids. Spacer arms have been discussed in detail above.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

In one embodiment, intact yeast (with or without expression of heterologous antigens or other proteins) can be ground up or processed in a manner to produce yeast cell wall preparations, yeast membrane particles or yeast fragments (i.e., not intact) and the yeast fragments can, in some embodiments, be provided with or administered with other compositions that include antigens (e.g., DNA vaccines, protein subunit vaccines, killed or inactivated pathogens, viral vector vaccines) to enhance immune responses. For example, enzymatic treatment, chemical treatment or physical force (e.g., mechanical shearing or sonication) can be used to break up the yeast into parts that are used as an adjuvant.

In one embodiment of the invention, yeast vehicles useful in the invention include yeast vehicles that have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods. See, for example, the methodology disclosed in standard yeast culturing textbooks such as *Methods of Enzymology*, Vol. 194, Cold Spring Harbor Publishing (1990). Any of the inactivation strategies used should take the secondary, tertiary or quaternary structure of the target antigen into consideration and preserve such structure as to optimize its immunogenicity.

Yeast vehicles can be formulated into yeast-based immunotherapy compositions or products of the present invention using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

In one embodiment of the present invention, a composition can include additional agents, which may also be referred to as biological response modifier compounds, or the ability to produce such agents/modifiers. For example, a yeast vehicle can be transfected with or loaded with at least one antigen and at least one agent/biological response modifier compound, or a composition of the invention can be administered in conjunction with at least one agent/biological response modifier. Biological response modifiers include adjuvants and other compounds that can modulate immune responses, which may be referred to as immunomodulatory compounds, as well as compounds that modify the biological activity of another compound or agent, such as a yeast-based immunotherapeutic, such biological activity not being limited to immune system effects. Certain immunomodulatory compounds can stimulate a protective immune response whereas others can suppress a harmful immune response, and whether an immunomodulatory is useful in combination with a given yeast-based immunotherapeutic may depend, at least in part, on the disease state or condition to be treated or prevented, and/or on the individual who is to be treated. Certain biological response modifiers preferentially enhance a cell-mediated immune response whereas others preferentially enhance a humoral immune response (i.e., can stimulate an immune response in which there is an increased level of cell-mediated compared to humoral immunity, or vice versa.). Certain biological response modifiers have one or more properties in common with the biological properties of yeast-based immunotherapeutics or enhance or complement the biological properties of yeast-based immunotherapeutics. There are a number of techniques known to those skilled in the art to measure stimulation or suppression of immune responses, as well as to differentiate cell-mediated immune responses from humoral immune responses, and to differentiate one type of cell-mediated response from another (e.g., a TH17 response versus a TH1 response).

Agents/biological response modifiers useful in the invention may include, but are not limited to, cytokines, chemokines, hormones, lipidic derivatives, peptides, proteins, polysaccharides, small molecule drugs, antibodies and antigen binding fragments thereof (including, but not limited to, anti-cytokine antibodies, anti-cytokine receptor antibodies, anti-chemokine antibodies), vitamins, polynucleotides, nucleic acid binding moieties, aptamers, and growth modulators. Some suitable agents include, but are not limited to, IL-1 or agonists of IL-1 or of IL-1R, anti-IL-1 or other IL-1 antagonists; IL-6 or agonists of IL-6 or of IL-6R, anti-IL-6 or other IL-6 antagonists; IL-12 or agonists of IL-12 or of IL-12R, anti-IL-12 or other IL-12 antagonists; IL-17 or agonists of IL-17 or of IL-17R, anti-IL-17 or other IL-17 antagonists; IL-21 or agonists of IL-21 or of IL-21R, anti-IL-21 or other IL-21 antagonists; IL-22 or agonists of IL-22 or of IL-22R, anti-IL-22 or other IL-22 antagonists; IL-23 or agonists of IL-23 or of IL-23R, anti-IL-23 or other IL-23 antagonists; IL-25 or agonists of IL-25 or of IL-25R, anti-IL-25 or other IL-25 antagonists; IL-27 or agonists of IL-27 or of IL-27R, anti-IL-27 or other IL-27 antagonists; type I interferon (including IFN-α) or agonists or antagonists of type I interferon or a receptor thereof; type II interferon (including IFN-γ) or agonists or antagonists of type II interferon or a receptor thereof; anti-CD40, CD40L, lymphocyte-activation gene 3 (LAG3) protein and/or IMP321 (T-cell immunostimulatory factor derived from the soluble form of LAG3), anti-CTLA-4 antibody (e.g., to release anergic T cells); T cell co-stimulators (e.g., anti-CD137, anti-CD28, anti-CD40); alemtuzumab (e.g., CamPath®), denileukin diftitox (e.g., ONTAK®); anti-CD4; anti-CD25; anti-PD-1, anti-PD-L1, anti-PD-L2; agents that block FOXP3 (e.g., to abrogate the activity/kill CD4+/CD25+ T regulatory cells); Flt3 ligand, imiquimod (Aldara), granulocyte-macrophage colony stimulating factor (GM-CSF); granulocyte-colony stimulating factor (G-CSF), sargramostim (Leukine®); hormones including without limitation prolactin and growth hormone; Toll-like receptor (TLR) agonists, including but not limited to TLR-2 agonists, TLR-4 agonists, TLR-7 agonists, and TLR-9 agonists; TLR antagonists, including but not limited to TLR-2 antagonists, TLR-4 antagonists, TLR-7 antagonists, and TLR-9 antagonists; anti-inflammatory agents and immunomodulators, including but not limited to, COX-2 inhibitors (e.g., Celecoxib, NSAIDS), glucocorticoids, statins, and thalidomide and analogues thereof including IMiD™s (which are structural and functional analogues of thalidomide (e.g., REVLIMID® (lenalidomide), ACTIMID® (pomalidomide)); proinflammatory agents, such as fungal or bacterial components or any proinflammatory cytokine or chemokine; immunotherapeutic vaccines including, but not limited to, virus-based vaccines, bacteria-based vaccines, or antibody-based vaccines; and any other immunomodulators, immunopotentiators, anti-inflammatory agents, pro-inflammatory agents, and any agents that modulate the number of, modulate the activation state of, and/or modulate the survival of antigen-presenting cells or of TH17, TH1, and/or Treg cells. Any combination of such agents is contemplated by the invention, and any of such agents combined with or administered in a protocol with (e.g., concurrently, sequentially, or in other formats with) a yeast-based immunotherapeutic is a composition encompassed by the invention. Such agents are well known in the art. These agents may be used alone or in combination with other agents described herein.

Agents can include agonists and antagonists of a given protein or peptide or domain thereof. As used herein, an "agonist" is any compound or agent, including without limitation small molecules, proteins, peptides, antibodies, nucleic acid binding agents, etc., that binds to a receptor or ligand and produces or triggers a response, which may include agents that mimic or enhance the action of a naturally occurring substance that binds to the receptor or ligand. An "antagonist" is any compound or agent, including without limitation small molecules, proteins, peptides, antibodies, nucleic acid binding agents, etc., that blocks or inhibits or reduces the action of an agonist.

Compositions of the invention can further include or can be administered with (concurrently, sequentially, or intermittently with) any other agents or compositions or protocols that are useful for preventing or treating cancer or any compounds that treat or ameliorate any symptom of cancer, and particularly cancers associated with MUC1 expression or overexpression. In addition, compositions of the invention can be used together with other immunotherapeutic compositions, including prophylactic and/or therapeutic immunotherapy. Additional agents, compositions or protocols (e.g., therapeutic protocols) that are useful for the treatment of cancer include, but are not limited to, chemotherapy, surgical resection of a tumor, radiation therapy, allogeneic or autologous stem cell transplantation, T cell adoptive transfer, other types of immunotherapy, including viral vector-based immunotherapy and dendritic cell/tumor fusion immunotherapy, and/or targeted cancer therapies (e.g., small molecule drugs, biologics, or monoclonal antibody therapies that specifically target molecules involved in tumor growth and progression, including, but not limited to, selective estrogen receptor modulators (SERMs), aromatase inhibitors, tyrosine kinase inhibitors, serine/threonine kinase inhibitors, histone deacetylase (HDAC) inhibitors, retinoid receptor activators, apoptosis stimulators, angiogenesis inhibitors, poly (ADP-ribose) polymerase (PARP) inhibitors, or immunostimulators). Any of these additional therapeutic agents and/or therapeutic protocols may be administered before, concurrently with, alternating with, or after the immunotherapy compositions of the invention, or at different time points. For example, when given to an individual in conjunction with chemotherapy or a targeted cancer therapy, it may be desirable to administer the yeast-MUC1 immunotherapy compositions during the "holiday" between doses of chemotherapy or targeted cancer therapy, in order to maximize the efficacy of the immunotherapy compositions. Surgical resection of a tumor may frequently precede administration of a yeast-MUC1 immunotherapy composition, but additional or primary surgery may occur during or after administration of a yeast-MUC1 immunotherapy composition.

The invention also includes a kit comprising any of the compositions described herein, or any of the individual components of the compositions described herein. Kits may include additional reagents and written instructions or directions for using any of the compositions of the invention to prevent or treat cancer associated with or characterized by MUC1 expression or overexpression.

Methods for Administration or Use of Compositions of the Invention

Yeast-MUC1 immunotherapeutic compositions of the invention are designed for use to prevent or treat cancers that are associated with or characterized by MUC1 expression or overexpression, including by preventing emergence of such cancers, arresting progression of such cancers or eliminating such cancers. More particularly, yeast-MUC1 immunotherapeutic compositions can be used to prevent, inhibit or delay the development of MUC1-expressing tumors, and/or to prevent, inhibit or delay tumor migration and/or tumor invasion of other tissues (metastases) and/or to generally prevent or inhibit progression of cancer in an individual. Yeast-MUC1 immunotherapeutic compositions can also be used to ameliorate at least one symptom of the cancer, such as by reducing tumor burden in the individual; inhibiting tumor growth in the individual; increasing survival of the individual; and/or preventing, inhibiting, reversing or delaying progression of the cancer in the individual.

Cancers that are relevant to the compositions and methods of the invention are any cancer that expresses, or may express, MUC1, or cancers in proximity to cancers that express or may express MUC1, including cancers of epithelial tissues, and include, but are not limited to, cancer of the breast, small intestine, stomach, kidney, bladder, uterus, ovary, testes, lung, colon, pancreas, prostate, testes, and metastatic cancers thereof. In addition, MUC1 is or may be expressed in hematological cancers, such as lymphomas, leukemias and myelomas, including, but not limited to, chronic lymphocytic leukemia (CLL), multiple myelogenous lymphoma (MML), acute myeloid leukemia (AML), Epstein-Barr virus (EBV) transformed B cells, Burkitt's and Hodgkin's lymphomas.

In one aspect, MUC1 is not detected in the individual's cancer at the time the composition is first administered. When MUC1 is not detected in the individual's cancer, the individual may have an earlier stage cancer in which MUC1 expression has not yet manifested (e.g., stage I or stage II), or in which MUC1 expression is not yet detectable in any event (i.e., MUC1 may or may not be expressed at a low level or in a small number of tumor cells, but is not yet readily detectable using standard detection methods). Alternatively, the individual may have precancerous lesions or tumors, or may be known to be predisposed to developing cancer (e.g., by knowledge of family history, genetic markers, etc.). In these aspects of the invention, the development of MUC1-expressing tumor cells is prevented, delayed or inhibited by use of the Yeast-MUC1 immunotherapeutic composition.

In another aspect, MUC1 expression is or can be detected in the individual's cancer at the time the composition is first administered. The individual may have stage I, stage II, stage III, or stage IV cancer in this aspect of the invention. In this aspect, use of the Yeast-MUC1 immunotherapeutic composition reduces, eliminates or slows or arrests the growth of tumors expressing MUC1, which can result in reduction in tumor burden in the individual, inhibition of MUC1-expressing tumor growth, and/or increased survival of the individual.

Another embodiment of the invention relates to a method to treat cancer, and particularly, a MUC1-expressing cancer. The method includes administering to an individual who has a MUC1-expressing cancer a Yeast-MUC1 immunotherapeutic composition described herein, which can include a composition comprising: (a) a yeast vehicle; and (b) a cancer antigen comprising at least one MUC1 antigen. In one aspect, the method reduces tumor burden in the patient. In one aspect, the method increases survival of the patient. In one aspect, the method inhibits tumor growth in the individual.

In one aspect, the individual is additionally treated with at least one other therapeutic compound or therapeutic protocol useful for the treatment of cancer. Such therapeutic agents and protocols have been discussed in detail elsewhere herein. For example, in any of the embodiments regarding methods of the invention described herein, in one aspect, when the individual has cancer (regardless of the status of detectable MUC1 expression in tumor cells) the individual is being treated or has been treated with another therapy for cancer. Such therapy can include any of the therapeutic protocols or use of any therapeutic compound or agent described previously herein, including, but not limited to, chemotherapy, radiation therapy, targeted cancer therapy, surgical resection of a tumor, stem cell transfer, cytokine therapy, adoptive T cell transfer, and/or administration of a second immunotherapeutic composition. In the case of administration of a second immunotherapeutic composition, such compositions may include, but are not limited to, additional yeast-based immunotherapy, recombinant virus-based immunotherapy (viral vectors, e.g., see PCT Publication No. WO/00/34494), cytokine therapy, immunostimulant therapy (including chemotherapy with immunostimulating properties), DNA vaccines, dendritic cell/tumor fusion immunotherapy (e.g., see PCT Publication No. WO/2009/062001), and other immunotherapy compositions.

In one aspect, the second immunotherapeutic composition includes a second cancer antigen that is not a MUC1 antigen. For example, a second immunotherapeutic composition useful in combination with a Yeast-MUC1 immunotherapeutic composition is a yeast-immunotherapeutic composition comprising another cancer antigen that is expressed by the same tumor type, or by other tumors the individual to be treated has or may develop. Such cancer antigens include, but are not limited to, any one or more of carcinoembryonic antigen (CEA), point mutated Ras oncoprotein, Brachyury, EGFR, BCR-Abl, MART-1, MAGE-1, MAGE-3, GAGE, GP-100, MUC-2, normal and point mutated p53 oncoproteins, PSMA, tyrosinase, TRP-1 (gp75), NY-ESO-1, TRP-2, TAG72, KSA, CA-125, PSA, HER-2/neu/c-erb/B2, hTERT, p'73, B-RAF, adenomatous polyposis coli (APC), Myc, von Hippel-Lindau protein (VHL), Rb-1, Rb-2, androgen receptor (AR), Smad4, MDR1, Flt-3, BRCA-1, BRCA-2, pax3-fkhr, ews-fli-1, HERV-H, HERV-K, TWIST, Mesothelin, NGEP, modifications of such antigens, splice variants of such antigens, and epitope agonists of such antigens, as well as combinations of such antigens, and/or immunogenic domains thereof, modifications thereof, variants thereof, and/or epitope agonists thereof.

As used herein, to "treat" a cancer, or any permutation thereof (e.g., "treated for cancer", etc.) generally refers to administering a composition of the invention once the cancer has occurred (e.g., once the cancer has been diagnosed or detected in an individual), with at least one therapeutic goal of the treatment (as compared to in the absence of this treatment) including: reduction in tumor burden; inhibition of tumor growth; increase in survival of the individual; delaying, inhibiting, arresting or preventing the onset or development of metastatic cancer (such as by delaying, inhibiting, arresting or preventing the onset of development of tumor migration and/or tumor invasion of tissues outside of primary cancer and/or other processes associated with metastatic progression of cancer); delaying or arresting primary cancer progression; improvement of immune responses against the tumor; improvement of long term memory immune responses against the tumor antigens; and/or improved general health of the individual. To "prevent" or "protect" from a cancer, or any permutation thereof (e.g., "prevention of cancer", etc.), generally refers to administering a composition of the invention before a cancer has occurred, when pre-cancerous cells are detected, or before a specific stage of cancer or tumor antigen expression in a cancer has occurred (e.g., before MUC1 expression is detected in the cancer), with at least one goal of the treatment (as compared to in the absence of this treatment) including: preventing or delaying the onset or development of a cancer, or, should the cancer occur after the treatment, at least reducing the severity of the cancer (e.g., reducing the level of tumor growth, arresting cancer progression, improving the immune response against the cancer, inhibiting metastatic processes, etc.) or improving outcomes in the individual (e.g., improving survival).

The present invention includes the delivery (administration, immunization, vaccination) of a Yeast-MUC1 immunotherapeutic composition of the invention to a subject or individual. The administration process can be performed ex vivo or in vivo, but is typically performed in vivo. Ex vivo administration refers to performing part of the regulatory step outside of the patient, such as administering a composition of the present invention to a population of cells (dendritic cells) removed from a patient under conditions such that a yeast vehicle, antigen(s) and any other agents or compositions are loaded into the cell, and returning the cells to the patient. The therapeutic composition of the present invention can then be returned to a patient, or administered to a patient, by any suitable mode of administration.

Administration of a composition can be systemic, mucosal and/or proximal to the location of the target site (e.g., near a site of a tumor). Suitable routes of administration will be apparent to those of skill in the art, depending on the type of cancer to be prevented or treated and/or the target cell population or tissue. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992). In one aspect, a Yeast-MUC1 immunotherapeutic composition of the invention is administered subcutaneously. In one aspect, the Yeast-MUC1 immunotherapeutic composition is administered directly into a tumor milieu.

In general, a suitable single dose of a Yeast-MUC1 immunotherapeutic composition is a dose that is capable of effectively providing a yeast vehicle and the MUC1 antigen to a given cell type, tissue, or region of the patient body in an amount effective to elicit an antigen-specific immune response against one or more MUC1 antigens or epitopes, when administered one or more times over a suitable time period. For example, in one embodiment, a single dose of a Yeast-MUC1 of the present invention is from about $1\times10^5$ to about $5\times10^7$ yeast cell equivalents per kilogram body weight of the organism being administered the composition. One Yeast Unit (Y.U.) is $1\times10^6$ yeast cells or yeast cell equivalents. In one aspect, a single dose of a yeast vehicle of the present invention is from about 0.1 Y.U. ($1\times10^6$ yeast cells or yeast cell equivalents) to about 100 Y.U. ($1\times10^9$ cells) per dose (i.e., per organism), including any interim dose, in increments of $0.1\times10^6$ cells (i.e., $1.1\times10^6$, $1.2\times10^6$, $1.3\times10^6$ . . . ). In one embodiment, a suitable dose includes doses between 1 Y.U. and 40 Y.U. and in one aspect, between 10 Y.U. and 40 Y.U. or between 10 Y.U. and 80 Y.U. In one embodiment, the doses are administered at different sites on the individual but during the same dosing period. For example, a 40 Y.U. dose may be administered by injecting 10 Y.U. doses to four different sites on the individual during one dosing period. The invention includes administration of an amount of the Yeast-MUC1 immunotherapy composition (e.g., 1, 2, 3, 4, 5, 6, 7, 8, 9 10, 11, 12, 13, 14, 15, 16, 17, 18, 19, 20 Y.U. or more) at 1, 2, 3, 4, 5, 6, 7, 8, 9, 10, or more different sites on an individual to form a single dose.

"Boosters" or "boosts" of a therapeutic composition are administered, for example, when the immune response against the antigen has waned or as needed to provide an immune response or induce a memory response against a particular antigen or antigen(s). Boosters can be administered about 1, 2, 3, 4, 5, 6, 7, or 8 weeks apart, or monthly, bimonthly, quarterly, annually, and/or in a few or several year increments after the original administration, depending on the status of the individual being treated and the goal of the therapy at the time of administration (e.g., prophylactic, active treatment, maintenance). In one embodiment, an administration schedule is one in which doses of Yeast-MUC1 immunotherapeutic composition is administered at least 1, 2, 3, 4, 5, 6, 7, 8, 9, 10, or more times over a time period of from weeks, to months, to years. In one embodiment, the doses are administered weekly or biweekly for 1, 2, 3, 4, 5, 6, 7, 8, 9, 10 or more doses, followed by biweekly or monthly doses as needed to achieve the desired preventative or therapeutic treatment for cancer. Additional boosters can then be given at similar or longer intervals (months or years) as a maintenance or remission therapy, if desired.

In one aspect of the invention, one or more additional therapeutic agents or therapeutic protocols are administered or performed sequentially and/or concurrently with the administration of the Yeast-MUC1 immunotherapy composition, e.g., surgical resection of the tumor, administration of chemotherapy, administration of radiation therapy, administration of another immunotherapy composition or protocol including viral vector therapy and dendritic cell/tumor fusion therapy, cytokine therapy, adoptive T cell transfer (including adoptive transfer of T cells that have been stimulated ex vivo by an antigen and/or immunotherapy composition), or stem cell transplantation. In one example, yeast-MUC1 immunotherapy is administered in conjunction with a therapy utilizing viral vector-based immunotherapy, such as that described in PCT Publication No. WO/00/34494. In another example, yeast-MUC1 immunotherapy is administered in conjunction with dendritic cell/tumor cell fusion therapy or immune system cells (e.g., T cells) stimulated with such dendritic cell/tumor cell fusions, such as that described in PCT Publication No. WO/2009062001. In such embodiments, the non-yeast-based immunotherapy may target the MUC1 or a different tumor antigen, and such therapies may include the additional administration of other agents, such as cytokines, antibodies, or other agents.

In one aspect, one or more therapies for cancer (including any therapies described herein or otherwise known in the art) can be administered or performed prior to the first dose of Yeast-MUC1 immunotherapy composition or after the first dose is administered. In one embodiment, one or more therapies can be administered or performed in an alternating manner with the dosing of Yeast-MUC1 immunotherapy composition, such as in a protocol in which the Yeast-MUC1 composition is administered at prescribed intervals in between one or more consecutive doses of chemotherapy or other therapy. In one embodiment, the Yeast-MUC1 immunotherapy composition is administered in one or more doses over a period of time prior to commencing additional therapies. In other words, the Yeast-MUC1 immunotherapeutic composition is administered as a monotherapy for a period of time, and then an additional therapy is added (e.g., chemotherapy), either concurrently with new doses of Yeast-MUC1 immunotherapy, or in an alternating fashion with Yeast-MUC1 immunotherapy. Alternatively or in addition, another therapy may be administered for a period of time prior to beginning administration of the Yeast-MUC1 immunotherapy composition, and the concepts may be combined (e.g., surgical resection of a tumor, followed by monotherapy with Yeast-MUC1 immunotherapy for several weeks, followed by alternating doses of chemotherapy and Yeast-MUC1 immunotherapy for weeks or months, optionally followed by monotherapy using Yeast-MUC1 immunotherapy and/or another therapy, or by a new protocol of combinations of therapy provided sequentially, concurrently, or in alternating fashion). Various protocols for the treatment of cancer using Yeast-MUC1 immunotherapy are contemplated by the invention, and these examples should be considered to be non-limiting examples of various possible protocols.

A virus-based immunotherapy composition typically comprises a viral vector comprising a virus genome or portions thereof (e.g., a recombinant virus) and a nucleic acid sequence encoding at least one antigen(s) from a disease causing agent or disease state (e.g., a cancer antigen(s), infectious disease antigen(s), and/or at least one immunogenic domain thereof). In some embodiments, a virus-based immunotherapy composition further includes at least one viral vector comprising one or more nucleic acid sequences encoding one or more immunostimulatory molecule(s). In some embodiments, the genes encoding immunostimulatory molecules and antigens are inserted into the same viral vector (the same recombinant virus).

Dendritic cell/tumor cell fusion immunotherapy compositions typically are hybrid cells generated by the fusion between dendritic cells and non-dendritic cells that express tumor antigens, including tumor cells, using fusion methods that are known in the art. The fused cells have dendritic cell characteristics and also express and present tumor antigens from the tumor cell. The compositions may be administered to an individual, or used to stimulate T cells ex vivo for T cell transfer methods.

In one aspect of the invention, additional antigens other than MUC1 are also targeted using yeast-based immunotherapy, in addition to targeting MUC1. Such additional target antigens can be included within the same yeast-vehicle as the MUC1 antigens, or additional yeast-based immunotherapy compositions targeting different antigens can be produced and then combined as desired depending on the individual to be treated, the antigens expressed by the type of cancer or by the individual's particular tumor, and/or depending on the stage of cancer in the individual, or the stage of treatment of the individual. For examples a combination of antigens may be selected that cover: (1) antigens involved in seminal events in cancer development, such as mutated Ras, (2) antigens involved in or associated with dysregulation of cellular processes, such as CEA or MUC1, and (3) Brachyury, which is involved in metastatic processes. For example, one or more other yeast-based immunotherapy compositions may express one or more antigens including, but not limited to, carcinoembryonic antigen (CEA), point mutated Ras oncoprotein, Brachyury, EGFR, BCR-Abl, MART-1, MAGE-1, MAGE-3, GAGE, GP-100, MUC-2, normal and point mutated p53 oncoproteins, PSMA, tyrosinase, TRP-1 (gp75), NY-ESO-1, TRP-2, TAG72, KSA, CA-125, PSA, HER-2/neu/c-erb/B2, hTERT, p'73, B-RAF, adenomatous polyposis coli (APC), Myc, von Hippel-Lindau protein (VHL), Rb-1, Rb-2, androgen receptor (AR), Smad4, MDR1, Flt-3, BRCA-1, BRCA-2, pax3-fkhr, ews-fli-1, HERV-H, HERV-K, TWIST, Mesothelin, NGEP, modifications of such antigens, splice variants of such antigens, and epitope agonists of such antigens, as well as combinations of such antigens, and/or immunogenic domains thereof, modifications thereof, variants thereof, and/or epitope agonists thereof. One, two, three, or more of these yeast-based immunotherapy compositions may be administered to an individual prior to, concurrently or alternating with, and/or after administration of a Yeast-MUC1 immunotherapy composition, in order to optimize targeting of antigens in the individual's tumor. As above, additional therapies can also be used in such protocols (e.g., surgical resection of tumor, chemotherapy, targeted cancer therapy, radiation therapy, etc.).

In one embodiment of the invention, a method to treat cancer is provided. The method includes the steps of: (a) administering to an individual who has cancer or pre-cancerous tumor, a first immunotherapeutic composition comprising a yeast vehicle and a MUC1 antigen as described herein; and (b) administering to the individual, prior to, concurrently with, or subsequent to, administration of the first immunotherapeutic composition one or more additional immunotherapeutic compositions, each comprising a yeast vehicle and each comprising a different cancer antigen that is not a MUC1 antigen. The additional cancer antigen can be any of those known in the art or described herein, including, but not limited to, mutated Ras, carcinoembryonic antigen (CEA), Brachyury, EGFR, etc. Steps may be repeated as needed to treat a particular individual's cancer, and the cancer antigens can be modified before or during treatment to specifically address the particular individual's cancer.

In the method of the present invention, compositions and therapeutic compositions can be administered to any animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Mammals to treat or protect utilizing the invention include humans, non-human primates, dogs, cats, mice, rats, goats, sheep, cattle, horses and pigs.

An "individual" is a vertebrate, such as a mammal, including without limitation a human. Mammals include, but are not limited to, farm animals, sport animals, pets, primates, mice and rats. The term "individual" can be used interchangeably with the term "animal", "subject" or "patient".

General Techniques Useful in the Invention

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., *Academic Press* (1980); *Methods in yeast genetics: a laboratory course manual*, Rose et al., Cold Spring Harbor Laboratory Press (1990); The Yeast *Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988), *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000); Casarett and Doull's *Toxicology The Basic Science of Poisons*, C. Klaassen, ed., 6th edition (2001), and Vaccines, S. Plotkin, W. Orenstein, and P. Offit, eds., Fifth Edition (2008).

General Definitions

A "TARMOGEN®" (GlobeImmune, Inc., Louisville, Colo.) generally refers to a yeast vehicle expressing one or more heterologous antigens extracellularly (on its surface), intracellularly (internally or cytosolically) or both extracellularly and intracellularly. TARMOGEN®s have been generally described (see, e.g., U.S. Pat. No. 5,830,463). Certain yeast-based immunotherapy compositions, and methods of making and generally using the same, are also described in detail, for example, in U.S. Pat. Nos. 5,830,463, 7,083,787, 7,736,642, Stubbs et al., *Nat. Med.* 7:625-629 (2001), Lu et al., *Cancer Research* 64:5084-5088 (2004), and in Bernstein et al., *Vaccine* 2008 Jan. 24; 26(4):509-21, each of which is incorporated herein by reference in its entirety.

As used herein, the term "analog" refers to a chemical compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but has a different structure or origin with respect to the reference compound.

The terms "substituted", "substituted derivative" and "derivative", when used to describe a compound, means that at least one hydrogen bound to the unsubstituted compound is replaced with a different atom or a chemical moiety.

Although a derivative has a similar physical structure to the parent compound, the derivative may have different chemical and/or biological properties than the parent compound. Such properties can include, but are not limited to, increased or decreased activity of the parent compound, new activity as compared to the parent compound, enhanced or decreased bioavailability, enhanced or decreased efficacy, enhanced or decreased stability in vitro and/or in vivo, and/or enhanced or decreased absorption properties.

In general, the term "biologically active" indicates that a compound (including a protein or peptide) has at least one detectable activity that has an effect on the metabolic, physiological, chemical, or other processes of a cell, a tissue, or an organism, as measured or observed in vivo (i.e., in a natural physiological environment) or in vitro (i.e., under laboratory conditions).

According to the present invention, the term "modulate" can be used interchangeably with "regulate" and refers generally to upregulation or downregulation of a particular activity. As used herein, the term "upregulate" can be used generally to describe any of: elicitation, initiation, increasing, augmenting, boosting, improving, enhancing, amplifying, promoting, or providing, with respect to a particular activity. Similarly, the term "downregulate" can be used generally to describe any of: decreasing, reducing, inhibiting, ameliorating, diminishing, lessening, blocking, or preventing, with respect to a particular activity.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA, immunoblot assays, etc.).

General reference to a protein or polypeptide used in the present invention includes full-length proteins, or any fragment, domain (structural, functional, or immunogenic), conformational epitope, or a homologue or variant of a given protein. A fusion protein may also be generally referred to as a protein or polypeptide. An isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" or "variant" is used to refer to a protein or peptide which differs from a reference protein or peptide (i.e., the "prototype" or "wild-type" protein) by minor modifications to the reference protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue or variant can have enhanced, decreased, or substantially similar properties as compared to the reference protein or peptide. A homologue or variant can include an agonist of a protein or an antagonist of a protein. Homologues or variants can be produced using techniques known in the art for the production of proteins including, but not limited to, direct modifications to the isolated reference protein, direct protein synthesis, or modifications to the nucleic acid sequence encoding the protein using, for example, classic or recombinant DNA techniques to effect random or targeted mutagenesis, resulting in the encoding of a protein variant. In addition, naturally occurring variants of a reference protein may exist (e.g., isoforms, allelic variants, or other natural variants that may occur from individual to individual) and may be isolated, produced and/or utilized in the invention.

A homologue or variant of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 86% identical, or at least about 87% identical, or at least about 88% identical, or at least about 89% identical, or at least about 90%, or at least about 91% identical, or at least about 92% identical, or at least about 93% identical, or at least about 94% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein (e.g., an amino acid sequence specified herein, or the amino acid sequence of a specified protein). In one embodiment, the homologue or variant comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the amino acid sequence of the reference protein.

As used herein, unless otherwise specified, reference to a percent (%) identity refers to an evaluation of homology which is performed using: (1) a Basic Local Alignment Search Tool (BLAST) basic homology search using blastp for amino acid searches and blastn for nucleic acid searches with standard default parameters, wherein the query sequence is filtered for low complexity regions by default (such as described in Altschul, S. F., Madden, T. L., Schääffer, A. A., Zhang, J Zhang, Z., Miller, W. & Lipman, D. J. (1997) "Gapped BLAST and PSI-BLAST: a new generation of protein database search programs." *Nucleic Acids Res.* 25:3389-3402, incorporated herein by reference in its entirety); (2) a BLAST alignment of two sequences (e.g., using the parameters described below); (3) and/or PSI-BLAST with the standard default parameters (Position-Specific Iterated BLAST. It is noted that due to some differences in the standard parameters between Basic BLAST and BLAST for two sequences, two specific sequences might be recognized as having significant homology using the BLAST program, whereas a search performed in Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST as described in Tatusova and Madden, (1999), "Blast 2 sequences—a new tool for comparing protein and nucleotide sequences", *FEMS Microbiol Lett.* 174:247-250, incorporated herein by reference in its entirety. Such a sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST sequence alignment for two sequences is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome or a segment of the genome containing more than one gene, in which the nucleic acid molecule is found in nature. An isolated nucleic acid molecule can include a complete gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule may also include portions of a gene. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a plasmid useful for transfecting yeast. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors. Preferred recombinant vectors are capable of being expressed in a transfected host cell, such as a yeast.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

Example 1

The following example describes the production of a Yeast-MUC1 immunotherapeutic composition known as GI-6101.

In this experiment, yeast (*Saccharomyces cerevisiae*) were engineered to express a human MUC1 antigen under the control of the copper-inducible promoter, CUP1, or the constitutive promoter, TEF2, producing yeast-MUC1 immunotherapy compositions. In each case, a fusion protein comprising a MUC1 antigen was produced as a single polypeptide with the following sequence elements fused in frame from N- to C-terminus, represented by SEQ ID NO:15: (1) a MUC1 SEA/ED segment (positions 1-59 of SEQ ID NO:15); (2) a VNTR segment comprising two VNTR domains (positions 60-100 of SEQ ID NO:15); (3) a MUC1 TM domain (positions 101-128 of SEQ ID NO:15); and (4) a MUC1 CD (positions 129-200 of SEQ ID NO:15). This fusion protein further included a MUC1 signal sequence (positions 1-30 of SEQ ID NO:14) that could be substituted with a different N-terminal sequence designed to impart resistance to proteasomal degradation and/or stabilize expression, such as the peptide represented by SEQ ID NO:21, or an N-terminal peptide from a yeast alpha leader sequence such as SEQ ID NO:19 or SEQ ID NO:20. The complete fusion protein including the N-terminal MUC1 signal sequence and a hexahistidine C-terminal tag to facilitate identification and/or purification of the protein is a single polypeptide with the following sequence elements fused in frame from N- to C-terminus, represented by SEQ ID NO:14: (1) MUC1 signal sequence (positions 1-30 of SEQ ID NO:14); (2) a MUC1 SEA/ED segment (positions 31-89 of SEQ ID NO:14); (3) a VNTR segment comprising two VNTR domains (positions 90-130 of SEQ ID NO:14); (4) a MUC1 TM domain (positions 131-158 of SEQ ID NO:14); (5) a MUC1 CD (positions 159-230 of SEQ ID NO:14); and (6) a hexapeptide histidine tag (positions 231-236 of SEQ ID NO:14). SEQ ID NO:14 is encoded by the nucleotide sequence represented by SEQ ID NO:13 (codon optimized for yeast expression).

Briefly, DNA encoding the MUC1 antigens were synthesized, and then inserted at EcoRI and NotI cloning sites behind the CUP1 promoter (vector pGI-100) or the TEF2 promoter (vector plu011) in yeast 2 μm expression vectors. Nucleotide sequences encoding a C-terminal hexahistidine peptide were added to the plasmid vector to encode the complete fusion protein represented by SEQ ID NO:14. The resulting plasmids were transformed into DH5a for plasmid storage, and into *Saccharomyces cerevisiae* W303a for production of the yeast-MUC1 immunotherapeutic compositions.

Transformation into *Saccharomyces cerevisiae* was performed by lithium acetate/polyethylene glycol transfection, and primary transfectants were selected on solid minimal plates lacking Uracil (UDM; uridine dropout medium). Colonies were selected by growing in U2 (uridine dropout medium) or UL2 (uridine and leucine dropout medium) medium at 30° C.

The yeast-MUC1 immunotherapy composition comprising a polynucleotide encoding the human MUC1 fusion protein represented by SEQ ID NO:14 under the control of the TEF2 promoter is also referred to herein as GI-6101.

Liquid cultures lacking uridine (U2) or lacking uridine and leucine (UL2) were inoculated using the plates and starter cultures described above, and were grown for about 24 h at 30° C., 250 rpm. pH buffered UL2 medium containing 4.2 g/L of Bis-Tris (BT-UL2) was also inoculated from frozen yeast banks to evaluate yeast-MUC1 immunotherapeutics produced under neutral pH manufacturing conditions (data not shown). Culturing in pH buffered UL2 medium exposes β-glucans on the yeast cell wall and is believed to modify the cellular immune responses induced by the yeast as a result of modifying the interactions with dectin receptors on antigen presenting cells. The remaining culture conditions were the same whether U2, UL2 or BT-UL2 was used. Primary cultures were used to inoculate final cultures of the same formulation.

Recipe for U2 Liquid Media:
15 g/L of glucose
6.7 g/L of Yeast nitrogen base containing ammonium sulfate
0.04 g/L each of histidine, tryptophan, adenine and 0.06 g/L of leucine Recipe for UL2 Liquid Media:
15 g/L of glucose
6.7 g/L of Yeast nitrogen base containing ammonium sulfate
0.04 g/L each of histidine, tryptophan, and adenine In initial experiments comparing yeast-MUC1 immunotherapeutic compositions under the control of different promoters, CUP1-driven (inducible expression) yeast-MUC1 expression was produced in a 2-step or 3-step culture; after starter or intermediate culture reaches mid-log (1.5-4 Y.U./ml), the expression was initiated by the addition of 0.375 mM copper sulfate to final the culture diluted to 0.1 or 0.2 Y.U./mL from intermediate culture and was continued until the culture reached a density of 1.5-3 Y.U. TEF2-driven yeast-MUC1 expression is constitutive, and growth of these cells was continued until the cultures reached a density of between 1.1 to 4.0 Y.U./ml. The cells from each culture were then harvested, washed and heat-killed at 56° C. for 1 hour in PBS.

After heat-kill of the cultures, the cells were washed three times in PBS. Total protein expression was measured by a TCA precipitation/nitrocellulose binding assay and by Western blot using an anti-his tag monoclonal antibody and an anti-MUC1 (VNTR) antibody (sc-7313, Santa Cruz). Protein content was quantified using semi-quantitative digital imaging methods. GI-6101 was expected to express the MUC1 fusion protein as a membrane associated protein of about 25 kDa.

Figure 2C:
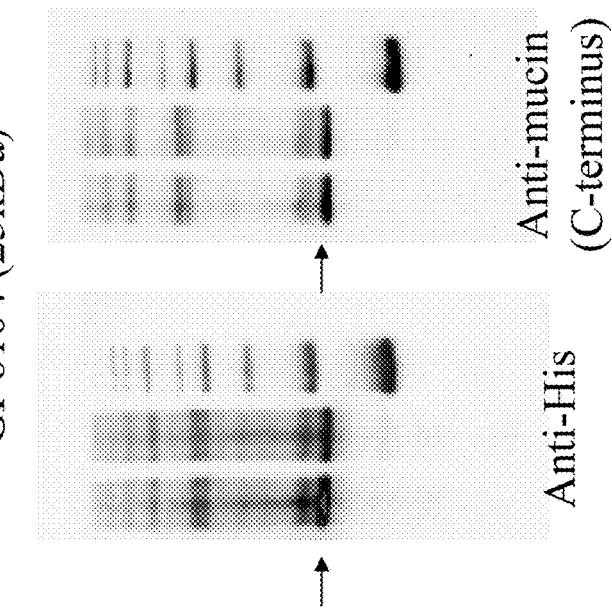
FIG. 2C is a digitized image showing expression of MUC1 fusion protein by GI-6104.
Figure 2B:
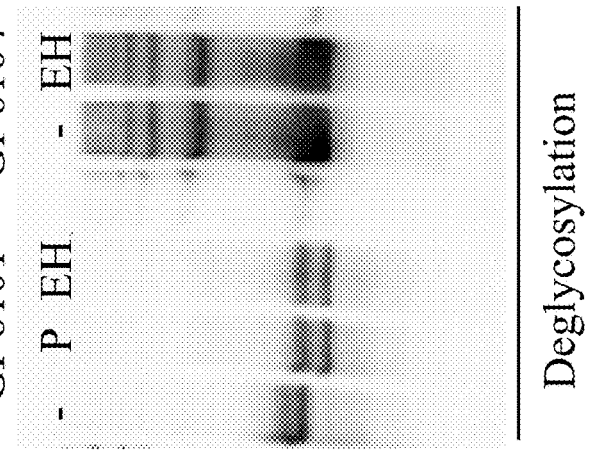
FIG. 2B is a digitized image showing expression of MUC1 fusion proteins from GI-6101 and 6104 before and after deglycosylation.
Figure 2A:
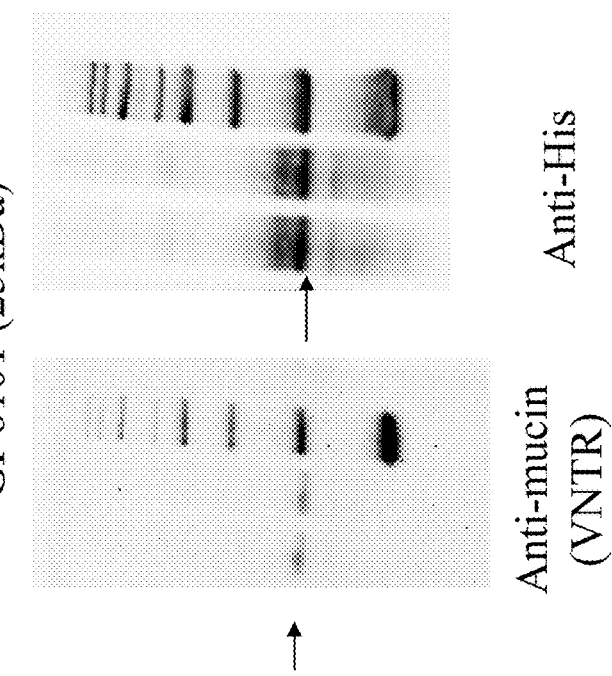
FIG. 2A is a digitized image showing expression of MUC1 fusion protein by GI-6101.

FIG. 2A shows expression of the MUC1 antigen in GI-6101 using anti-MUC1 (VNTR) and anti-His antibodies for detection. These results showed good expression of the MUC1 protein. FIG. 2B shows the MUC1 antigen of GI-6101 after deglycosylation with either EdoH or PNGaseF. This figure shows that the GI-6101 fusion protein is expressed as a glycosylated product, since the size of the fusion protein is larger than estimated prior to deglycosylation, but reduces to the expected size (25 kDa) after deglycosylation by EdoH or PNGaseF.

Quantification of antigen expression in GI-6101 that was grown under standard culture conditions was compared to GI-6101 grown under neutral pH conditions, as described above. The levels of antigen expression were approximately the same using either process (data not shown), demonstrating that the neutral pH process does not alter the level of MUC1 antigen expression by the yeast.

Example 2

The following example described the production of a yeast-MUC1 immunotherapeutic composition known as GI-6104.

In this experiment, yeast (*Saccharomyces cerevisiae*) were engineered to express a human MUC1 antigen under the control of the copper-inducible promoter, CUP1, or the constitutive promoter, TEF2, producing yeast-MUC1 immunotherapy compositions. In each case, a fusion protein comprising a MUC1 antigen was produced as a single polypeptide with the following sequence elements fused in frame from N- to C-terminus, represented by SEQ ID NO:18: SEQ ID NO:18 includes the following MUC1 antigens, in the following order from N- to C-terminus: (1) a first MUC1 CD (positions 1-72 of SEQ ID NO:18); (2) a second MUC1 CD (positions 73-144 of SEQ ID NO:18); and (3) a third MUC1 CD (positions 145-216 of SEQ ID NO:18). This fusion protein further included an N-terminal sequence designed to impart resistance to proteasomal degradation and/or stabilize expression (represented in this fusion protein by SEQ ID NO:21). The fusion protein could alternatively be designed using a MUC1 signal sequence (e.g., positions 1-30 of SEQ ID NO:14), a different synthetic N-terminal peptide as described herein, or an N-terminal peptide from a yeast alpha leader sequence such as SEQ ID NO:19 or SEQ ID NO:20. The complete fusion protein including the N-terminal peptide and a hexahistidine C-terminal tag to facilitate identification and/or purification of the protein is a single polypeptide with the following sequence elements fused in frame from N- to C-terminus (represented by SEQ ID NO:17): (1) a synthetic peptide represented by SEQ ID NO:21 (positions 1-6 of SEQ ID NO:17); (2) a first MUC1 CD (positions 7-78 of SEQ ID NO:17); (3) a second MUC1 CD (positions 79-150 of SEQ ID NO:17); (4) a third MUC1 CD (positions 151-222 of SEQ ID NO:17); and (5) a hexahistidine tag (positions 223-228 of SEQ ID NO:17). SEQ ID NO:17 is encoded by the nucleotide sequence represented by SEQ ID NO:16 (codon optimized for yeast expression).

Briefly, DNA encoding the MUC1 antigens were synthesized, and then inserted at EcoRI and NotI cloning sites behind the CUP1 promoter (vector pGI-100) or the TEF2 promoter (vectors plu011) in yeast 2 µm expression vectors. Nucleotide sequences encoding a C-terminal hexahistidine peptide was added to the plasmid vector to encode the complete fusion protein represented by SEQ ID NO:17. The resulting plasmids were transformed into DH5a for plasmid storage, and into *Saccharomyces cerevisiae* W303a for production of the yeast-MUC1 immunotherapeutic compositions.

Transformation into *Saccharomyces cerevisiae* was performed by lithium acetate/polyethylene glycol transfection, and primary transfectants were selected on solid minimal plates lacking Uracil (UDM; uridine dropout medium). Colonies were selected by growing in U2 (uridine dropout medium) or UL2 (uridine and leucine dropout medium) medium at 30° C.

The yeast-MUC1 immunotherapy composition comprising a polynucleotide encoding the human MUC1 fusion protein represented by SEQ ID NO:17 under the control of the CUP1 promoter is also referred to herein as GI-6104.

Liquid cultures lacking uridine (U2) or lacking uridine and leucine (UL2) (media recipes are provided in Example 1) were inoculated using the plates and starter cultures described above, and were grown for about 24 h at 30° C., 250 rpm. pH buffered UL2 medium containing 4.2 g/L of Bis-Tris (BT-UL2) was also inoculated from frozen yeast banks to evaluate yeast-MUC1 immunotherapeutics produced under neutral pH manufacturing conditions (data not shown). Culturing in pH buffered UL2 medium exposes β-glucans on the yeast cell wall and is believed to modify the cellular immune responses induced by the yeast as a result of modifying the interactions with dectin receptors on antigen presenting cells. The remaining culture conditions were the same whether UL2 or BT-UL2 was used. Primary cultures were used to inoculate final cultures of the same formulation.

In initial experiments comparing yeast-MUC1 immunotherapeutic compositions under the control of different promoters, CUP1-driven (inducible expression) yeast-MUC1 expression was produced in a 2-step or 3-step culture; after starter or intermediate culture reaches mid-log (1.5-4 YU/ml), antigen expression was initiated by the addition of 0.375 mM copper sulfate to final the culture diluted to 0.1 or 0.2 YU/mL from intermediate culture, and was continued until the culture reached a density of 1.5-3 Y.U. CUP1-driven (inducible expression) yeast-MUC1 expression was also initiated by the addition of 0.375 mM copper sulfate after the final yeast-MUC1 culture reached a density of approximately 2 Y.U./ml, and was induced for 4-6 hours. TEF2-driven yeast-MUC1 expression is constitutive, and growth of these cells was continued until the cultures reached a density of between 1.1 to 4.0 Y.U./ml. The cells from each culture were then harvested, washed and heat-killed at 56° C. for 1 hour in PBS.

After heat-kill of the cultures, the cells were washed three times in PBS. Total protein expression was measured by a TCA precipitation/nitrocellulose binding assay and by Western blot using an anti-his tag monoclonal antibody and an anti-MUC1 (C-terminus) antibody (sc-6827, Santa Cruz). Protein content was quantified using semi-quantitative digital imaging methods. GI-6104 was expected to express the MUC1 fusion protein as a cytosolic protein of about 25 kDa.

FIG. 2C shows expression of the MUC1 antigen in GI-6104 using anti-MUC1 (C-terminus) and anti-His antibodies for detection. These results showed good expression of the MUC1 fusion protein. FIG. 2B shows the MUC1 antigen of GI-6104 after deglycosylation with EdoH. This figure shows that the GI-6104 fusion protein is not expressed as a glycosylated product, since the size of the fusion protein is the same prior to and after deglycosylation with EdoH.

Quantification of antigen expression in GI-6104 that was grown under standard culture conditions was compared to GI-6104 grown under neutral pH conditions, as described above. The levels of antigen expression were approximately the same using either process (data not shown), demonstrating that the neutral pH process does not alter the level of MUC1 antigen expression by the yeast.

Example 3

The following example describes the production of a Yeast-MUC1 agonist immunotherapeutic composition known as GI-6105.

In this experiment, yeast (*Saccharomyces cerevisiae*) were engineered to express a human MUC1 agonist antigen under the control of the copper-inducible promoter, CUP1, producing a yeast-MUC1 agonist immunotherapy composition. The MUC1 agonist antigen was designed using the antigen from the yeast-MUC1 immunotherapy composition of GI-6101 (see Example 1) as a template. Briefly, a fusion protein comprising a MUC1 agonist antigen was produced as a single polypeptide with the following sequence elements fused in frame from N- to C-terminus, represented by SEQ ID NO:23: (1) MUC1 signal sequence (positions 1-30 of SEQ ID NO:23); (2) a MUC1 SEA/ED segment (positions 31-89 of SEQ ID NO:23); (3) a VNTR segment comprising two VNTR domains (positions 90-130 of SEQ ID NO:23); (4) a MUC1 TM domain (positions 131-158 of SEQ ID NO:23); (5) a MUC1 CD (positions 159-230 of SEQ ID NO:23); (6) a MUC1 agonist epitope (positions 231-246 of SEQ ID NO:23) and (7) a hexapeptide histidine tag (positions 247-252 of SEQ ID NO:23). SEQ ID NO:23 is encoded by the nucleotide sequence represented by SEQ ID NO:22 (codon optimized for yeast expression). The MUC1 signal sequence (positions 1-30 of SEQ ID NO:23) could be substituted with a different N-terminal sequence designed to impart resistance to proteasomal degradation and/or stabilize expression, such as the peptide represented by SEQ ID NO:21, or an N-terminal peptide from a yeast alpha leader sequence such as SEQ ID NO:19 or SEQ ID NO:20. hexahistidine C-terminal tag is optional, and facilitates identification and/or purification of the protein. As compared to the antigen in GI-6101 (e.g., SEQ ID NO:14 or 15), the sequence in GI-6105 contains the following amino acid substitutions to create a variety of agonist epitopes (substitution positions given with reference to SEQ ID NO:23, with further reference to the location of the substitution in a wild-type MUC1 represented by Accession No. NP_001191214): A96Y (position 161 in wild-type MUC1), P97L (position 162 in wild-type MUC1), G104V (position 169 in wild-type MUC1), S105Y (position 170 in wild-type MUC1), T106L (position 171 in wild-type MUC1), A147Y (position 392 in wild-type MUC1), C161V (position 406 in wild-type MUC1), T199L (position 444 in wild-type MUC1), D200F (position 445 in wild-type MUC1), S215Y (position 460 in wild-type MUC1), and T239L (position 93 in wild-type MUC1).

A plasmid containing the MUC1 agonist antigen for GI-6105 (SEQ ID NO:23) was transfected into W303a yeast and transformants were selected after 3 days of growth at 30° C. on uridine dropout agar (UDA). Single colonies were re-streaked onto uridine and leucine dropout agar (ULDA) plates and incubated at 30° C. for an additional 4 days to select for cells with elevated plasmid copy number.

A single colony of GI-6105 was removed from the ULDA plate and used to inoculate 25 mL of UL2 liquid medium (starter culture). The starter culture was incubated with shaking at 30° C. to a density of 3.7 YU/mL, and then used to inoculate an intermediate culture to 0.3 YU/mL. The intermediate culture and grown to a density of 3.0 YU/mL, and then used to inoculate a final culture to a density of 0.04 YU/mL. The final culture was grown to a density of 3.6 YU/mL, then treated with 0.5 mM copper sulfate for 3 h at 30° C. to induce Muc1 agonist v1.0 antigen expression.

Figure 3:
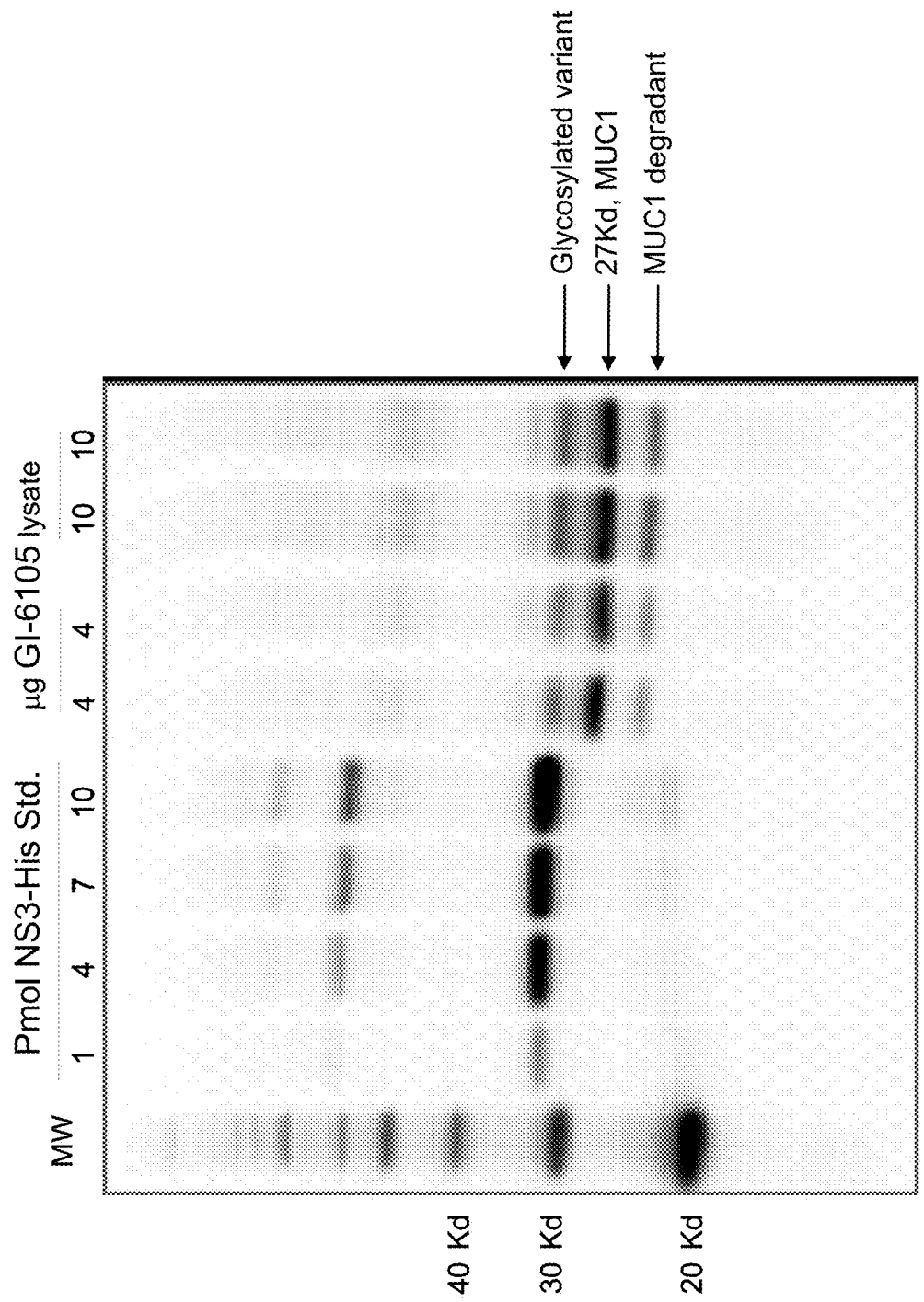
FIG. 3 is a digitized image showing expression of MUC1 fusion protein by GI-6105.

The induced cells were washed once with PBS, heat killed at 56° C. for 1 h, then thrice washed in PBS. Total protein content of the heat killed cells was measured by Amidoschwarz assay and antigen content was measured by western blot, with a monoclonal antibody recognizing the C-terminal hexahistidine epitope tag. Antigen quantity was determined by interpolation against a standard curve comprised of his tagged HCV NS3 protein. As shown in FIG. 3, the antigen was expressed by the yeast, and the antigen content for GI-6105 was estimated to be approximately 2801 Ng/YU.

Example 4

The following example describes the production of a Yeast-MUC1 agonist immunotherapeutic composition known as GI-6106.

In this experiment, yeast (*Saccharomyces cerevisiae*) were engineered to express a human MUC1 agonist antigen under the control of the copper-inducible promoter, CUP1, producing a yeast-MUC1 agonist immunotherapy composition. The MUC1 agonist antigen was designed using a full-length wild-type MUC1 antigen having Accession No. NP_001191214, although other wild-type MUC1 proteins could be utilized to design similar agonists. Briefly, a fusion protein comprising a MUC1 agonist antigen was produced as a single polypeptide with the following sequence elements fused in frame from N- to C-terminus, represented by SEQ ID NO:25: (1) an alpha factor leader sequence disclosed elsewhere herein by SEQ ID NO:19 (positions 1-89 of SEQ ID NO:25); (2) a linker sequence of Thr-Ser (positions 90-91 of SEQ ID NO:25); (3) a full-length MUC1 agonist protein corresponding to a wild-type protein except for the introduction of 11 agonist epitopes (positions 92-566 of SEQ ID NO:25) and (7) a hexapeptide histidine tag (positions 567-572 of SEQ ID NO:25). SEQ ID NO:25 is encoded by the nucleotide sequence represented by SEQ ID NO:24 (codon optimized for yeast expression). The alpha leader sequence (positions 1-89 of SEQ ID NO:25) could be substituted with a different N-terminal sequence designed to impart resistance to proteasomal degradation and/or stabilize expression, such as the peptide represented by SEQ ID NO:21, or an N-terminal peptide from a different yeast alpha leader sequence such as SEQ ID NO:20, or by a MUC1 signal sequence. The hexahistidine C-terminal tag is optional, and facilitates identification and/or purification of the protein. As compared to the wild-type MUC1 protein used as a template, the sequence in GI-6106 contains the following amino acid substitutions to create a variety of agonist epitopes (substitution positions given with reference to SEQ ID NO:25, with further reference to the location of the substitution in a wild-type MUC1 represented by Accession No. NP_001191214): T184L (position 93 in wild-type MUC1), A232Y (position 161 in wild-type MUC1), P233L (position 162 in wild-type MUC1), G240V (position 169 in wild-type MUC1), S241Y (position 170 in wild-type MUC1), T242L (position 171 in wild-type MUC1), A483Y (position 392 in wild-type MUC1), C497V (position 406 in wild-type MUC1), T535L (position 444 in wild-type MUC1), D536F (position 445 in wild-type MUC1), and S551Y (position 460 in wild-type MUC1).

A plasmid containing MUC1 agonist antigen for GI-6106 was transfected into W303a yeast and transformants were selected after 3 days of growth at 30° C. on uridine dropout agar (UDA). Single colonies were re-streaked onto uridine and leucine dropout agar (ULDA) plates and incubated at 30° C. for an additional 4 days to select for cells with elevated plasmid copy number.

A single colony of GI-6106 was removed from the ULDA plate and used to inoculate 25 mL of UL2 liquid medium (starter culture). The starter culture was incubated with shaking at 30° C. to a density of ~3 YU/mL, and then used to inoculate an intermediate culture to 0.3 YU/mL. The intermediate culture and grown to a density of 3 YU/mL, and then used to inoculate a final culture to a density of 0.04 YU/mL. The final culture was grown to a density of 3 YU/mL, then treated with 0.5 mM copper sulfate for 3 h at 30° C. to induce Muc1 agonist v2.0 antigen expression.

The induced cells were washed once with PBS, heat killed at 56° C. for 1 h, then thrice washed in PBS. Total protein content of the heat killed cells was measured by Amidoschwarz assay and the agonist antigen content was measured by western blot, with a monoclonal antibody recognizing a C-terminal hexahistidine epitope tag. Antigen quantity was determined by interpolation against a standard curve comprised of his tagged HCV NS3 protein. Results showed that the GI-6106 yeast expressed the antigen (data not shown); antigen content for GI-6106 was estimated to be approximately 2940 Ng/YU.

Example 5

The following examples describe the phenotypic and functional analysis of the effects yeast-MUC1 immunotherapy compositions on human dendritic cells.

In order to evaluate the effect of the yeast-MUC1 immunotherapy compositions described in Examples 1 and 2 on the phenotype and function of dendritic cells, the following experiments were performed.

In a first experiment, human dendritic cells (DCs) were cultured for 48 hours with: (1) media alone (Untreated), (2) CD40L (1 µg/ml) plus enhancer for ligands (1 µg/ml) as a positive control; (3) control yeast (Control Yeast; yeast comprising an empty vector (no MUC1 antigen insert)); (4) the yeast-MUC1 immunotherapy composition known as GI-6101, grown under standard growth conditions as described in Example 1 (GI-6101); (5) the yeast-MUC1 immunotherapy composition known as GI-6101, grown under neutral pH growth conditions as described in Example 1 (GI-6101 (DEC)); (6) the yeast-MUC1 immunotherapy composition known as GI-6104 (GI-6104), grown under standard growth conditions as described in Example 2; or (7) the yeast-MUC1 immunotherapy composition known as GI-6104, grown under neutral pH growth conditions as described in Example 2 (GI-6104 (DEC)). Dendritic cells and yeast were combined at a ratio of 1:10 (DC:yeast). DCs were harvested and analyzed by flow cytometry for DC surface-marker expression. The results are shown in Table 1 below as the percentage of positive cells and MFI (parentheses).

TABLE 1

| Treatment of DCs | CD80 | CD83 | CD86 | CD54 | Class I | Class II |
|---|---|---|---|---|---|---|
| Untreated | 6.4 (3088) | 28.6 (3352) | 97.6 (19731) | 96.3 (14463) | 99.2 (19582) | 80.9 (8678) |
| CD40L | 59.3 (3932) | 79.6 (4364) | 99.8 (33554) | 99.6 (44958) | 99.9 (25589) | 81.6 (5908) |
| Control Yeast | 41.2 (4479) | 54.7 (3953) | 99.1 (49674) | 96.0 (26634) | 99.3 (40996) | 93.7 (8953) |
| GI-6101 | 56.2 (5456) | 72.9 (4654) | 99.0 (59333) | 96.0 (41385) | 99.6 (43290) | 83.1 (7684) |
| GI-6101 (DEC) | 65.3 (6090) | 74.3 (4149) | 99.6 (63934) | 98.2 (41984) | 99.9 (33384) | 87.0 (6304) |
| GI-6104 | 57.0 (5433) | 65.8 (4498) | 99.0 (59460) | 96.1 (40096) | 99.5 (42884) | 90.6 (6992) |
| GI-6104 (DEC) | 52.0 (5502) | 63.0 (4012) | 99.2 (55133) | 97.6 (31823) | 99.9 (35846) | 88.7 (6423) |

The results show that yeast (control yeast and yeast expressing MUC1 antigens), regardless of the method of growth, upregulated the expression of CD80 and CD83 on dendritic cells as compared to untreated cells. CD80, or B7.1, is a costimulatory molecule necessary for T cell activation and survival that is upregulated on activated dendritic cells. CD83 is a marker of dendritic cell maturation. Accordingly, this experiment shows that the yeast-MUC1 immunotherapeutic compositions can upregulate DC maturation markers.

In a second experiment, dendritic cell cytokine and chemokine production were evaluated after culture with the yeast-MUC1 immunotherapeutics. Briefly, human DCs from a normal donor (a donor who was believed to be cancer-free) were cultured for 5 days with granulocyte macrophage-colony stimulating factor (GM-CSF) and interleukin-4 (IL-4), or treated with CD40L (1 µg/ml, Enzo Life Sciences) plus enhancer for ligands (1 µg/ml, Enzo Life Sciences) for 24 hours, or with Control Yeast (empty vector), GI-6101 cultured under standard growth conditions (GI-6101), GI-6101 cultured under neutral pH conditions (GI-6101 (DEC)), GI-6104 cultured under standard growth conditions (GI-6104), or GI-6104 cultured under neutral pH conditions (GI-6104 (DEC)) for 48 hrs (DC:yeast ratio=1:10). Cultured supernatants were collected and screened for cytokine and chemokine production by multiplex cytokine/chemokine kit. Results are expressed in pg/ml, and shown in Table 2.

TABLE 2

| Treatment of DCs | IL-2 | IL-8 | IL-12p70 | IL-1β | GM-CSF | IFN-γ | IL-6 | IL-10 | TNF-α |
|---|---|---|---|---|---|---|---|---|---|
| CD40L | 14.9 | 829.6 | 152.8 | 6.3 | 5069.8 | 22.3 | 933.2 | 74.3 | 8103.2 |
| Control Yeast | 2.8 | 129.4 | 316.1 | 1.8 | 4420.3 | 6.3 | 49.2 | 3.9 | 333.7 |
| GI-6101 | 3.5 | 183.3 | 443.3 | 2.1 | 4174.8 | 5.9 | 75.3 | 4.4 | 487.1 |
| GI-6101 (DEC) | 11.5 | 866.6 | 864.2 | 4.3 | 3697.8 | 31.8 | 192.0 | 10.7 | 2148.2 |
| GI-6104 | 4.5 | 315.7 | 568.0 | 1.9 | 4156.0 | 7.3 | 121.8 | 5.0 | 477.0 |
| GI-6104 (DEC) | 6.5 | 725.2 | 587.8 | 3.2 | 3165.5 | 13.2 | 140.4 | 8.5 | 642.0 |

The results in Table 2 shown that the treatment of dendritic cells from a normal donor with yeast-MUC1 immunotherapy compositions described in Examples 1 and 2 increases cytokine and chemokine production by these cells. Notably, interferon-γ (IFN-γ) production was increased after exposure to yeast-MUC1 immunotherapy compositions grown under neutral pH conditions, which is expected to enhance TH1 and CD8+ T cell responses. In addition, yeast-MUC1 immunotherapy compositions grown under neutral pH conditions induce higher cytokine and chemokine production by DCs, with the yeast-MUC1 immunotherapy composition known as GI-6101 (neutral pH) showing the highest stimulation of DC cytokine and chemokine production. Numbers highlighted in bold type show cytokine/chemokine induction that is statistically significantly improved as compared to untreated control (data not shown).

The experiment shown in Table 2 was repeated using dendritic cells isolated from a different normal donor. The results (data not shown) are comparable to those shown in Table 2 and confirm that yeast-MUC1 immunotherapy compositions induce cytokine and chemokine production by dendritic cells, and that the yeast-MUC1 composition known as GI-6101, grown under neutral pH growth conditions, induces the highest levels of cytokine and chemokine production by dendritic cells among the two yeast-MUC1 compositions grown under each condition.

Taken together, these results show that yeast-MUC1 immunotherapy compositions can activate dendritic cells and induce cytokine and chemokine production that is associated with a productive immune response.

Example 6

The following example shows that yeast-MUC1 immunotherapy compositions of the invention can activate MUC1-specific T cells.

T-3-P93L is a MUC-1 specific T cell line that specifically recognizes the MUC1 agonist peptide, denoted P93L, in the context of HLA-A2. P93L is a peptide spanning positions 92-101 of a full-length MUC1 protein (e.g., ATWGQDVTSV; positions 92-101 of SEQ ID NO:11), except that the threonine at position 2 of this peptide (position 93 in positions 92-101 of SEQ ID NO:11) is substituted with a leucine, creating an agonist peptide. P93L binds to HLA-A2 at higher levels than the native (wild-type) peptide, and is a better inducer of MUC1-specific T cells than the native peptide (higher production of TH1 cytokines (see U.S. Patent Application Publication No. 2008/0063653). The T cell line T-3-P93L can specifically lyse HLA-A2-positive, MUC1-positive tumor targets in vitro (data not shown). This T cell line is specific for a portion of MUC1 that is within the MUC1-N subunit.

In this experiment, DCs from a normal donor, prepared as described in Example 5 were treated with the yeast-immunotherapy compositions described in Examples 1 and 2, or with control yeast (empty vector), CD40L (positive control) or untreated (negative control) using conditions described above in Example 5. DCs treated with control yeast or with CD40L were pulsed with or without the P93 L peptide (P93L was used at 10 µg/ml). Treated DCs were then used as antigen presenting cells (APCs) to evaluate their ability to stimulate the MUC1-specific T cell line T-3-P93L (T cell:DC ratio=10:1). 24 hour culture supernatants were collected and screened for the secretion of interferon-γ (IFN-γ). The results are shown in Table 3, expressed as the amount of IFN-γ produced by the T cells in pg/ml.

TABLE 3

| DCs | Treatment | MUC-1 peptide | MUC-1-specific T cells | IFN-γ |
|---|---|---|---|---|
| − | None | − | + | <15.6 |
| + | CD40L | − | + | <15.6 |
| + | CD40L | + | + | 217.1 |
| + | Control yeast | − | + | <15.6 |
| + | Control Yeast | + | + | 339.2 |
| + | GI-6101 | − | + | 342.1 |
| + | GI-6101 (DEC) | − | + | 393.5 |
| + | GI-6104 | − | + | 44.2 |
| + | GI-6104 (DEC) | − | + | 32.3 |

The results show that dendritic cells treated with GI-6101, produced under both standard and neutral pH conditions, and which expresses VNTR domains of the MUC1-N subunit, was able to stimulate the MUC1-N-specific T cells to produce significant amounts of IFN-γ. GI-6104, which does not express antigen from the MUC1-N protein (GI-6104 only expresses MUC1 antigen from the cytoplasmic domain (CD)), did not stimulate the MUC1-N-specific T cells.

In a second experiment, the MUC1-C-specific T cell line, denoted T-15-P1240(1Y), was stimulated with DCs that had been treated as in the experiment above, to determine whether yeast-MUC1 immunotherapy compositions of the invention could stimulate these T cells. The T-15-P1240(1Y) cell line is a MUC-1 specific T cell line that specifically recognizes the MUC1 agonist peptide, denoted P1240(1Y), which is a MUC1-C peptide, in the context of HLA-A2. P1240(1Y) is a peptide spanning positions 1240-1248 of a full-length MUC1 protein (e.g., SLSYTNPAV; positions 1240-1248 of SEQ ID NO:11), except that the serine at position 1 of this peptide (position 1240 in positions 1240-1248 of SEQ ID NO:11) is substituted with a lysine, creating an agonist peptide. P1240(1Y) binds to HLA-A2 as well or better than the native (wild-type) peptide, and is a better inducer of MUC1-specific T cells than the native peptide (higher production of TH1 cytokines. The T cell line T-15-P1240(1Y) can specifically lyse HLA-A2-positive, MUC1-positive tumor targets in vitro (data not shown). This T cell line is specific for a portion of MUC1 that is within the MUC1-C subunit, and specifically, the cytoplasmic domain (CD).

In this experiment, DCs were generated from PBMCs of a healthy HLA-A2 positive donor, and prepared as described in Example 5. The DCs were treated with the yeast-immunotherapy compositions described in Examples 1 and 2, or with CD40L (positive control) or untreated (negative control) using conditions described above in Example 5. DCs treated with CD40L were pulsed with or without the P1240 (1Y) peptide (peptide was used at 10 µg/ml). Treated DCs were then used as antigen presenting cells (APCs) to evaluate their ability to stimulate the MUC1-specific T cell line T-15-P1240(1Y) (T cell:DC ratio=10:1). 24 hour culture supernatants were collected and screened for the secretion of interferon-γ (IFN-γ). The results are shown in Table 4, expressed as the amount of IFN-γ produced by the T cells in pg/ml.

TABLE 4

| DCs | Treatment | MUC1-C peptide | MUC1-C-specific T cells | IFN-γ |
|---|---|---|---|---|
| − | — | − | + | 106.1 |
| + | CD40L | − | + | <15.6 |
| + | CD40L | + | + | 2402.8 |
| + | GI-6101 | − | + | 852.1 |
| + | GI-6101 | − | − | 67.4 |
| + | GI-6101/DEC | − | + | 1667.9 |
| + | GI-6101/DEC | − | − | 113.7 |
| + | GI-6104 | − | + | 583.6 |
| + | GI-6104 | − | − | 103.4 |
| + | GI-6104/DEC | − | + | 1155.1 |
| + | GI-6104/DEC | − | − | 63.6 |

The results show that both GI-6101 and GI-6104, grown under standard or neutral pH conditions, were able to stimulate the MUC1-C-specific T cells to produce significant amounts of IFN-γ. Yeast-MUC1 immunotherapy compositions grown under neutral pH conditions (both GI-6101 and GI-6104) stimulated higher levels of IFN-γ production by the T cells than yeast-MUC1 immunotherapy compositions grown under standard conditions.

In a third experiment, the experiment described in Table 4 above was repeated, but using different DC:T cell ratios for DCs treated with the yeast-MUC1 immunotherapy compositions GI-6101 and GI-6104. The results are presented below in Table 5.

TABLE 5

| DCs | Treatment | MUC1-C peptide | DC:T cell | MUC1-C-specific T cells | IFN-γ (pg/ml) |
|---|---|---|---|---|---|
| − | GI-6101 | − | | + | 48 |
| + | GI-6101 | − | | − | <15.6 |
| + | GI-6101/DEC | − | | − | <15.6 |
| + | GI-6104 | − | | − | <15.6 |
| + | GI-6104/DEC | − | | − | <15.6 |
| + | GI-6101 | − | 10:1 | + | 981.8 |
| | | | 20:1 | + | 628.4 |
| | | | 40:1 | + | 426.4 |
| + | GI-6101/DEC | − | 10:1 | + | 2039.1 |
| | | | 20:1 | + | 1074.3 |
| | | | 40:1 | + | 768.4 |

TABLE 5-continued

| DCs | Treatment | MUC1-C peptide | DC:T cell | MUC1-C-specific T cells | IFN-γ (pg/ml) |
|---|---|---|---|---|---|
| + | GI-6104 | − | 10:1 | + | 534.2 |
|   |         |   | 20:1 | + | 514.6 |
|   |         |   | 40:1 | + | 330.9 |
| + | GI-6104/DEC | − | 10:1 | + | 1177.8 |
|   |             |   | 20:1 | + | 824.4 |
|   |             |   | 40:1 | + | 674.6 |
| + | CD40 L | + |  | + | 2275.4 |

The results again show that both GI-6101 and GI-6104, grown under standard or neutral pH conditions, were able to stimulate the MUC1-C-specific T cells to produce significant amounts of IFN-γ, and that the compositions grown under neutral pH conditions stimulated higher levels of IFN-γ production by the T cells than yeast-MUC1 immunotherapy compositions grown under standard conditions. The results further show a dose response as the number of DCs increases relative to the number of T cells.

Taken together, these results show that yeast-MUC1 immunotherapy compositions can activate MUC1-specific T cells in an antigen-specific manner, as illustrated by the IFN-γ release from T cells stimulated by DCs treated with the yeast-MUC1 immunotherapy compositions. These results also show an advantage for the production of IFN-γ by T cells as a result of using yeast-MUC1 immunotherapy compositions grown under neutral pH conditions.

Example 7

The following example demonstrates that yeast-MUC1 compositions of the invention can expand and stimulate MUC1-specific T cells from cancer patients.

In this experiment, DCs are prepared from the PBMCs of cancer patients (post treatment with a cancer therapy, which can include chemotherapy or viral vaccine treatment, and/or pre-treatment). The DCs are prepared in a 5-day culture in presence of GM-CSF and IL-4, followed by incubation in presence of yeast (GI-6101 and/or GI-6104, cultured under standard or neutral pH conditions). After 48-hours co-culture, the DCs are used as APCs for stimulation of autologous T cells by measuring cytokine production and/or proliferation of CD4+ T cells. Yeast-MUC1 immunotherapy compositions are expected to expand and activate T cells from the cancer patients.

In a second experiment, DCs are prepared from the PBMCs of cancer patients (post treatment with a cancer therapy, which can include chemotherapy or viral vaccine treatment, and/or pre-treatment). The DCs are prepared in a 5-day culture in presence of GM-CSF and IL-4, followed by incubation in presence of yeast (GI-6101 and/or GI-6104, cultured under standard or neutral pH conditions). After 48-hours co-culture, the DCs are used as APCs for stimulation of autologous T cells. Each cycle of IVS consists of 3 days in absence of IL-2, following by 4 additional days in presence of 20 U/ml of recombinant IL-2. Tetramers specific for a MUC1 peptide are used to detect the percentage of CD8+ T cells that are expanded by the treatment with the yeast-MUC1 immunotherapy compositions. Yeast-MUC1 immunotherapy compositions are expected to expand and activate T cells from the cancer patients.

In a third experiment, yeast-MUC1 immunotherapeutic compositions are used to generate MUC1-specific CTLs from PBMCs that lyse MUC1-expressing targets. In this experiment, MUC1-specific T cells from normal donors and/or from cancer patients (post treatment with a cancer therapy, which can include chemotherapy or viral vaccine treatment, and/or pre-treatment), are expanded in vitro using DCs incubated with yeast-MUC1 immunotherapy compositions (GI-6101 or GI-6104) for 2 cycles of in vitro stimulation (IVS). At day 5, $CD8^+$ T cells are isolated and used in an overnight CTL assay against tumor cells that express MUC1. These experiments are expected to demonstrate that yeast-MUC1 immunotherapeutic compositions can generate MUC1-specific CTLs that are capable of killing a MUC1-expressing tumor cells.

Example 8

The following example demonstrates that immunization with a yeast-MUC1 immunotherapeutic composition reduces MUC1-expressing tumors in vivo.

In this experiment, mice receive tumor cells expressing a recombinant human MUC1 protein via the tail vein (day 0). Four days post-tumor implantation, animals receive weekly vaccinations with yeast control (YVEC, or empty vector yeast) versus yeast-MUC1 (GI-6101 or GI-6104), administered at a dose of 1 YU per site at four different sites (4 YU total per dose). At day 40 post-tumor implantation, animals are sacrificed and the number of lung tumor nodules are evaluated. It is expected that the yeast-MUC1 immunotherapy compositions are capable of reducing MUC1-expressing tumors in mice, as compared to mice receiving yeast alone (no MUC1 antigen).

Example 9

The following example describes a phase 1 clinical trial in subjects with MUC1-positive cancer.

An open-label, dose-escalation phase 1 clinical trial is run using a yeast-MUC1 immunotherapy composition known as GI-6101 described in Example 1 or GI-6104 described in Example 2 (grown either under standard growth conditions or under neutral pH conditions). 12-24 subjects with a MUC1-positive tumor are administered the yeast-MUC1 immunotherapy composition in a sequential dose cohort escalation protocol utilizing dose ranges of 4 Y.U. (1 Y.U.×4 sites), 16 Y.U. (4 Y.U.×4 sites) and 40 Y.U. (10 Y.U.×4 sites), administered subcutaneously. The yeast-MUC1 immunotherapy is administered at 2 week intervals for 3 months, and then monthly. An expansion cohort of patients (n=10) at maximum tolerated dose (MTD) or the observed best dose are selected for additional study. The results monitor safety as a primary endpoint, and as secondary endpoints, antigen-specific T cell responses (e.g., MUC1-specific $CD8^+$ T cells emerging or expanding on treatment) as well as clinical activity.

GI-6101 and GI-6104 are expected to be safe and well-tolerated with no significant toxicities. In addition, GI-6101 or GI-6104 are expected to produce treatment-emergent MUC1-specific T cell responses or an improvement in pre-existing MUC1-specific baseline T cell responses in a statistically significant number of patients. Some patients are also expected to have stabilized disease.

Example 10

The following example describes a clinical trial (P1/P2) using Yeast-MUC1 immunotherapeutic compositions.

Increased MUC1 expression has been observed in ~70% of the acute myeloid leukemia (AML) cases, suggesting that elevated MUC1 levels may be involved in regulating the proliferative potential of the immature leukemic compartment.

In a first clinical trial, first-line use of the yeast-based immunotherapy product known as GI-6101 (see Example 1) is implemented in the setting of MUC1-positive AML (this trial design is also applicable to other yeast-MUC1 immunotherapy compositions, such as GI-6104). The use of GI-6101 is designed to complement existing cytotoxic standard of care regimens, cytarabine and an anthracycline (e.g., daunorubicin), in an add-on approach by promoting immune killing of MUC1-positive leukemic cells, as well as eliminating MUC1 leukemic cells which can escape terminal differentiation (apoptosis) pathways. Endpoints include improvements in the induction of remission as well as overall survival (pre- and post-transplant).

In a second trial, GI-6101 is used in the bone marrow transplantation (BMT) setting to prevent relapse of AML in patients with MUC1-positive disease (this trial design is also applicable to other yeast-MUC1 immunotherapy compositions, such as GI-6104). Clinical strategies which evaluate the vaccination of bone marrow donors (adoptive transfer) and/or vaccination of bone marrow recipients in the post transplant period are used to reduce the rate of relapse after BMT.

(A) Clinical Study Design for First Line Therapy of MUC1-Positive AML Patients with GI-6101 Plus Cytarabine and Daunorubicin Versus Standard of Care Alone.

Patients receive induction chemotherapy consisting of continuous intravenous infusion of cytaribine (cytosine arabinoside) at 100-200 mg/m2 per day×7 days plus intravenous daunoribicin (or daunomycin (daunomycin cerubidine)) 45 mg/m2 on days 1, 2, and 3 of cytaribine therapy, or an accepted variation of this regimen, followed by GI-6101 (or placebo) administration 14 days after completion of the induction cycle of chemotherapy. GI-6101 (or placebo) are then administered 14 days after re-induction therapy or 14 days after every subsequent consolidation cycle of chemotherapy. After induction, re-induction, and consolidation therapy, GI-6101 (or placebo) are administered each month for up to 3 years with the primary objective of preventing relapse of remission.

It is expected that the use of GI-6101 enhances the relapse of remission in patients as compared to those receiving placebo.

(B) Clinical Study Design for Post-BMT Therapy of MUC1-Positive AML with GI-6101 Versus Placebo.

For MUC1-positive AML patients who require myeloablative therapy followed by bone marrow transplant, GI-6101 (or placebo) are administered to the bone marrow donor 7-14 days prior to the donation of bone marrow, and GI-6101 (or placebo) are administered to the bone marrow recipient on a monthly basis for up to 3 years after bone marrow engraftment occurs. The primary objective is to reduce the rate of AML relapse.

It is expected that the use of GI-6101 reduces the rate of relapse in AML patients as compared to those patients taking placebo.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

What is claimed is:

1. A combination immunotherapeutic composition, wherein the immunotherapeutic composition comprises:
   a) a yeast-MUC1 immunotherapeutic composition comprising:
      i) a yeast vehicle; and
      ii) a fusion protein expressed by the yeast vehicle, wherein the fusion protein comprises a MUC1 antigen comprising an amino acid sequence that is at least 95% identical to SEQ ID NO:25 and wherein the MUC1 antigen comprises at least 2 amino acid substitutions selected from the group consisting of L184, Y232, L233, V240, Y241, L242, Y483, V497, L535, F536 and Y551 with reference to SEQ ID NO:25; and
   b) a virus-based immunotherapeutic composition comprising a recombinant viral vector encoding a cancer antigen.

2. The combination immunotherapeutic composition of claim 1, wherein the MUC1 antigen comprises an amino acid sequence that is at least 95% identical to positions 92-566 of SEQ ID NO:25.

3. The combination immunotherapeutic composition of claim 1, wherein the MUC1 antigen consists of positions 92-566 of SEQ ID NO:25.

4. The combination immunotherapeutic composition of claim 1, wherein the MUC1 agonist antigen comprises an amino acid sequence of SEQ ID NO:25.

5. The combination immunotherapeutic composition of claim 1, wherein the yeast vehicle is a whole yeast.

6. The combination immunotherapeutic composition of claim 1, wherein the yeast vehicle is heat-inactivated.

7. The combination immunotherapeutic composition of claim 1, wherein the yeast vehicle is from *Saccharomyces cerevisiae*.

8. The combination immunotherapy composition of claim 1, wherein the virus-based immunotherapy composition further comprises at least one viral vector comprising one or more nucleic acid sequences encoding one or more immunomodulatory compounds.

9. The combination immunotherapy composition of claim 8, wherein genes encoding the one or more immunomodulatory compounds and genes encoding the cancer antigen are inserted into the same viral vector.

10. The combination immunotherapy composition of claim 8, wherein the one or more immunomodulatory compounds can stimulate a protective immune response.

11. The combination immunotherapy composition of claim 8, wherein the one or more immunomodulatory compounds can suppress a harmful immune response.

12. The combination immunotherapeutic composition of claim 1, further comprising an immunomodulatory compound selected from the group consisting of cytokines, chemokines, hormones, lipidic derivatives, peptides, proteins, polysaccharides, small molecule drugs, antibodies and antigen binding fragments thereof, anti-cytokine antibodies, anti-cytokine receptor antibodies, anti-chemokine antibodies, vitamins, polynucleotides, nucleic acid binding moieties, aptamers, and growth modulators.

* * * * *